(12) United States Patent
Kelly et al.

(10) Patent No.: US 7,494,996 B2
(45) Date of Patent: Feb. 24, 2009

(54) SUBSTITUTED 4,5-DIHYDRO-1,2,4-TRIAZIN-6-ONES, 1,2,4-TRIAZIN-6-ONES AND THEIR USE AS FUNGICIDES AND INSECTICIDES

(75) Inventors: Martha Jean Kelly, Collegeville, PA (US); Karen Anderson Evans, Harleysville, PA (US); James Joseph Gallagher, Ambler, PA (US); Mark Joseph Mulvihill, East Northport, NY (US)

(73) Assignee: Dow AgroSciences LLC, Indianapolis, IN (US)

( * ) Notice: Subject to any disclaimer, the term of this patent is extended or adjusted under 35 U.S.C. 154(b) by 575 days.

(21) Appl. No.: 10/380,435

(22) PCT Filed: Oct. 26, 2001
(Under 37 CFR 1.47)

(86) PCT No.: PCT/US01/50363

§ 371 (c)(1),
(2), (4) Date: Oct. 24, 2003

(87) PCT Pub. No.: WO02/067675

PCT Pub. Date: Sep. 6, 2002

(65) Prior Publication Data

US 2004/0242580 A1 Dec. 2, 2004

Related U.S. Application Data

(60) Provisional application No. 60/243,803, filed on Oct. 27, 2000.

(51) Int. Cl.
*C07D 253/06* (2006.01)
*C07D 253/065* (2006.01)
*C07D 253/10* (2006.01)
*A01N 43/707* (2006.01)

(52) U.S. Cl. .................. 514/242; 514/243; 544/182; 544/183

(58) Field of Classification Search ............... 544/182, 544/184, 183; 504/228, 229, 230; 514/242, 514/243
See application file for complete search history.

(56) References Cited

U.S. PATENT DOCUMENTS

| 4,716,164 | A | * | 12/1987 | Hargreaves et al. | .......... 514/243 |
| 5,574,033 | A | * | 11/1996 | Kobayashi et al. | ....... 514/222.5 |
| 6,159,980 | A | | 12/2000 | Arvanitis et al. | ............ 514/255 |
| 6,825,192 | B1 | | 11/2004 | Ito et al. | ................... 514/222.5 |

FOREIGN PATENT DOCUMENTS

| DE | 42 39 540 A1 | 5/1994 |
| WO | WO-00/47567 A1 * | 8/2000 |

OTHER PUBLICATIONS

M. Kammoun et al. , Journal of Fluorine Chemistry 105(1), 83-86, 2000.*
Kammoun et al., CAPLUS Abstract, CA 133: 56591, 2000.*
Collins et al., Australian Journal of Chemistry, 52(I0), 971-975, 1999.*
Collins et al., CAPLUS Abstract, CA 132: 207829, 2000.*

* cited by examiner

*Primary Examiner*—Venkataraman Balasubramanian
(74) *Attorney, Agent, or Firm*—C. W. Arnett

(57) ABSTRACT

This invention relates to dihydrotriazinones, triazinones and related compounds, compositions comprising such compounds and an agronomically acceptable carrier, and the use thereof as broad spectrum fungicides and insecticides. This invention also teaches methods of preparing these compounds as well as methods of using the compounds as fungicides and insecticides.

7 Claims, No Drawings

SUBSTITUTED 4,5-DIHYDRO-1,2,4-TRIAZIN-6-ONES, 1,2,4-TRIAZIN-6-ONES AND THEIR USE AS FUNGICIDES AND INSECTICIDES

This application claims priority from U.S. provisional application 60/243,803, which was filed on Oct. 27, 2000.

The need continues for novel and improved broad spectrum, agrochemical fungicides and insecticides. This is particularly so since the targets of fungicides and insecticides can become resistant to known fungicides and insecticides over time and after use of such compounds and their compositions. Additionally, economic and environmental considerations can favor fungicides and insecticides having different modes of performance than those currently used. This invention relates to dihydrotriazinones, triazinones and related compounds, compositions comprising such compounds and an agronomically acceptable carrier, and the use thereof as broad spectrum fungicides and insecticides. This invention also teaches methods of preparing these compounds as well as methods of using the compounds as fungicides and insecticides.

Certain methylated 3-phenyl-4,5-dihydro-1,2,4-triazin-6 (1H)-ones are disclosed by Collins et al., *Aust. J. Chem.*, 52, 379-385 (1999) as having potential as crop potential agents; however, the fungicidal and insecticidal dihydrotriazinones and triazinones of the present invention are not suggested. Other 4,5-dihydro-1,2,4-triazin-6(1H)-ones are presented in a review by Neunhoeffer et al., "Chemistry of 1,2,3-Triazines and 1,2,4-Triazines, Tetrazines, and Pentazines", 605-607, John Wiley and Sons, Inc., New York, N.Y. (1978); no utility for these compounds is suggested. Various aryl triazinones and aryl triazinophthalazines are disclosed by Kutscher et al. in ZA 938799, Nov. 24, 1993 as drugs for the treatment of bronchial asthma, allergies of the most varied origin, inflammatory processes, cardiac insufficiency and hypertension; no pesticidal utilization for these compounds is suggested. Some triazinones, among other nitrogen containing heterocycles, are disclosed by Kanellakopulos et al. in U.S. Pat. No. 5,814, 645, Sep. 29, 1998 as having insecticidal activity, but the compounds of the present invention are not disclosed. Sanière et al., in *Tetrahedron Letters*, 41, 671-674 (2000), exemplify certain 4,5-dihydro-1,2,4-triazin-6(1H)-ones for use as scaffolds for combinatorial chemistry; the compounds of the present invention and their uses are not disclosed.

One embodiment of this invention relates to a compound of the formula (I)

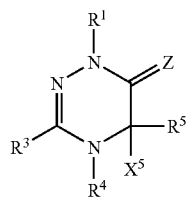

(I)

wherein $R^1$ is alkyl, haloalkyl, cyanoalkyl, alkenyl, haloalkenyl, alkynyl, haloalkynyl, cycloalkylalkynyl, alkoxyalkyl, alkylthioalkyl, cycloalkyl, cycloalkylalkyl, trialkylsilylalkyl where the three alkyl groups may be the same or different, alkoxycarbonyl, alkylcarbonyl, alkoxycarbonylalkyl, phenyl, naphthyl, or phenyl or naphthyl substituted with from one to three substituents independently selected from the group consisting of alkyl, halo, nitro, alkoxy, alkylthio, haloalkyl, haloalkylthio and haloalkoxy, phenalkyl or phenalkyl substituted on the phenyl ring with from one to three substituents independently selected from the group consisting of alkyl, halo, alkoxy, haloalkyl and haloalkoxy, pyridyl or pyridyl substituted with from one to two substituents independently selected from the group consisting of alkyl and halo, furyl, thienyl, thenyl or furyl, thienyl or thenyl substituted with halo or alkyl on the furyl or thienyl ring, benzothienyl, benzofuranyl or benzothienyl or benzofuranyl substituted with halo, alkyl or haloalkyl, $R^3$ is alkyl, cycloalkyl, cycloalkylalkyl, phenalkyl or phenalkyl substituted on the phenyl ring with from one to three substituents independently selected from the group consisting of alkyl, halo, alkoxy, haloalkyl and haloalkoxy, aryl selected from phenyl, naphthyl, and phenyl and naphthyl substituted with from one to five substituents independently selected from the group consisting of halo, alkyl, haloalkyl, haloalkoxy, alkylthio, haloalkylthio, alkylsulfinyl, alkylsulfonyl, nitro, cyano, dialkylamino wherein the alkyl groups may be the same or different or together with the nitrogen to which they are attached form a 5- or 6-membered heterocyclic ring, or phenyl and naphthyl substituted with a heteroaryl group selected from furyl, thienyl, quinolinyl, isoquinolinyl, benzofuranyl, benzothienyl, pyridyl, pyridazinyl, pyrimidinyl, pyrazinyl, 1,2,3-thiadiazol-4-yl, 3-(4,5-dihydro-1,2,4-triazin-6-one)yl and oxazol-5-yl, and furyl, thienyl, quinolinyl, isoquinolinyl, benzofuranyl, benzothienyl, pyridyl, pyridazinyl, pyrimidinyl, pyrazinyl, 1,2,3-thiadiazol-4-yl, 3-(4,5-dihydro-1,2,4-triazin-6-one) yl and oxazol-5-yl substituted with one or two substituents independently selected from halo, alkyl, alkoxy, haloalkoxy, haloalkyl, alkylthio, nitro and cyano, phenyl, phenoxy, and phenyl and phenoxy substituted with one or two substituents independently selected from the group consisting of halo, alkyl, alkoxy, haloalkyl, haloalkoxy, alkylthio, nitro and cyano, heteroaryl selected from furyl, thienyl, quinolinyl, isoquinolinyl, benzofuranyl, benzothienyl, pyridyl, pyridazinyl, pyrimidinyl, pyrazinyl, pyrazolyl, 1,2,3-thiadiazol-4-yl, thiazolyl, triazolyl, triazinyl, isoxazolyl and oxazolyl, and furyl, thienyl, pyridyl, pyridazinyl, pyrimidinyl, pyrazinyl, 1,2,3-thiadiazol-4-yl and oxazolyl substituted with one or two substituents independently selected from halo, alkyl, alkoxy, haloalkoxy, haloalkyl, alkylthio, haloalkylthio, nitro and cyano, $R^4$ is a hydrogen atom, alkyl, haloalkyl, alkylcarbonyl, alkylcarbonylalkyl, cycloalkyl, cycloalkylalkyl, cycloalkylcarbonyl, alkylsulfonyl, alkylthio, amino, alkylamino, dialkylamino wherein the alkyl groups may be the same or different or together with the nitrogen to which they are attached form a 5- or 6-membered heterocyclic ring, cyano, alkenyl, alkenylsulfonyl, haloalkenyl, alkenylcarbonyl, alkynyl, haloalkynyl, alkoxycarbonyl, haloalkoxycarbonyl, alkoxycarbonylalkyl, alkoxycarbonylthio, (alkylthio) carbonyl, alkyl(thiocarbonyl), alkylthiothiocarbonyl, alkenyloxycarbonyl, alkenylthiothiocarbonyl, alkynyloxycarbonyl, alkynylthiothiocarbonyl, alkoxyoxalyl, alkylcarbonyloxyalkoxy-carbonyl, aralkyl, arylcarbonyl, arylsulfonyl, arylsulfonylalkenyl, aryloxycarbonyl, aryloxythiocarbonyl, arylthiothiocarbonyl or aralkyl, arylcarbonyl, arylsulfonyl, arylsulfonylalkenyl, aryloxycarbonyl, aryloxythiocarbonyl, arylthiothiocarbonyl substituted on an aromatic ring with from one to two substituents independently selected from halo and alkyl, or thenyl or thenyl substituted on the thienyl ring with from one to two substituents independently selected from halo and alkyl, $R^5$ is a hydrogen atom, alkyl, haloalkyl, alkylcarbonyl, alkylcarbonylalkyl, formyl, alkoxy, alkoxycarbonyl, alkoxycarbonyl-oxy, alkylcarbonyloxy, alkoxycarbonylthio, alkylcarbonylthio, alkylthio, hydroxy, mercapto, alkenyl, alkynyl, cyano, amino, alkylamino, dialkylamino wherein the alkyl groups may be the same or different or together with the nitrogen to which they are attached form a 5- or 6-membered heterocyclic ring, aryl, aralkyl, aryloxy, arylthio, arylcarbonylthio or aryl, aralkyl, aryloxy, arylthio, arylcarbonylthio substituted on the aryl ring with from one to three substituents independently selected from the group consisting of alkyl, halo, alkoxy, haloalkyl, haloalkoxy, amino, alkylamino and dialkylamino wherein the alkyl groups may be the same or different or together with the nitrogen to which they are attached form a 5- or 6-membered heterocyclic ring, or $R^4$ can form a fused ring to the $R^3$ substituent when the $R^3$ substituent is aryl or heteroaryl wherein $R^4$ is selected from —CH(R)—, —O—, —S—, —N(R)—, —C(=O)—, —O(C=O)—, —C(=O)O—, —CH$_2$CH$_2$—, —CH=CH—, —N(R)CH$_2$—, —C(R)=N—, —N=C(R)—, —CH(R)O—, —OCH(R)—, —CH(R)S— and —SCH(R)—, or $R^3$ and $R^4$ taken together can form a substituted pyridazinyl ring, $R^5$ and $X^5$ taken together can form a carbonyl, or $X^5$ is a hydrogen atom or taken together with $R^4$ forms a nitrogen-carbon bond, Z is an oxygen atom, a sulfur atom or NR, R is H or alkyl, or a compound of the formula

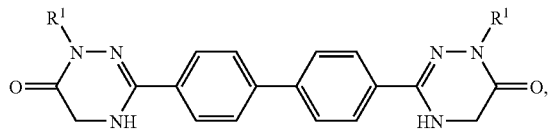

or the agronomically acceptable salts, isomers, tautomers, enantiomers and mixtures thereof, provided that:

when $R^1$ is an aralkyl or a heteroaralkyl, $R^4$ is not cyano, alkylsulfonyl, arylsulfonyl or polyhaloalkyl, when $R^1$ is acetyl and $R^3$ is 2-pyridyl, $R^5$ and $X^5$ taken together can not form a carbonyl, and when $R^3$ is phenyl, methyl or cyclohexyl, $R^1$ is not phenyl, methyl, nitrophenyl, ethoxycarbonyl, benzyl or benzyloxymethyl.

The term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl and the like.

The term "halo" refers to fluoro, chloro, bromo or iodo.

The term "haloalkyl" refers to an alkyl group substituted with one or more halo groups, for example chloromethyl, 2-bromoethyl, 3-iodopropyl, trifluoromethyl, 2,2,2-trifluoroethyl, perfluoropropyl, 8-chlorononyl and the like.

The term "cyanoalkyl" refers to an alkyl group substituted with a cyano group, for example cyanomethyl, 2-cyanoethyl and the like.

The term "alkoxy" includes both branched and straight chain alkyl groups attached to a terminal oxygen atom. Typical alkoxy groups include methoxy, ethoxy, n-propoxy, isopropoxy, tert-butoxy and the like.

The term "alkoxyalkyl" refers to an alkyl group substituted with an alkoxy group, for example isopropoxymethyl.

The term "haloalkoxy" refers to an alkoxy group substituted with one or more halo groups, for example chloromethoxy, trifluoromethoxy, difluoromethoxy, perfluoroisobutoxy and the like.

The term "haloalkoxycarbonyl" refers to an alkoxy group substituted with one or more halo groups attached to a carbonyl group, for example chloromethoxycarbonyl, trifluoromethoxycarbonyl, difluoromethoxy-carbonyl, perfluoroisobutoxycarbonyl and the like.

The term "alkylthio" includes both branched and straight chain alkyl groups attached to a terminal sulfur atom, for example methylthio.

The term "haloalkylthio" refers to an alkylthio group substituted with one or more halo groups, for example trifluoromethylthio.

The term "alkylthioalkyl" refers to a straight chain or branched alkyl as defined hereinbefore substituted with an alkylthio group, for example methylthiomethyl, 3-(isobutylthio)heptyl and the like.

The term "alkylsulfinyl" refers to a sulfinyl moiety substituted with an alkyl group, for example methylsulfinyl, n-propylsulfinyl and the like.

The term "alkylsulfonyl" refers to a sulfonyl moiety substituted with an alkyl group, for example mesyl, n-propylsulfonyl and the like.

The term "alkylamino" refers to an alkyl group attached to a nitrogen atom, for example methylamino, isopropylamino and the like.

The term "dialkylamino" refers to two alkyl groups, which may be the same or different, attached to a nitrogen atom, for example dimethylamino, N-ethyl-N-methylamino and the like.

The term "trialkylsilylalkyl" refers to three alkyl groups, which may be the same or different, attached to a silicon atom which is in turn attached to an alkyl group, for example trimethylsilylmethyl.

The term "alkoxycarbonyl" refers to a straight chain or branched alkoxy attached to a carbonyl group, for example ethoxycarbonyl, methoxycarbonyl and the like.

The term "aryloxy" refers to an unsubstituted or substituted aryl group attached to an oxygen atom, for example phenoxy, 4-(trifluoromethyl)phenoxy, 2-chlorophenoxy, 4-fluoro-1-naphthoxy and the like.

The term "arylthio" refers to an unsubstituted or substituted aryl group attached to a sulfur atom, for example phenylthio, 4-(trifluoromethyl)phenylthio, 2-chlorophenylthio, 4-fluoro-1-naphthylthio and the like.

The term "aryloxycarbonyl" refers to an aryloxy attached to a carbonyl group, for example phenoxycarbonyl and the like.

The term "alkoxyoxalyl" refers to a straight chain or branched alkoxy attached to a oxalyl group, for example ethoxyoxalyl, methoxyoxalyl and the like.

The term "alkylcarbonyloxyalkoxycarbonyl" refers to a straight chain or branched acyloxyalkoxycarbonyl, for example acetoxymethoxycarbonyl and the like.

The term "alkoxycarbonylthio" refers to a straight chain or branched alkoxy attached to a carbonyl group which is in turn attached to a sulfur atom, for example ethoxycarbonylthio, methoxycarbonylthio and the like.

The term "alkylcarbonyl" refers to an alkylketo functionality, for example acetyl, n-butyryl and the like.

The term "arylcarbonyl" refers to an arylketo functionality, for example benzoyl and the like.

The term "alkylcarbonylalkyl" refers to an alkylketoalkyl functionality, for example acetylmethyl and the like.

The term "cycloalkylcarbonyl" refers to an cycloalkylketo functionality, for example cyclopropylcarbonyl and the like.

The term "alkyl(thiocarbonyl)" refers to an alkyl functionality attached to a thiocarbonyl group, for example thioacetyl and the like.

The term "(alkylthio)carbonyl" refers to an alkylthio functionality attached to a carbonyl group, for example methylthiocarbonyl and the like.

The term "aryl(thiocarbonyl)" refers to an aryl functionality attached to a thiocarbonyl group, for example thiobenzoyl and the like.

The term "(arylthio)carbonyl" refers to an arylthio functionality attached to a carbonyl group, for example phenylthiocarbonyl and the like.

The term "alkylthiothiocarbonyl" refers to an allkylthio functionality attached to a thiocarbonyl group, for example propylthiothiocarbonyl and the like.

The term "alkenylthiothiocarbonyl" refers to an alkenylthio functionality attached to a thiocarbonyl group, for example allylthiothiocarbonyl and the like.

The term "alkynylthiothiocarbonyl" refers to an alkynylthio functionality attached to a thiocarbonyl group, for example propargylthiothiocarbonyl and the like.

The term "aryloxythiocarbonyl" refers to an aroxy functionality attached to a thiocarbonyl group, for example phenoxythiocarbonyl and the like.

The term "arylthiothiocarbonyl" refers to an arylthio functionality attached to a thiocarbonyl group, for example phenylthiothiocarbonyl and the like.

The term "alkoxycarbonylalkyl" refers to a straight chain or branched alkyl substituted with an alkoxycarbonyl, for example ethoxycarbonylmethyl, 2-(methoxycarbonyl)propyl and the like.

The term "alkenyl" refers to an ethylenically unsaturated hydrocarbon group, straight or branched chain, having 1 or 2 ethylenic bonds, for example vinyl, allyl, 1-butenyl, 2-butenyl, isopropenyl, 2-pentenyl, allenyl and the like.

The term "haloalkenyl" refers to an alkenyl group substituted with one or more halo groups.

The term "alkenyloxycarbonyl" refers to a straight chain or branched alkenyloxy attached to a carbonyl group, for example allyloxycarbonyl, vinyloxycarbonyl and the like.

The term "alkynyl" refers to an unsaturated hydrocarbon group, straight or branched, having 1 or 2 acetylenic bonds, for example ethynyl, propargyl and the like.

The term "haloalkynyl" refers to an alkynyl group substituted with one or more halo groups.

The term "alkynyloxycarbonyl" refers to a straight chain or branched alkynyloxy attached to a carbonyl group, for example propargyloxycarbonyl and the like.

The term "cycloalkyl" refers to a cyclic aliphatic ring structure, optionally substituted with alkyl, hydroxy and halo, such as cyclopropyl, methylcyclopropyl, cyclobutyl, 2-hydroxycyclopentyl, cyclohexyl, 4-chlorocyclohexyl, cycloheptyl, cyclooctyl and the like.

The term "cycloalkylalkyl" refers to a cycloalkyl group as defined hereinbefore attached to an alkyl group, for example cyclopropylmethyl, cyclohexylethyl and the like.

The term "cycloalkylalkynyl" refers to a cycloalkyl group as defined hereinbefore attached to an alkynyl group, for example cyclopropylpropargyl, 4-cyclopentyl-2-butynyl and the like.

The term "aryl" refers to phenyl or naphthyl which may be optionally substituted. Typical aryl substituents include, but are not limited to, phenyl, 4-chlorophenyl, 4-fluorophenyl, 4-bromophenyl, 3-nitrophenyl, 2-methoxyphenyl, 2-methylphenyl, 3-methylphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, 4-(trifluoromethoxy)phenyl, naphthyl, 2-chloronaphthyl, 2,4-dimethoxyphenyl, 4-(trifluoromethyl)phenyl and 2-iodo-4-methylphenyl.

The term "heteroaryl" refers to a substituted or unsubstituted 5 or 6 membered unsaturated ring containing one, two or three heteroatoms, preferably one or two heteroatoms independently selected from oxygen, nitrogen and sulfur or to a bicyclic unsaturated ring system containing up to 10 atoms including one heteroatom selected from oxygen, nitrogen and sulfur. Examples of heteroaryls include, but are not limited to, 2-, 3- or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzofuranyl and benzothiofuranyl (benzothienyl). The heterocyclic ring may be optionally substituted with up to two substituents such as, but not limited to, alkyl, halo and haloalkyl.

The term "aralkyl" is used to describe a group wherein the alkyl chain can be branched or straight chain with the aryl portion, as defined hereinbefore, forming a terminal portion of the aralkyl moiety. Examples of aralkyl groups include, but are not limited to, optionally substituted benzyl and phenethyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)-ethyl, 2-(2,4-dichlorophenyl)ethyl, 2-(3,5-dimethoxyphenyl)ethyl, 4-(trifluoromethoxy)benzyl and the like.

The term "heteroaralkyl" is used to describe a group wherein the alkyl chain can be branched or straight chain with the heteroaryl portion, as defined hereinbefore, forming a terminal portion of the heteroaralkyl moiety, for example 3-furylmethyl, thenyl (thienylmethyl), furfuryl and the like.

The term "arylsulfonyl" refers to a sulfonyl moiety substituted with an aryl group, for example toluenesulfonyl and the like.

The term "alkylcarbonyloxy" refers to a straight chain or branched alkyl attached to a carbonyl group which is in turn attached to a oxygen atom, for example acetoxy, tert-butylcarbonyloxy and the like.

The term "alkylcarbonylthio" refers to a straight chain or branched alkyl attached to a carbonyl group which is in turn attached to a sulfur atom, for example ethylcarbonylthio, methylcarbonylthio and the like.

The term "alkoxycarbonyloxy" refers to a straight chain or branched alkoxy attached to a carbonyl group which is in turn attached to a oxygen atom, for example ethoxycarbonyloxy, methoxycarbonyloxy and the like.

The term "alkoxycarbonylthio" refers to a straight chain or branched alkoxy attached to a carbonyl group which is in turn attached to a sulfur atom, for example ethoxycarbonylthio, methoxycarbonylthio and the like.

The term "arylcarbonyloxy" refers to an unsubstituted or substituted aryl attached to a carbonyl group which is in turn attached to a oxygen atom, for example benzoyloxy and the like.

The term "arylcarbonylthio" refers to an unsubstituted or substituted aryl attached to a carbonyl group which is in turn attached to a sulfur atom, for example 4-chlorophenylcarbonylthio and the like.

The compounds of formula (I) also embrace the tautomeric forms of the invention, for example

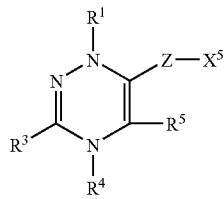

wherein $X^5$ is a hydrogen atom and $R^1$, $R^3$, $R^4$, $R^5$ and Z are as previously defined.

A preferred mode of this first embodiment are compounds of formula (I) wherein $R^1$ is $(C_1-C_{12})$alkyl, halo$(C_1-C_4)$alkyl, $(C_2-C_8)$alkenyl, halo $(C_2-C_8)$alkenyl, $(C_2-C_8)$alkynyl, halo$(C_2-C_8)$alkynyl, cyclo$(C_3-C_7)$alkyl$(C_2-C_8)$alkynyl, $(C_1-C_4)$alkoxy$(C_1-C_4)$alkyl, cyclo$(C_3-C_7)$alkyl, cyclo$(C_3-C_7)$alkyl$(C_1-C_6)$alkyl, tri$(C_1-C_8)$alkylsilyl$(C_1-C_4)$alkyl where the three alkyl groups may be the same or different, $(C_1-C_8)$alkoxycarbonyl, $(C_1-C_8)$alkylcarbonyl, $(C_1-C_8)$alkoxycarbonyl$(C_1-C_4)$alkyl, phenyl or phenyl substituted with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, phen$(C_1-C_4)$alkyl or phen$(C_1-C_4)$alkyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, furyl, thienyl, benzothienyl or benzofuranyl, $R^3$ is $(C_1-C_{12})$alkyl, benzyl, phenethyl or benzyl or phenethyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, phenyl, naphthyl, or phenyl or naphthyl substituted with from one to three substituents independently selected from the group consisting of halo, $(C_1-C_4)$alkyl, halo$(C_1-C_4)$alkyl, halo$(C_1-C_4)$alkoxy, $(C_1-C_4)$alkylthio, halo$(C_1-C_4)$alkylthio, $(C_1-C_4)$ alkylsulfinyl, $(C_1-C_4)$alkylsulfonyl, nitro, cyano, di$(C_1-C_4)$alkylamino wherein the alkyl groups may be the same or different or together with the nitrogen to which they are attached form a 5- or 6-membered heterocyclic ring, quinolinyl, isoquinolinyl, benzofuranyl, benzothienyl, or quinolinyl, isoquinolinyl, benzofuranyl or benzothienyl substituted with one or two substituents independently from halo, $(C_1-C_4)$alkyl, $(C_1-C_4)$alkoxy, halo$(C_1-C_4)$alkoxy, halo$(C_1-C_4)$alkyl, $(C_1-C_4)$alkylthio, nitro and cyano, $R^4$ is a hydrogen atom, $(C_1-C_4)$alkyl, halo$(C_1-C_4)$alkyl, $(C_1-C_4)$alkylcarbonyl, $(C_1-C_4)$alkylcarbonyl$(C_1-C_4)$alkyl, cyclo$(C_3-C_8)$alkyl, cyclo$(C_3-C_8)$alkyl$(C_1-C_4)$alkyl, cyclo $(C_3-C_8)$alkylcarbonyl, $(C_1-C_4)$alkylsulfonyl, $(C_2-C_8)$alkenyl, $(C_2-C_8)$alkenylsulfonyl, phenylsulfonyl$(C_2-C_8)$alkenyl, halo$(C_2-C_8)$alkenyl, $(C_2-C_8)$alkenyl-carbonyl, $(C_2-C_8)$alkynyl, $(C_1-C_4)$alkoxycarbonyl, halo$(C_1-C_4)$alkoxycarbonyl, $(C_1-C_4)$alkoxycarbonyl$(C_1-C_4)$alkyl, $(C_1-C_4)$ alkyl-carbonyloxymethoxycarbonyl, $(C_1-C_4)$ alkoxycarbonylthio, $((C_1-C_4)$-alkylthio)carbonyl, $(C_1-C_4)$ alkylthiocarbonyl, $(C_2-C_8)$alkenyloxy-carbonyl, $(C_2-C_8)$alkenylthiocarbonyl, $(C_2-C_8)$alkynyloxy-carbonyl, $(C_2-C_8)$alkynylthiocarbonyl, $(C_1-C_4)$alkoxyoxalyl, $(C_1-C_4)$alkylcarbonyloxy$(C_1-C_4)$alkoxycarbonyl, phen $(C_1-C_4)$alkyl, benzoyl, phenoxycarbonyl, phenoxythiocarbonyl, phenylthiothio-carbonyl or phen$(C_1-C_4)$alkyl, benzoyl, phenoxycarbonyl, phenoxythiocarbonyl, phenylthiothiocarbonyl substituted on the phenyl ring with from one to two substituents independently selected from halo and $(C_1-C_4)$alkyl, or thenyl or thenyl substituted on the thienyl ring with from one to two substituents independently selected from halo and $(C_1-C_4)$alkyl, $R^5$ is a hydrogen atom, $(C_1-C_4)$alkoxy, $(C_1-C_4)$alkylthio, hydroxy, mercapto, cyano, phenyl or phenyl substituted on the phenyl ring with from one to three substituents independently selected from the group consisting of $(C_1-C_4)$ alkyl, halo, $(C_1-C_4)$alkoxy, halo$(C_1-C_4)$alkyl and halo$(C_1-C_4)$alkoxy, Z is an oxygen atom or a sulfur atom, and $X^5$ is a hydrogen atom or taken together with $R^4$ forms a nitrogen-carbon bond.

A more preferred mode of this embodiment are compounds of formula (I) wherein $R^1$ is $(C_1-C_{10})$alkyl, halo$(C_1-C_{10})$alkyl, $(C_2-C_6)$alkenyl, $(C_2-C_8)$alkynyl, cyclo$(C_3-C_6)$alkyl, $(C_1-C_2)$alkyl, tri$(C_1-C_4)$ alkylsilyl$(C_1-C_2)$alkyl where the three alkyl groups may be the same or different, $R^3$ is phenyl, naphthyl, or phenyl or naphthyl substituted with from one to three substituents independently selected from the group consisting of halo, $(C_1-C_4)$alkyl, halo$(C_1-C_2)$ alkyl and halo$(C_1-C_2)$alkoxy, $R^4$ is a hydrogen atom, $(C_1-C_4)$alkylsulfonyl, $(C_1-C_4)$alkoxycarbonylthio, $(C_2-C_4)$alkenyloxycarbonyl, $(C_2-C_6)$alkynyl, $(C_2-C_4)$alkynyloxycarbonyl or $(C_1-C_4)$alkoxyoxalyl, and $R^5$ is a hydrogen atom, $(C_1-C_4)$alkoxy or $(C_1-C_4)$alkylthio.

An even more preferred mode of this first embodiment are compounds of formula (I) wherein:

$R^1$ is $(C_1-C_{10})$alkyl, halo$(C_1-C_{10})$alkyl, $(C_2-C_8)$alkenyl, halo $(C_2-C_8)$alkenyl, $(C_2-C_8)$alkynyl, cyclo$(C_3-C_6)$alkyl$(C_1-C_2)$alkyl, tri$(C_1-C_4)$alkylsilyl$(C_1-C_2)$alkyl where the three alkyl groups may be the same or different, $R^3$ is dihalosubstitutedphenyl, di$(C_1-C_4)$alkylsubstitutedphenyl, di(halo$(C_1-C_2)$alkyl)substitutedphenyl, monohalomono$(C_1-C_4)$alkyl-substitutedphenyl or monohalomono(halo$(C_1-C_4)$alkyl)substituted-phenyl, $R^4$ and $R^5$ are hydrogen.

A second embodiment of this invention relates to a fungicidal composition comprising a fungicidally effective amount of a compound of the Formula (IA)

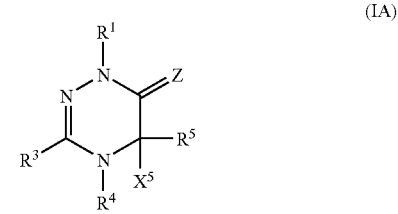

wherein $R^1$ is a hydrogen atom, alkyl, haloalkyl, cyanoalkyl, alkenyl, haloalkenyl, alkynyl, haloalkynyl, cycloalkylalkynyl, alkoxyalkyl, alkylthioalkyl, cycloalkyl, cycloalkylalkyl, trialkylsilylalkyl where the three alkyl groups may be the same or different, alkoxycarbonyl, alkylcarbonyl, alkoxycarbonylalkyl, phenyl, naphthyl, or phenyl or naphthyl substituted with from one to three substituents independently selected from the group consisting of alkyl, halo, nitro, alkoxy, alkylthio, haloalkyl, haloalkylthio and haloalkoxy, phenalkyl or phenalkyl substituted on the phenyl ring with from one to three substituents independently selected from the group consisting of alkyl, halo, alkoxy, haloalkyl and haloalkoxy, pyridyl or pyridyl substituted with from one to two substituents independently selected from the group consisting of alkyl and halo, furyl, thienyl, thenyl or furyl, thienyl or thenyl substituted with halo or alkyl on the furyl or thienyl ring, benzothienyl, benzofuranyl or benzothienyl or benzofuranyl substituted with halo, alkyl or haloalkyl, $R^3$ is alkyl, cycloalkyl, cycloalkylalkyl, phenalkyl or phenalkyl substituted on the phenyl ring with from one to three substituents independently selected from the group consisting of alkyl, halo, alkoxy, haloalkyl and haloalkoxy, aryl selected from phenyl, naphthyl, and phenyl and naphthyl substituted with from one to five substituents independently selected from the group consisting of halo, alkyl, haloalkyl, haloalkoxy, alkylthio, haloalkylthio, alkylsulfinyl, alkylsulfonyl, nitro, cyano, dialkylamino wherein the alkyl groups may be the same or different or together with the nitrogen to which they are attached form a 5- or 6-membered heterocyclic ring, or phenyl and naphthyl substituted with a heteroaryl group selected from furyl, thienyl, quinolinyl, isoquinolinyl, benzofuranyl, benzothienyl, pyridyl, pyridazinyl, pyrimidinyl, pyrazinyl, 1,2,3-thiadiazol-4-yl, 3-(4,5-dihydro-1,2,4-triazin-6-one)yl and oxazol-5-yl, and furyl, thienyl, quinolinyl, isoquinolinyl, benzofuranyl, benzothienyl, pyridyl, pyridazinyl, pyrimidinyl, pyrazinyl, 1,2,3-thiadiazol-4-yl, 3-(4,5-dihydro-1,2,4-triazin-6-one)yl and oxazol-5-yl substituted with one or two substituents independently selected from halo, alkyl, alkoxy, haloalkoxy, haloalkyl, alkylthio, nitro and cyano, phenyl, phenoxy, and phenyl and phenoxy substituted with one or two substituents independently selected from the group consisting of halo, alkyl, alkoxy, haloalkyl, haloalkoxy, alkylthio, nitro and cyano, heteroaryl selected from furyl, thienyl, quinolinyl, isoquinolinyl, benzofuranyl, benzothienyl, pyridyl, pyridazinyl, pyrimidinyl, pyrazinyl, pyrazolyl, 1,2,3-thiadiazol-4-yl, thiazolyl, triazolyl, triazinyl, isoxazolyl and oxazolyl, and furyl, thienyl, pyridyl, pyridazinyl, pyrimidinyl, pyrazinyl, 1,2,3-thiadiazol-4-yl and oxazolyl substituted with one or two substituents independently selected from halo, alkyl, alkoxy, haloalkoxy, haloalkyl, alkylthio, haloalkylthio, nitro and cyano, $R^4$ is a hydrogen atom, haloalkyl, alkylcarbonyl, alkylcarbonylalkyl, cycloalkyl, cycloalkylalkyl, cycloalkylcarbonyl, alkylsulfonyl, alkoxy, alkylthio, amino, alkylamino, dialkylamino wherein the alkyl groups may be the same or different or together with the nitrogen to which they are attached form a 5- or 6-membered heterocyclic ring, cyano, alkenyl, alkenylsulfonyl, haloalkenyl, alkenylcarbonyl, alkynyl, haloalkynyl, alkoxycarbonyl, haloalkoxycarbonyl, alkoxycarbonylalkyl, alkoxycarbonylthio, (alkylthio)carbonyl, alkyl(thiocarbonyl), alkylthiothiocarbonyl, alkenyloxycarbonyl, alkenylthiothiocarbonyl, alkynyloxycarbonyl, alkynylthiothio-carbonyl, alkoxyoxalyl, alkylcarbonyloxyalkoxycarbonyl, aralkyl, arylcarbonyl, arylsulfonyl, arylsulfonylalkenyl, aryloxycarbonyl, aryloxythiocarbonyl, arylthiothiocarbonyl or aralkyl, arylcarbonyl, arylsulfonyl, arylsulfonylalkenyl, aryloxycarbonyl, aryloxythio-carbonyl, arylthiothiocarbonyl substituted on an aromatic ring with from one to two substituents independently selected from halo and alkyl, $R^5$ is a hydrogen atom, alkyl, haloalkyl, alkylcarbonyl, alkylcarbonylalkyl, formyl, alkoxy, alkoxycarbonyl, alkoxycarbonyloxy, alkylcarbonyloxy, alkoxycarbonylthio, alkylcarbonylthio, alkylthio, hydroxy, mercapto, alkenyl, alkynyl, cyano, amino, alkylamino, dialkylamino wherein the alkyl groups may be the same or different or together with the nitrogen to which they are attached form a 5- or 6-membered heterocyclic ring, aryl, aralkyl, aryloxy, arylthio, arylcarbonyloxy, arylcarbonylthio, or aryl, aralkyl, aryloxy, arylthio, arylcarbonyloxy, arylcarbonylthio substituted on the aryl ring with from one to three substituents independently selected from the group consisting of alkyl, halo, alkoxy, haloalkyl, haloalkoxy, amino, alkylamino and dialkylamino wherein the alkyl groups may be the same or different or together with the nitrogen to which they are attached form a 5- or 6-membered heterocyclic ring, or $R^4$ can form a fused ring to the $R^3$ substituent when the $R^3$ substituent is aryl or heteroaryl wherein $R^4$ is selected from —CH(R)—, —O—, —S—, —N(R)—, —C(=O)—, —O(C=O)—, —C(=O)O—, —CH$_2$CH$_2$—, —CH=CH—, —N(R)CH$_2$—, —C(R)=N—, —N=C(R)—, —CH(R)O—, —OCH(R)—, —CH(R)S— and —SCH(R)—, or $R^3$ and $R^4$ taken together can form a substituted pyridazinyl ring, $R^5$ and $X^5$ taken together can form a carbonyl, or $X^5$ is a hydrogen atom or taken together with $R^4$ forms a nitrogen-carbon bond, Z is an oxygen atom, a sulfur atom or NR, R is H or alkyl, or a compound of the formula

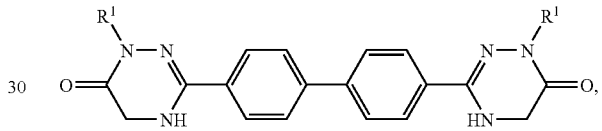

or the agronomically acceptable salts, isomers, tautomers, enantiomers and mixtures thereof, and an agronomically acceptable carrier.

A preferred mode of this second embodiment are fungicidal compositions comprising a compound of formula (IA) wherein $R^1$ is $(C_1-C_{12})$alkyl, halo$(C_1-C_4)$alkyl, $(C_2-C_8)$alkenyl, halo$(C_2-C_8)$alkenyl, $(C_2-C_8)$alkynyl, halo$(C_2-C_8)$alkynyl, cyclo$(C_3-C_7)$alkyl$(C_2-C_8)$alkynyl, $(C_1-C_4)$alkoxy$(C_1-C_4)$alkyl, cyclo$(C_3-C_7)$alkyl, cyclo$(C_3-C_7)$alkyl$(C_1-C_6)$alkyl, tri$(C_1-C_8)$alkylsilyl$(C_1-C_4)$alkyl where the three alkyl groups may be the same or different, $(C_1-C_8)$alkoxycarbonyl, $(C_1-C_8)$alkylcarbonyl, $(C_1-C_8)$alkoxycarbonyl$(C_1-C_4)$alkyl, phenyl or phenyl substituted with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, phen$(C_1-C_4)$alkyl or phen$(C_1-C_4)$alkyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, furyl, thienyl, benzothienyl or benzofuranyl, $R^3$ is $(C_1-C_{12})$alkyl, benzyl, phenethyl or benzyl or phenethyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, phenyl, naphthyl, or phenyl or naphthyl substituted with from one to three substituents independently selected from the group consisting of halo, $(C_1-C_4)$alkyl, halo$(C_1-C_4)$alkyl, halo$(C_1-C_4)$alkoxy, $(C_1-C_4)$alkylthio, halo$(C_1-C_4)$alkylthio, $(C_1-C_4)$alkylsulfinyl, $(C_1-C_4)$alkylsulfonyl, nitro, cyano, di$(C_1-C_4)$alkylamino wherein the alkyl groups may be the same or different or together with the nitrogen to which they are attached form a 5- or 6-membered heterocyclic ring, quinolinyl, isoquinolinyl, benzofuranyl, benzothienyl, or quinolinyl, isoquinolinyl, benzofuranyl or benzothienyl substituted with one or two substituents independently selected from halo, $(C_1-C_4)$alkyl, $(C_1-C_4)$alkoxy, halo$(C_1-C_4)$alkoxy, halo$(C_1-C_4)$alkyl, $(C_1-C_4)$alkylthio, nitro and cyano, $R^4$ is a hydrogen atom, halo$(C_1-C_4)$alkyl, $(C_1-C_4)$alkylcarbonyl, $(C_1-C_4)$alkylcarbonyl$(C_1-C_4)$alkyl, cyclo$(C_3$-CB)alkyl, cyclo$(C_3-C_8)$alkyl$(C_1-C_4)$alkyl, cyclo$(C_3-C_8)$alkylcarbonyl, $(C_1-C_4)$alkylsulfonyl, $(C_2-C_8)$alkenyl, $(C_2-C_8)$alkenylsulfonyl, phenylsulfonyl$(C_2-C_8)$alkenyl, halo$(C_2-C_8)$alkenyl, $(C_2-C_8)$alkenylcarbonyl, $(C_2-C_8)$alkynyl, $(C_1-C_4)$alkoxycarbonyl, halo$(C_1-C_4)$alkoxycarbonyl, $(C_1-C_4)$alkoxycarbonyl$(C_1-C_4)$alkyl, $(C_1-C_4)$alkylcarbonyloxymethoxy-carbonyl, $(C_1-C_4)$alkoxycarbonylthio, $((C_1-C_4)$alkylthio)carbonyl, $(C_1-C_4)$alkylthiothiocarbonyl, $(C_2-C_8)$alkenyloxycarbonyl, $(C_2-C_8)$alkenyl-thiothiocarbonyl, $(C_2-C_8)$alkynyloxycarbonyl, $(C_2-C_8)$alkynyl-thiothiocarbonyl, $(C_1-C_4)$alkoxyoxalyl, $(C_1-C_4)$alkylcarbonyloxy$(C_1-C_4)$alkoxycarbonyl, phen$(C_1-C_4)$alkyl, benzoyl, phenoxycarbonyl, phenoxythiocarbonyl, phenylthiothiocarbonyl or phen$(C_1-C_4)$alkyl, benzoyl, phenoxycarbonyl, phenoxythiocarbonyl, phenylthiothio-carbonyl substituted on the phenyl ring with from one to two substituents independently selected from halo and $(C_1-C_4)$alkyl, $R^5$ is a hydrogen atom, $(C_1-C_4)$alkoxy, $(C_1-C_4)$alkylthio, hydroxy, mercapto, cyano, phenyl or phenyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, Z is an oxygen atom or a sulfur atom, and $X^5$ is a hydrogen atom or taken together with $R^4$ forms a nitrogen-carbon bond.

A more preferred mode of this second embodiment are fungicidal compositions comprising a compound of formula (IA) wherein $R^1$ is $(C_1-C_{10})$alkyl, halo$(C_1-C_4)$alkyl, $(C_2-C_6)$alkenyl, $(C_2-C_6)$alkynyl, cyclo$(C_3-C_6)$alkyl$(C_1-C_2)$alkyl, tri$(C_1-C_4)$alkylsilyl$(C_1-C_2)$alkyl where the three alkyl groups may be the same or different, $R^3$ is phenyl, naphthyl, or phenyl or naphthyl substituted with from one to three substituents independently selected from the group consisting of halo, $(C_1-C_4)$alkyl, halo$(C_1-C_2)$alkyl and halo$(C_1-C_2)$alkoxy, $R^4$ is a hydrogen atom, $(C_1-C_4)$alkylsulfonyl, $(C_1-C_4)$alkoxycarbonylthio, $(C_2-C_4)$alkenyloxycarbonyl, $(C_2-C_6)$alkynyl, $(C_2-C_4)$alkynyloxycarbonyl or $(C_1-C_4)$alkoxyoxalyl, and $R^5$ is a hydrogen atom, $(C_1-C_4)$alkoxy or $(C_1-C_4)$alkylthio.

An even more preferred mode of this second embodiment are fungicidal compositions comprising a compound of formula (IA) wherein $R^1$ is $(C_1-C_{10})$alkyl, halo$(C_1-C_{10})$alkyl, $(C_2-C_8)$alkenyl, halo$(C_2-C_8)$alkenyl, $(C_2-C_8)$alkynyl, cyclo$(C_3-C_6)$alkyl$(C_1-C_2)$alkyl, tri$(C_1-C_4)$alkylsilyl$(C_1-C_2)$alkyl where the three alkyl groups may be the same or different, $R^3$ is dihalosubstitutedphenyl, di$(C_1-C_4)$alkylsubstitutedphenyl, di(halo-$(C_1-C_2)$alkyl)substitutedphenyl, monohalomono$(C_1-C_4)$alkyl-substituted or monohalomono(halo$(C_1-C_4)$alkyl)substitutedphenyl, $R^4$ and $R^5$ are hydrogen.

A third embodiment of this invention relates to an insecticidal composition comprising a insecticidally effective amount of a compound of the formula (IB)

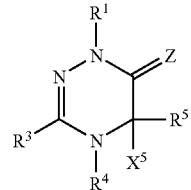

(IB)

wherein $R^1$ is a hydrogen atom, alkyl, haloalkyl, cyanoalkyl, alkenyl, haloalkenyl, alkynyl, haloalkynyl, cycloalkylalkynyl, alkylthioalkyl, cycloalkyl, cycloalkylalkyl, trialkylsilylalkyl where the three alkyl groups may be the same or different, alkylcarbonyl, phenyl, naphthyl, or phenyl or naphthyl substituted with from one to three substituents independently selected from the group consisting of alkyl, halo, alkoxy, haloalkyl and haloalkoxy, phenalkyl or phenalkyl substituted on the phenyl ring with from one to three substituents independently selected from the group consisting of alkyl, halo, alkoxy, haloalkyl and haloalkoxy, furyl, thienyl, thenyl or furyl, thienyl or thenyl substituted with halo on the furyl or thienyl ring, benzothienyl or benzofuranyl, $R^3$ is alkyl, cycloalkyl, cycloalkylalkyl, phenalkyl or phenalkyl substituted on the phenyl ring with from one to three substituents independently selected from the group consisting of alkyl, halo, alkoxy, haloalkyl and haloalkoxy, aryl selected from phenyl and phenyl substituted with from one to five substituents independently selected from the group consisting of halo, alkyl, haloalkyl, haloalkoxy, alkylsulfinyl, alkylsulfonyl, nitro, cyano, dialkylamino wherein the alkyl groups may be the same or different or together with the nitrogen to which they are attached form a 5- or 6-membered heterocyclic ring, heteroaryl selected from furyl, quinolinyl, isoquinolinyl, benzofuranyl, benzothienyl and pyridyl, and benzofuranyl, benzothienyl and pyridyl substituted with one or two substituents independently selected from halo, alkyl, alkoxy, haloalkoxy, haloalkyl, alkylthio, nitro and cyano, $R^4$ is a hydrogen atom, alkyl, alkylcarbonyl, alkoxy, alkylthio, alkylamino, cyano, alkenyl, alkynyl, haloalkynyl, haloalkoxy-carbonyl, alkoxycarbonylthio, alkenyloxycarbonyl, alkynyloxy-carbonyl, alkoxyoxalyl, alkylcarbonyl, alkylcarbonyloxy-alkoxycarbonyl, arylcarbonyl, arylsulfonyl, aryloxythiocarbonyl, or arylcarbonyl, arylsulfonyl, aryloxythiocarbonyl substituted on the aryl ring with from one to two substituents independently selected from halo and alkyl, or thenyl or thenyl substituted on the thienyl ring with from one to two substituents independently selected from halo and alkyl, $R^5$ is a hydrogen atom, alkyl, haloalkyl, alkylcarbonyl, formyl, alkoxy, alkoxycarbonyl, alkoxycarbonyloxy, alkylcarbonyloxy, alkoxy-carbonylthio, alkylcarbonylthio, alkylthio, mercapto, alkenyl, alkynyl, cyano, dialkylamino, aryl, aralkyl, aryloxy, arylthio, arylcarbonyloxy, arylcarbonylthio or aryl, aralkyl, aryloxy, arylthio, arylcarbonyloxy or arylcarbonylthio substituted on the aryl ring with from one to three substituents independently selected from the group consisting of alkyl, halo, alkoxy, haloalkyl and haloalkoxy, $X^5$ is a hydrogen atom or taken together with $R^4$ forms a nitrogen-carbon bond, Z is an oxygen atom, or a compound of the formula

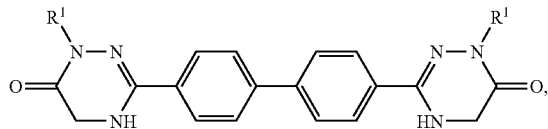

or the agronomically acceptable salts, isomers, tautomers, enantiomers and mixtures thereof and an agronomically acceptable carrier, provided that when $R^1$ is an aralkyl or a heteroaralkyl, $R^4$ is not cyano, alkylsulfonyl, arylsulfonyl or polyhaloalkyl.

A preferred mode of this third embodiment are insecticidal compositions comprising a compound of formula (IB) wherein $R^1$ is a hydrogen atom, $(C_1-C_4)$alkyl, halo$(C_1-C_4)$alkyl, $(C_2-C_6)$alkenyl, halo$(C_2-C_8)$alkenyl, $(C_2-C_8)$alkynyl, halo$(C_2-C_8)$alkynyl, cyclo$(C_3-C_7)$alkyl$(C_2-C_8)$alkynyl, cyclo$(C_3-C_7)$alkyl, cyclo$(C_3-C_7)$alkyl$(C_1-C_6)$alkyl, tri$(C_1-C_8)$alkylsilyl$(C_1-C_4)$alkyl where the three alkyl groups may be the same or different, $(C_1-C_8)$alkylcarbonyl, phenyl or phenyl substituted with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, phen$(C_1-C_4)$alkyl or phen$(C_1-C_4)$alkyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, furyl, thienyl, benzothienyl or benzofuranyl, $R^3$ is $(C_1-C_{12})$alkyl, benzyl, phenethyl or benzyl or phenethyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy, phenyl or phenyl substituted with from one to three substituents independently selected from the group consisting of halo, $(C_1-C_4)$alkyl, halo$(C_1-C_4)$alkyl, halo$(C_1-C_4)$alkoxy, $(C_1-C_4)$alkylsulfinyl, $(C_1-C_4)$alkylsulfonyl, nitro, cyano, di$(C_1-C_4)$alkylamino wherein the alkyl groups may be the same or different or together with the nitrogen to which they are attached form a 5- or 6-membered heterocyclic ring, benzofuranyl, benzothienyl or benzofuranyl or benzothienyl substituted with one or two substituents independently selected from halo, $(C_1-C_4)$alkyl, $(C_1-C_4)$alkoxy, halo$(C_1-C_4)$alkoxy, halo$(C_1-C_4)$alkyl, $(C_1-C_4)$alkylthio, nitro and cyano, $R^4$ is a hydrogen atom, $(C_1-C_4)$alkylcarbonyl, $(C_1-C_4)$alkylsulfonyl, $(C_2-C_8)$alkynyl, halo$(C_2-C_8)$alkynyl, halo$(C_1-C_4)$alkoxycarbonyl, $(C_1-C_4)$alkylcarbonyloxymethoxycarbonyl, $(C_1-C_4)$alkoxycarbonylthio, $(C_2-C_8)$alkenyloxycarbonyl, $(C_2-C_8)$alkynyloxycarbonyl or $(C_1-C_4)$alkoxyoxalyl, and $R^5$ is a hydrogen atom, $(C_1-C_4)$alkylthio, $(C_1-C_4)$alkoxy, cyano, phenyl or phenyl substituted on the phenyl ring with from one to three substituents independently selected from the group consisting of $(C_1-C_4)$alkyl, halo, $(C_1-C_4)$alkoxy, halo$(C_1-C_4)$alkyl and halo$(C_1-C_4)$alkoxy.

A more preferred mode of this third embodiment are insecticidal compositions comprising a compound of formula (IB) wherein $R^1$ is $(C_1-C_{10})$alkyl, halo$(C_1-C_{10})$alkyl, $(C_2-C_8)$alkynyl, cyclo$(C_3-C_6)$alkyl$(C_1-C_2)$alkyl, tri$(C_1-C_4)$alkylsilyl$(C_1-C_2)$alkyl where the three alkyl groups may be the same or different, $R^3$ is phenyl or phenyl substituted with from one to three substituents independently selected from the group consisting of halo, $(C_1-C_4)$alkyl, halo$(C_1-C_2)$alkyl and halo$(C_1-C_2)$alkoxy, or benzothienyl substituted with one or two substituents independently selected from halo, $(C_1-C_4)$alkyl, $(C_1-C_4)$alkoxy, halo$(C_1-C_4)$alkoxy, halo$(C_1-C_4)$alkyl, $(C_1-C_4)$alkylthio, nitro and cyano, $R^4$ is a hydrogen atom, $(C_1-C_4)$alkylsulfonyl, $(C_1-C_4)$alkoxycarbonylthio, $(C_2-C_4)$alkenyloxycarbonyl, $(C_2-C_4)$alkynyloxycarbonyl or $(C_1-C_4)$alkoxyoxalyl, and $R^5$ is a hydrogen atom, $(C_1-C_4)$alkoxy or $(C_1-C_4)$alkylthio.

A fourth embodiment of the present invention relates to a method of controlling a fungus comprising applying a fungicidally effective amount of a fungicidal composition comprising a compound of formula (IA) to the fungus, to the locus of the fungus or to the growth medium of said fungus.

A fifth embodiment of the present invention relates to a method of controlling an insect comprising applying an insecticidally effective amount of an insecticidal composition comprising a compound of formula (IB) to the insect, to the locus of the insect or to the growth medium of said insect.

The compounds of this invention can be made by the using methods A-K:

Method A:

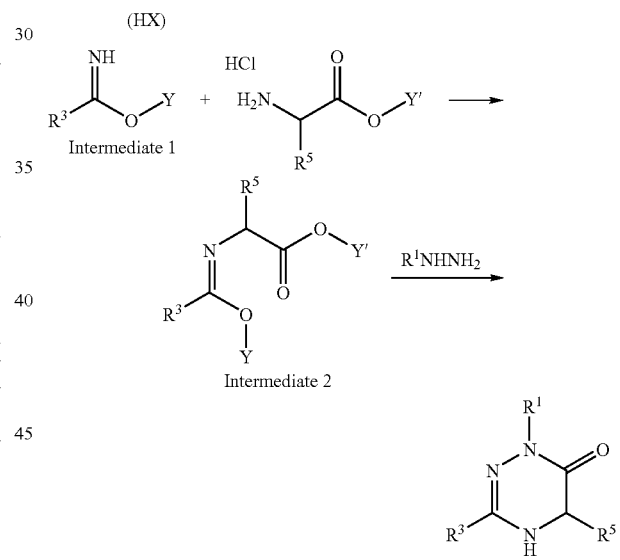

The imidic esters (intermediate 1) can be formed by standard methods (for example, Neilson, D. G. in "The Chemistry of Amidines and Imidates", (S. Patai, ed.), Wiley Publishing Co., New York, N.Y. (1975) pp. 385-413 and references therein; Kiessling, A. J and McClure, C. K., *Synthetic Communications* 27(5), 923-927 (1997); and Schafer, F. C and Peters, G. A., *J. Org. Chem.* (1961) 26, 412). In the above equation, X is a counter ion such as chloride or bromide, and Y is alkyl or aryl. The imidic esters may be neutral, or they may be salts; in the case of salts, roughly one equivalent of base is added to the reaction. The reactions can be run in methylene chloride, dioxane with a small amount of ethanol, alcohol solvents such as ethanol, methanol or isopropanol, or preferably in methylene chloride with 5% ethanol. The reactions can be run at room temperature or heated. The product intermediate 2 is reacted with a hydrazine to give the desired product. Solvents for this reaction include tetrahydrofuran, dioxane, or preferably an alcohol such as ethanol, propanol, etc.

Alternatively, intermediate 2 can be prepared from an acylated amino acid as shown, using triethyloxonium tetrafluoroborate (or related derivatives) or methyl triflate, as shown for method B.

Method B:

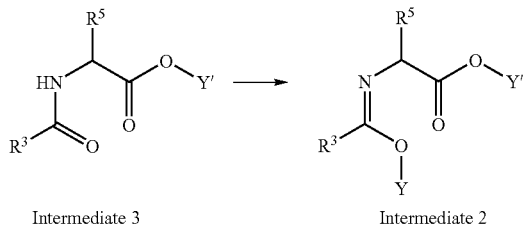

Method C:

Solid phase synthesis can be used to make compound of this invention.

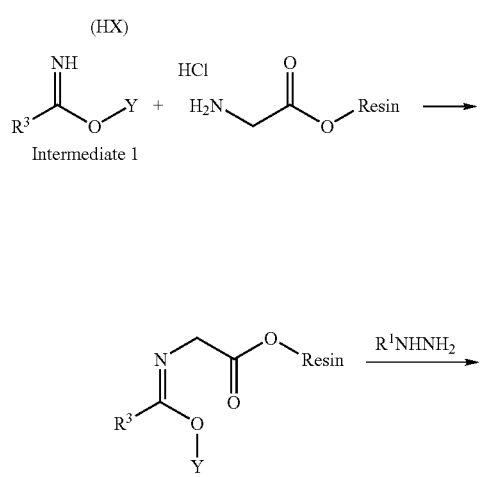

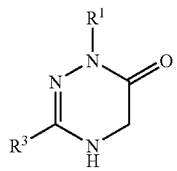

Method D:

Compounds described in this invention can be made from acylated amino acids by the reaction shown in the scheme below. The preparation of the thioamide was carried out with phosphorous pentasulfide in toluene at 90° C., however, other reagents such as Lawesson's reagent and other solvents can be used. The alkylation of the thioamide was carried out using methyl iodide in methanol with sodium methoxide or in acetone with potassium carbonate as the base. The reaction of the intermediates with hydrazines is preferably run in alcohol solvents.

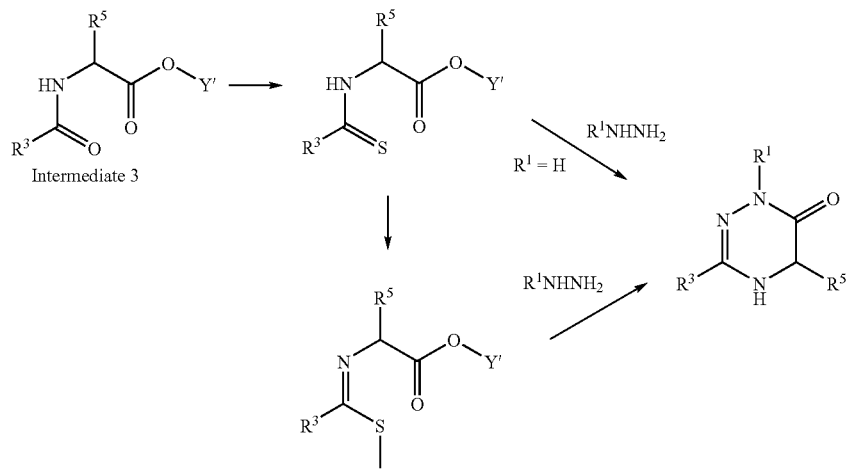

Method E:

The dihydrotriazinones may be oxidized to the triazinones by using 2,3-dichloro-5,6-dicyano-1,4-benzoquinone (DDQ). The reaction is preferably run in ethyl acetate, although other solvents, such as aromatic hydrocarbons, can be used.

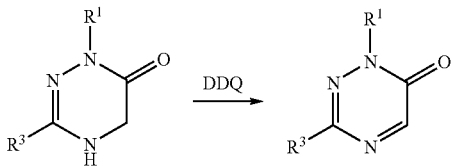

Occasionally, oxidation of a dihydrotriazinone to a triazinone occurs spontaneously during a reaction or during purification.

Method F:

Compounds can be alkylated at $N^1$ using a strong base such as sodium hydride or potassium t-butoxide in solvents such as DMF or THF. $R^1X$ is any alkylating agent.

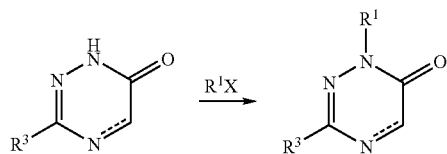

Method G:

$N^4$ can be derivatized using a strong base such as sodium hydride or potassium t-butoxide and an electrophile. For reactive electrophiles such as di-tert-butyl dicarbonate, either no base or a mild base, such as triethylamine, is required.

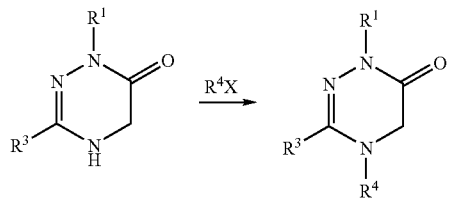

Method H:

The carbonyl can be converted to a thiocarbonyl using phosphorus pentasulfide in toluene. Both other reagents, such as Lawesson's reagent, and other solvents could be used.

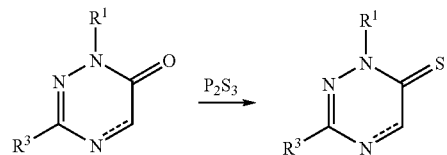

Method I:

The 1,2,4-triazin-6-ones can react with nucleophiles such as alcohols or thiols to form 5-substituted derivatives.

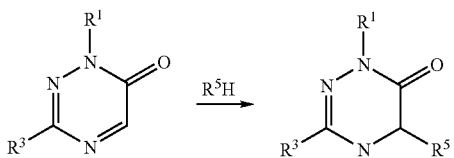

Method J:

1,2,4-Triazin-5,6-diones can be prepared by from the amidrazone by reaction with oxalyl chloride or diethyl oxalate.

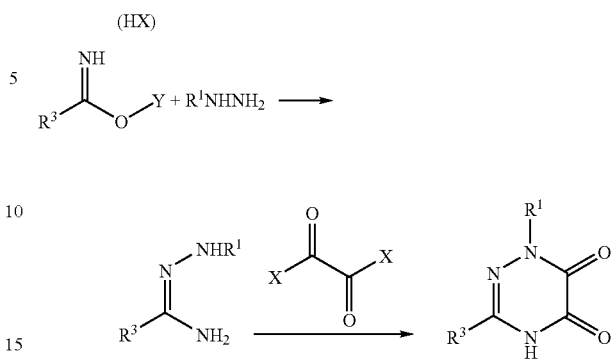

Method K:

A Grignard reagent can be added to a 1,2,4-triazin-6-one in a suitable solvent, such as ether or THF to give a 5-substituted dihydrotriazinone.

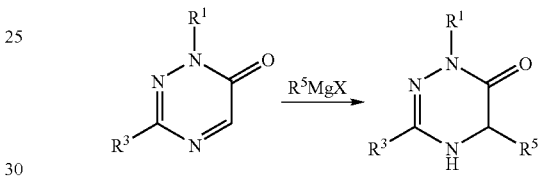

EXAMPLES DEMONSTRATING THE METHODS

All reactions were run under a blanket of nitrogen. Chromatographic purifications were carried out using silica gel under air or preferably nitrogen pressure, or under reduced pressure, or by reverse phase liquid chromatography (LC).

Method A:

Preparation of 1-(2,2,2-trifluoroethyl)-3-(3-chloro-4-fluorophenyl)-4,5-dihydro-1,2,4-triazin-6-one (Compound 1)

A slurry of 17.7 grams of O-ethyl 3-chloro-4-fluorobenzimidate hydrochloride (74 mmol), 12.6 grams of ethyl glycine hydrochloride (90 mmol), 140 mL of methylene chloride and 7 ml of dry ethanol was prepared. After ten minutes of stirring 9.60 grams of triethylamine (95 mmol) was added over three minutes. No significant exotherm resulted. The reaction was allowed to stir overnight at room temperature. The reaction was diluted with 100 ml of methylene chloride and washed with two 70 ml portions of water. The organic phase was dried and concentrated under reduced pressure to yield 15.9 grams of O-ethyl N-(ethyl 2-acetate)3-chloro-4-fluorobenzimidate as a dark amber oil. The material was reacted without further purification.

2,2,2-Trifluroethylhydrazine (2.17 grams, 70% solution in water, 13.3 mmol) was added dropwise over two minutes to a solution of 3.82 grams O-ethyl N-(ethyl 2-acetate)-3-chloro-4-fluorobenzimidate (13.2 mmol) in 25 ml of dry ethanol. The reaction was allowed to stir overnight at room temperature. The reaction was refluxed for one hour, allowed to cool, diluted with 10 ml of water. The solid was collected on a Buchner funnel, rinsed with several ml of methanol, and dried. The yield was 1.3 grams of 1-(2,2,2-trifluoroethyl)-3-(3-chloro-4-fluorophenyl)-4,5-dihydro-1,2,4-triazin-6-one.

Method B:

Preparation of 1-butyl-3-(2,4-dichlorophenyl)-4,5-dihydro-1,2,4-triazin-6-one (Compound 2)

Ethyl 2,4-dichlorobenzoylglycine (6.28 grams, 22.7 mmol) was dissolved in 40 mL of methylene chloride. Methyl triflate (4.89 grams, 30 mmol) was added at once and the reaction was allowed to stir at room temperature for 3 days. The reaction was concentrated under reduced pressure. Then 30 mL of toluene was added and removed under reduced pressure to yield 10.6 grams of O-methyl-N-(ethyl 2-acetate)-2,4-dichlorobenzimidate trifluoromethanesulfonate as a clear liquid.

A solution of 5.3 grams of O-methyl-N-(ethyl 2-acetate)-2,4-dichlorobenzimidate trifluoromethanesulfonate (12 mmol) in 30 mL of dry ethanol was chilled in ice water bath. n-Butylhydrazine oxalate (2.05 grams, 11.5 mmol) was added, then 5.1 grams of triethylamine (50 mmol) was added in small portions over five minutes. The reaction was allowed to warm to room temperature for one hour and then heated to reflux overnight. The reaction was concentrated under reduced pressure and partitioned between 125 mL of ethyl acetate and 70 mL of water. The organic phase was concentrated under reduced pressure and chromatographed with ethyl acetate/hexanes. The yield was 2.0 grams of 1-butyl-3-(2,4-dichlorophenyl)-4,5-dihydro-1,2,4-triazin-6-one as an oil.

Method C:

Preparation of 1-Butyl-3-(4-phenoxyphenyl)-4,5-dihydro-1,2,4-triazin-6-one (Compound 3)

Preparation of the FMOC-gly-Wang Resin

Wang resin (70 g, 119 mmol, PL-Wang, Polymer Labs, 1.7 mmol/g.) was swollen in 550 mL of methylene chloride and 100 mL of DMF and stirred for 30 min with an overhead stirrer. 71 g (238 mmol) of FMOC-glycine were added, followed by 60 g (476 mmol) of diisopropylcarbodiimide and 2.4 g (19.7 mmol) of 4-dimethylaminopyridine. The reaction was stirred for 3.5 h at room temperature, the resin was filtered, washed with alternating methanol and methylene chloride and dried in a vacuum oven.

Preparation of the Dihydrotriazinone

FMOC-gly-Wang resin (1.3 g) was conditioned with DMF (2×6 ml) and then treated with piperidine (20% in DMF, 5 ml) for 20 min. The resin was filtered and washed with DMF (×2), methylene chloride (×2) and methanol (×2). Then 874 mg (3 mmol) of ethyl 4-phenyloxybenzimidate hydrochloride was added as a solid, followed by 5 mL methylene chloride and 1.7 mL of a solution of triethylamine in methanol (at 82 mg triethylamine/mL). The resin was shaken for 4 h at room temperature and then filtered and washed alternatively with methylene chloride and methanol. The resin was conditioned with methylene chloride and 532 mg (3 mmol) of butylhydrazine oxalate were added, followed by 581 mg of triethylamine and 1.5 ml of ethanol. The reaction was shaken at room temperature for 48 h, and the resin was filtered and washed with methylene chloride (×3). The collected filtrates were evaporated to dryness and the crude material is purified by low pressure chromatography on silica. Evaporation of the solvent gave 159 mg of a yellow solid.

Method D:

Preparation of 1-(2,2,2-trifluoroethyl)-3-(4-chlorophenyl)-4,5-dihydro-1,2,4-triazin-6-one (Compound 4)

To a slurry of 4.54 g of 4-chlorobenzoyl methyl glycine (20 mmol) in 60 ml of toluene under an atmosphere of nitrogen was added 0.89 g (20 mmol) of phosphorus pentasulfide. The reaction was heated to 90° C. for 3 hours. An additional 0.18 g of phosphorus pentasulfide was added, and the reaction was heated for an additional 1 hour, then cooled to room temperature. The product was filtered, the slurry was washed with ethyl acetate, and the combined filtrates were run through silica gel on Gelite, then stripped. The product was chromatographed on a silica gel column to give 3.3 g (68% yield) of 4-chlorothiobenzoyl methylglycine, melting point 72-73° C.

A solution of 2.9 g 4-chlorothiobenzoyl methylglycine (11.9 mmol) in 20 ml of methanol under an atmosphere of nitrogen was cooled in an ice bath and treated with 0.67 g of sodium methoxide (12.4 mmol). Excess methyl iodide (5 g, 35 mmol) was added, and the reaction was stirred. An additional 1.15 g of sodium methoxide was added in two portions, and the reaction was allowed to warm to room temperature. Water was added, and the reaction mixture was extracted with ethyl acetate. The organic phase was washed with brine, dried over magnesium sulfate, filtered and stripped to give 2.87 g of N-2-acetic acid methyl ester-4-chlorophenyl (methylthio) imino ether.

A mixture of 1.63 g (6.3 mmol) of N-2-acetic acid methyl ester-4-chlorophenyl (methylthio)imino ether and 2.26 g of 2,2,2-trifluoroethylhydrazine (70%, 13.8 mmol) in ethanol was stirred overnight at room temperature, then heated to reflux. The reaction was cooled, and the ethanol was stripped. The residue was extracted with ethyl acetate.

Column chromatography gave 0.33 g of 1-(2,2,2-trifluoroethyl)-3-(4-chlorophenyl)-4,5-dihydro-1,2,4-triazin-6-one, melting point 178-180° C.

Preparation of 3-(4-Chlorophenyl)-4,5-dihydro-1,2,4-triazin-6-one (Compound 5)

4-Chlorothiobenzoyl methyl glycine (4.87 g, 20 mmol), 2.2 g of hydrazine hydrate (44 mmol) and 20 mL of methanol were combined and stirred at room temperature overnight, then heated to reflux. The reaction mixture was cooled and filtered. The solids were washed, then dried, giving 3-(4-chlorophenyl)-4,5-dihydro-1,2,4-triazin-6-one.

Preparation of 1-t-Butyl-3-(4-chlorophenyl)-4,5-dihydro-1,2,4-triazin-6-one (Compound 6)

A solution of 7.2 grams of crude of N-2-acetic acid ethyl ester-4-chlorophenyl (methylthio)imino ether (28 mmol) in 40 mL of dry ethanol was cooled in an ice bath and treated with 5.3 grams of t-butyl hydrazine hydrate (74 mmol). The reaction was allowed to stir overnight at room temperature, then refluxed for 7.5 hours and allowed to cool. One half of the reaction mixture was concentrated under reduced pressure, then dissolved in 20 ml of xylenes. The reaction was heated to 120° C.-130° C. for six hours. The reaction was diluted with 100 mL of ethyl acetate and washed with 60 mL of water, dried and concentrated under reduced pressure. After chromatography 50 mg of 1-t-butyl-3-(4-chlorophenyl)-4,5-dihydro-1,2,4-triazin-6-one was obtained.

Method E:

Preparation of 1-(2,2,2-trifluoroethyl)-3-phenyl-1,2,4-triazin-6-one (Compound 7)

A mixture of 0.51 g of 1-(2,2,2-trifluoroethyl)-3-phenyl-4,5-dihydro-1,2,4-triazin-6-one (2.0 mmol) and 0.48 g of DDQ (2.1 mmol) in 20 mL of ethyl acetate was stirred at room temperature overnight, then heated to 70° C. for 2 hours. The reaction mixture was cooled and washed with aqueous potassium carbonate, water (2 times) and brine, dried over magnesium sulfate, filtered and stripped. The product was dissolved in ethyl acetate/methylene chloride and treated with silica gel, then filtered through silica gel over Celite to give 0.40 g of 1-(2,2,2-trifluoroethyl)-3-phenyl-1,2,4-triazin-6-one, melting point 129-131° C.

Method F:

Preparation of 1-(2-pentynyl)-3-(4-chlorophenyl)-1,2,4-triazin-6-one (Compound 8)

A mixture of 2.00 g of 3-(4-chlorophenyl)-4,5-dihydro-1,2,4-triazin-6-one (9.6 mmol) and 2.28 g of DDQ in 120 mL of ethyl acetate was stirred at room temperature overnight, then heated to reflux for 3 hours. The reaction mixture was cooled and filtered to give 0.4 g of a tan solid which dried in a vacuum oven and used without further purification.

The 0.4 g of 3-(4-chlorophenyl)-1,2,4-triazin-6-one (1.9 mmol) was placed in 10 mL of DMF and cooled in an ice bath. Sodium hydride (NaH) (0.8 g of 60% dispersion, 2 mmol) was added, and the reaction mixture was held for 15 minutes. Excess 1-chloro-2-pentyne was added, the bath was removed, and the reaction mixture was allowed to warm to room temperature. Water and ethyl acetate were added. The organic phase was washed with water and brine, dried over magnesium sulfate, filtered and stripped. The crude product was chromatographed on silica gel to give 0.05 g of 1-(2-pentynyl)-3-(4-chlorophenyl)-1,2,4-triazin-6-one.

Preparation of 1-Cyclopropylmethyl-3-(3,4-dichlorophenyl)-4,5-dihydro-1,2,4-triazin-6-one (Compound 9)

To a solution of 0.82 grams of 3-(3,4-dichlorophenyl)-4,5-dihydro-1,2,4-triazin-6-one (2.9 mmol), prepared by method A, in 10 mL of N,N-dimethylformamide (DMF) was added 0.14 grams of 60% NaH (3.5 mmol) coated with mineral oil. After 30 minutes of stirring, 0.46 grams of bromomethylcyclopropane (3.4 mmol) was added and the reaction was allowed to stir overnight at room temperature.

The reaction was diluted with 60 mL of water and 150 mL of ethyl acetate. The organic phase was washed with 60 mL of water, dried and concentrated under reduced pressure. The crude product was chromatographed on silica gel with ethyl acetate/hexane to yield 0.23 grams of 1-cyclopropylmethyl-3-(3,4-dichlorophenyl)-4,5-dihydro-1,2,4-triazin-6-one.

Method G:

Preparation of 1-(2,2,2-trifluoroethyl)-3-(3,5-dichlorophenyl)-4-allyloxycarbonyl-4,5-dihydro-1,2,4-triazin-6-one (Compound 10)

To a solution of 1-(2,2,2-trifluoroethyl)-3-(3,5-dichlorophenyl)-4,5-dihydro-1,2,4-triazin-6-one (110 mg, 0.34 mmol) in 5 mL tetrahydrofuran at was added sodium hydride (30 mg, 0.67 mmol). After the reaction stirred 5 min, the allyl chloroformate (0.07 mL, 0.67 mmol) was added dropwise. After the reaction was heated at reflux for 6 h, it was quenched with water and diluted with ethyl acetate. The two layers were separated and the aqueous phase was extracted with ethyl acetate (3×5 mL). The combined organic extracts were dried over $MgSO_4$, filtered, and concentrated in vacuo. Flash column chromatography (100% hexanes-10% ethyl acetate/hexanes) afforded the acylated product 1-(2,2,2-trifluoroethyl)-3-(3,5-dichlorophenyl)-4-allyloxycarbonyl-4,5-dihydro-1,2,4-triazin-6-one (130 mg, 93%) as a yellow oil in 100% purity by gas chromatography (GC).

Preparation of 1,4-di-(t-butoxycarbonyl)-3-(3,5-dichlorphenyl)-4,5-dihydro-1,2,4-triazin-6-one (Compound 11)

To a solution of 3-(3,5-dichlorophenyl)-4,5-dihydro-1,2,4-triazin-6-one (40 mg, 0.16 mmol) in 3 mL 1:1 dichloromethane/ethyl acetate at 0° C. was added N,N-diemethylaminopyridine (10 mg, 0.02 mmol) and di-tert-butylcarbonylanhydride (40 mg, 0.18 mmol). After the reaction stirred for 2 h at room temperature, it was quenched with water and diluted with ethyl acetate. The two layers were separated and the organic phase was washed with water (1×5 mL), dried over $MgSO_4$, filtered, and concentrated in vacuo. After flash column chromatography (10% ethyl acetate/hexanes) the acylated product 1,4-di-(t-butoxycarbonyl)-3-(3,5-dichlorphenyl)-4,5-dihydro-1,2,4-triazin-6-one (50 mg, 71%) was afforded.

Preparation of 1-n-butyl-3-(3,4-dichlorophenyl)-4-methylthiothiocarbonyl-4,5-dihydro-1,2,4-triazin-6-one (Compound 12)

To a solution of 1-n-butyl-3-(3,4-dichlorophenyl)-4,5-dihydro-1,2,4-triazin-6-one (310 mg, 1.03 mmol) dissolved in 5 mL tetrahydrofuran (THF) was added sodium hydride (40 mg, 1.03 mmol). After cooling the mixture to 0° C., carbon disulfide (0.09 mL, 1.45 mmol) was added. After the reaction was stirred at 0° C. for 20 min, iodomethane (0.19 mL, 3.0 mmol) was added. After the reaction was stirred at 0° C. for 1 h, it was quenched with water and diluted with ethyl acetate. The aqueous layer was extracted with ethyl acetate (3×5 mL), and the combined organic extracts were dried over magnesium sulfate, filtered, and concentrated in vacuo. The crude material was subjected to flash column chromatography (10% ethyl acetate/hexanes) to afford 1-nbutyl-3-(3,4-dichlorophenyl)-4-methyl-thiothiocarbonyl-4,5-dihydro-1,2,4-triazin-6-one (310 mg, 78%) as an orange solid in 98% purity.

Preparation of 1-n-butyl-3-(3.4-dichlorophenyl)-4-(2-phenylsulfonylethene)-4,5-dihydro-1,2,4-triazin-6-one (Compound 13)

To a solution of 1-n-butyl-3-(3,4-dichlorophenyl)-4,5-dihydro-1,2,4-triazin-6-one (400 mg, 1.33 mmol) in 10 mL THF at 0° C. was added lithium bis(trimethylsilyl)amide (LiHMDS) (250 mg, 1.47 mmol) and trans-1,2-bis(phenylsulfonyl)ethylene (450 mg, 1.47 mmol). After the reaction was stirred at 0° C. for 30 min, it was allowed to warm to room temperature and then stirred for 2 h. The reaction was quenched with water and diluted with ethyl acetate. The aqueous layer was extracted with ethyl acetate (3×5 mL), and the combined organic extracts were dried over magnesium sulfate, filtered, and concentrated in vacuo. Most of the crude material was subjected to gradient flash column chromatography (20% ethyl acetate/1% triethylamine/79% hexanes to 50% ethyl acetate/1% triethylamine/49% hexanes) to afford the product (260 mg) as a brown solid. The remaining insoluble crude product was filtered, washed with ethyl acetate, and dried to afford the product (100 mg). The two portions were combined to afford 1-n-butyl-3-(3,4-dichlorophenyl)-4-(2-phenyl-sulfonylethene)-4,5-dihydro-1,2,4-triazin-6-one (350 mg) in 56% yield.

Preparation of 1-(2,2,2-trifluoroethyl)-3-(3,5-dichlorophenyl)-4-(methoxycarbonylthio)-4,5-dihydro-1,2,4-triazin-6-one (Compound 14)

To a solution of 1-(2,2,2-trifluoroethyl)-3-(3,5-dichlorophenyl)-4,5-dihydro-1,2,4-triazin-6-one (110 mg, 0.34 mmol) dissolved in 5 mL tetrahydrofuran was added triethylamine (0.06 mL, 0.40 mmol) and methoxy-carbonylsulfenyl chloride (0.04 mL, 0.40 mmol). After 30 min, the reaction was quenched with water and diluted with ethyl acetate. The aqueous layer was extracted with ethyl acetate (2×5 mL), and the combined organic extracts were dried over magnesium sulfate, filtered, and concentrated in vacuo. The crude material was subjected to flash column chromatography (10% ethyl acetate/hexanes) to afford 1-(2,2,2-trifluoroethyl)-3-(3,5-dichlorophenyl)-4-(methoxycarbonylthio)-4,5-dihydro-1,2,4-triazin-6-one (60 mg, 43%) in 80% purity by LC.

Preparation of 1-(n-butyl)-3-(3,5-dichlorophenyl)-4-(chloromethyloxycarbonyl)-4,5-dihydro-1,2,4-triazin-6-one (Compound 15)

1-(n-Butyl)-3-(3,5-dichlorophenyl)-4,5-dihydro-1,2,4-triazin-6-one was acylated with chloromethyl chloroformate in a similar manner to the reaction described to make compound 14 except that pyridine was used as a base. The product 1-(n-butyl)-3-(3,5-dichlorophenyl)-4-(chloromethyloxycarbonyl)-4,5-dihydro-1,2,4-triazin-6-one was isolated in 51% yield.

Preparation of 1-(n-butyl)-3-(3,5-dichlorophenyl)-4-(iodomethyloxycarbonyl)-4,5-dihydro-1,2,4-triazin-6-one (Compound 16)

1-(n-Butyl)-3-(3,5-dichlorophenyl)-4-(chloromethyloxycarbonyl)-4,5-dihydro-1,2,4-triazin-6-one was treated with sodium iodide in acetone as described in Folkmann, M.; Lund, F. *J. Synthesis* 1990, 1159 to give 1-(n-butyl)-3-(3,5-dichlorophenyl)-4-(iodomethyloxycarbonyl)-4,5-dihydro-1,2,4-triazin-6-one.

Method H:

Preparation of 1-Butyl-3-(3,4-dichlorophenyl)-4,5-dihydro-1,2,4-triazin-6-thione (Compound 17)

To a solution of 1.31 grams of 1-butyl-3-(3,4-dichlorophenyl)-4,5-dihydro-1,2,4-triazin-6-one (4.4 mmol) in 12 mL of toluene was added 0.37 gram of phosphorus pentasulfide (8.3 mmol). The reaction was heated to 95° C. for seven hours. After cooling 1.4 grams of flash grade silica gel was added. The reaction was filtered through Celite and concentrated under reduced pressure. The oil was chromatographed with 22% ethyl acetate/hexanes and 0.95 grams of 1-butyl-3-(3,4-dichlorophenyl)-4,5-dihydro-1,2,4-triazin-6-thione was isolated.

Method I:

Preparation of 1-(2,2,2-Trifluoroethyl)-3-(3,5-dichlorophenyl)-5-methoxy-4,5-dihydro-1,2,4-triazin-6-one (Compound 18)

To a solution of 1-(2,2,2-trifluoroethyl)-3-(3,5-dichlorophenyl)-1,2,4-triazin-6-one (70 mg, 0.21 mmol) dissolved in 3 mL of a 1:1 mixture of ethyl acetate and methanol was added a small scoopula of neutral alumina. After stirring for 20 minutes, the mixture was filtered through a small plug of glass wool and concentrated. The product (80 mg) was afforded in 96% purity and 100% yield.

Preparation of 1-(2,2,2-trifluoroethyl)-3-(4-chlorophenyl)-5-propylthio-4,5-dihydro-1,2,4-triazin-6-one (Compound 19)

A solution of 1-(2,2,2-trifluoroethyl)-3-(4-chlorophenyl)-1,2,4-triazin-6-one (0.40 g, 1.4 mmol), prepared in a similar manner to Compound 7 in 5 mL of ethyl acetate was treated with excess propanethiol at room temperature. The reaction mixture was stirred for 1 hour, then more ethyl acetate was added. The reaction mixture was washed with aqueous potassium carbonate (twice), water and brine, dried over magnesium sulfate, filtered and stripped. The resultant solid was recrystallized from methylene chloride/hexane to give 0.28 g of pale yellow crystals (55% yield), mp 99-100° C.

Preparation of 1-(2,2,2-Trifluorethyl)-3-(4-chlorophenyl)-5-(2-propanone)-4,5-dihydro-1,2,4-triazin-6-one (Compound 20)

A solution of 0.63 grams of 1-(2,2,2-trifluorethyl)-3-(4-chlorophenyl)-1,2,4-triazin-6-one (1.9 mmol) in 20 mL of acetone and 1.5 ml of pH 10 phosphate buffer was stirred for eight days at room temperature. The reaction was diluted with 50 mL of water and 125 mL of ethyl acetate. The organic phase was separated, dried, and concentrated under reduced pressure. The crude was triturated with 50 ml of ethyl acetate and the insolubles were discarded. The material was chromatographed with 50-100% ethyl acetate/hexanes to give 0.17 g of 1-(2,2,2-trifluorethyl)-3-(4-chlorophenyl)-5-(2-propanone)-4,5-dihydro-1,2,4-triazin-6-one.

Method J:

Preparation of 1-(2,2,2-Trifluorethyl)-3-(3,5-dichlorophenyl)-1,2,4-triazin-5,6-dione (Compound 21)

To an ice-cooled solution of ethyl 3,5-dichlorobenzimidate hydrochloride (2.46 g, 9.65 mmol) dissolved in 100 mL ethanol was added an aqueous solution of trifluoroethylhydrazine (70 wt %, 9.65 mmol). The reaction was stirred 4 h at room temperature, and then quenched with saturated sodium bicarbonate solution and diluted with ethyl acetate. The organic layer was dried over magnesium sulfate, filtered and concentrated in vacuo to afford 2.7 g of the amidrazone as a light brown oil which is 58% pure. To a solution of the amidrazone in 10 mL of toluene was added triethylamine (2.9 mL, 20.8 mmol). The reaction was cooled to 0° C. and oxalyl chloride (0.9 mL, 10.4 mmol) was added over 10 min. After the reaction stirred for 30 min at 0° C., it was quenched with water and diluted with ethyl acetate. The organic layer was washed with brine, dried over magnesium sulfate, filtered, and concentrated in vacua. The crude reaction mixture was subjected to flash column chromatography (10% ethyl acetate/hexanes–100% ethyl acetate) to afford the diketone (250 mg, 8% yield) in 74% purity.

Method K:

Preparation of 1-Butyl-3-methyl-5-(4-methylphenyl)-4,5-dihydro-1,2,4-triazin-6-one (Compound 22)

4-Methylphenylmagnesium bromide (1.64 mL, 1.0 M in ether) was added all at once via syringe to a well-stirred solution of 1-n-butyl-3-methyl-1,2,4-triazin-6-one (178 mg, 1.06 mmol) in ether (9.85 mL) under $N_2$ at room temperature. After stirring the resulting mixture overnight, saturated aqueous $NH_4Cl$ (10 mL) and ethyl acetate (10 mL) were added, the organic phase was separated, and the aqueous layer was extracted once more with ethyl acetate. The combined organic layers were dried over $Na_2SO_4$ and evaporated to dryness. The crude product was purified by flash chromatography on silica gel (5 g, 4:1 hexanes:ethyl acetate) to afford Compound 22 as a tan solid (236 mg, 86% yield).

Miscellaneous:

9,10-Dichloro-2-butyl-1,2,4-triazino[3,4-a]isoindol-3(4H)-one (Compound 23)

Compound 23 was prepared in 5 steps from 4,5-dichlorophthalimide as shown in the scheme below:

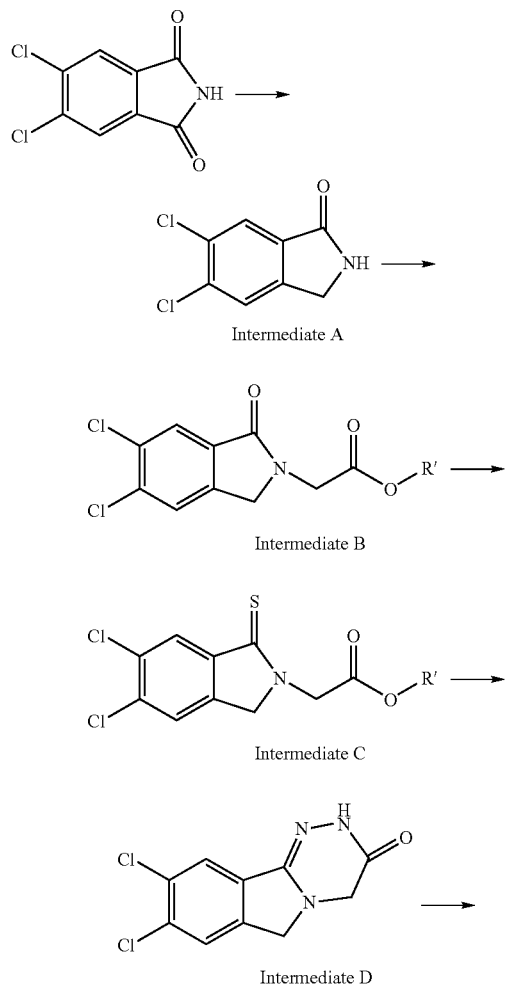

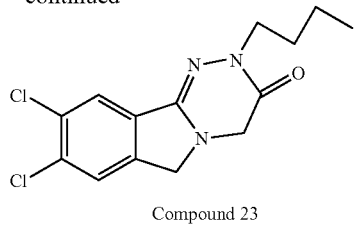

Compound 23

A mixture of 6 g of 4,5-dichlorophthalimide and 13.8 g of zinc dust in 200 mL of acetic acid was refluxed for 6 hours. It was cooled to 70° C., then filtered through Celite and stripped. Methylene chloride and saturated aqueous sodium bicarbonate solution were added, and the mixture was stirred overnight. The solids were filtered and dried in a vacuum oven. This product (intermediate A) was used without further purification.

To 1.03 g of intermediate A (5.1 mmol) in 5 ml of DMF was added 0.21 g of sodium hydride (60%, 5.25 mmol). The reaction mixture was stirred 0.5 hour, then 0.92 g of ethyl bromoacetate (5.25 mmol) was added. The reaction mixture was stirred overnight, then it was diluted with water and extracted with ethyl acetate. The phases were separated, the organic phase was washed with water and brine and dried over magnesium sulfate, then stripped. Column chromatography gave 0.42 g of intermediate B.

Intermediate B (0.69 g, 2.4 mmol) and 0.13 g (2.9 mmol) of phosphorus pentasulfide were heated to 90° C. in toluene. The product was cooled and filtered through silica gel to give 0.6 g of product which was 5:1 intermediate C to intermediate B. This material was used without further purification.

Intermediate C (0.6 g, 2 mmol) and 0.13 g of hydrazine hydrate (2.6 mmol) in 5 mL of ethanol were refluxed to give intermediate D. This material could be purified by chromatography.

Intermediate D (0.07 g, 0.3 mmol) was deprotonated with 0.02 g of sodium hydride (60%, 0.5 mmol) in DMF. After 15 minutes, n-butyl iodide was added, and the reaction was stirred overnight. The reaction mixture was diluted with water and extracted with ethyl acetate. The phases were separated, the organic phase was washed with water and brine and dried over magnesium sulfate, then stripped. Chromatography gave 0.02 g of Compound 23.

2-Pentyl-7-(4-chlorophenyl)-pyridazino[6,1-c][1,2,4]triazin-3(4H)one (Compound 24)

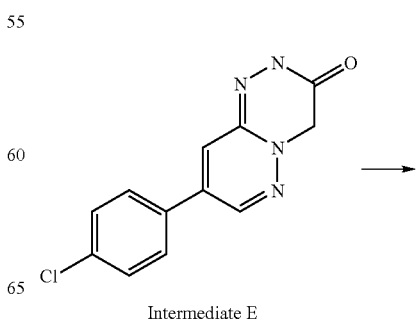

Intermediate E

-continued

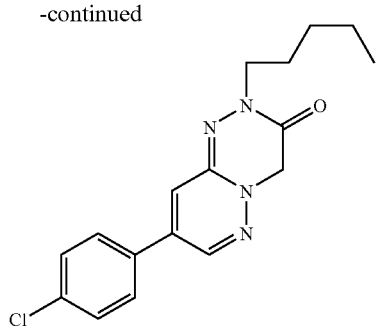

Compound 24

2-H-7-(4-chlorophenyl)-pyridazino[6,1-c][1,2,4]triazin-3 (4H)one (Intermediate E) was prepared from 6-(4-chlorophenyl)-pyridazin-3-one (for synthesis, see Steck et al, *J. Amer. Chem. Soc.* (1953), 75, 1117; or Coates, W. J., McKillop, A. *Synthesis*, (1993), 334-342; or Tisler, M., Stanovnik, B. in "Comprehensive Heterocyclic Chemistry", Katritsky and Rees, ed., Volume 3, Part 2B, Pergamon Press, 1984, p1) in three steps by a similar sequence to the one used to convert Intermediate A into Intermediate D in the example above.

To a solution of Intermediate E (130 mg, 0.50 mmol) in 5 mL DMF was added potassium carbonate (80 mg, 0.60 mmol) and iodopentane (0.08 mL, 0.60 mmol). The mixture was stirred at room temperature for 45 min and then at 65° C. for 1.5 h. After stirring at room temperature overnight, the reaction was quenched with water and diluted with ethyl acetate. The aqueous layer was extracted with ethyl acetate (3×5 mL), and the combined organic extracts were dried over magnesium sulfate, filtered, and concentrated in vacua. The crude material was subjected to flash column chromatography twice (20% ethyl acetate/hexanes) to afford the product (120 mg, 75%) as an orange solid.

1-n-Butyl-3-(2-hydroxyphenyl)-4,5-dihydro-1,2,4-triazin-6-one (Compound 83)

To a solution of Compound 195 (1.53 g, 5.86 mmol), prepared by the reactions described for Method B, dissolved in 10 ml DMF, was added ethanethiol, sodium salt (1.97 g, 23.5 mmol) as a free-flowing solid. The resulting mixture was heated at 100° C. for 4.5 h. After it was allowed to stir overnight, the reaction was quenched with water and diluted with ethyl acetate. The aqueous layer was extracted with ethyl acetate (3×5 ml). The combined organic layers were dried over magnesium sulfate, filtered and concentrated in vacuo. After flash column chromatography (20-50% ethyl acetate/hexanes), Compound 83 was afforded (0.79 g, 54% yield) as a brown solid.

3-n-Butyl-3H-9-oxa-3,10a-diaza-phenanthrene-2,10-dione (Compound 25)

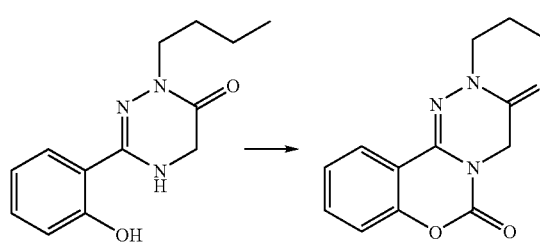

Compound 83        Compound 25

To a solution of Compound 83 (0.21 g, 0.85 mmol) dissolved in 5 mL dichloromethane, was added triethylamine (0.13 mL, 0.94 mmol). The solution was cooled to 0° C. in an ice bath, and triphosgene (0.28 g, 0.94 mmol) was added. After 15 min, the cooling bath was removed. After the reaction stirred for 45 minutes at room temperature, the reaction was complete by TLC. The reaction was quenched with saturated sodium bicarbonate solution. The organic layer was washed with brine, dried over magnesium sulfate, filtered and concentrated in vacuo. Flash column chromatography (15-20% ethyl acetate/hexanes), afforded 90 mg (39% yield) of Compound 25 as a yellow oil.

By similar methods the following compounds were prepared as shown in Table 1.

TABLE 1

4,5-Dihydro-1,2,4-triazin-6-ones

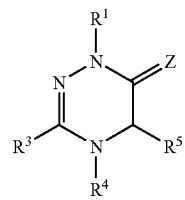

| # | $R^1$ | $R^3$ | $R^4$ | $R^5$ | Z |
|---|---|---|---|---|---|
| 26 | 2,2,2-trifluoroethyl | 4-chlorophenyl | hydrogen | methoxy | O |
| 27 | methyl | 4-chlorophenyl | hydrogen | hydrogen | O |
| 28 | phenyl | 4-chlorophenyl | hydrogen | hydrogen | O |
| 29 | phenyl | 4-chlorophenyl | hydrogen | hydrogen | O |
| 30 | benzyl | 4-chlorophenyl | hydrogen | hydrogen | O |
| 31 | methyl | phenyl | hydrogen | hydrogen | O |
| 32 | hydrogen | phenyl | hydrogen | hydrogen | O |
| 33 | 2,2,2-trifluoroethyl | phenyl | hydrogen | hydrogen | O |
| 34 | 2,2,2-trifluoroethyl | phenyl | methyl | hydrogen | O |
| 35 | 2,2,2-trifluoroethyl | 4-methoxyphenyl | hydrogen | hydrogen | O |
| 36 | n-butyl | 4-methoxyphenyl | hydrogen | hydrogen | O |
| 37 | 2,2,2-trifluoroethyl | 3-chlorophenyl | hydrogen | hydrogen | O |
| 38 | n-butyl | 4-methoxyphenyl | hydrogen | methyl | O |
| 39 | 2,2,2-trifluoroethyl | 4-methoxyphenyl | hydrogen | methoxy | O |
| 40 | 2,2,2-trifluoroethyl | 4-chlorophenyl | acetyl | hydrogen | O |
| 41 | 2,2,2-trifluoroethyl | 4-methylphenyl | hydrogen | hydrogen | O |
| 42 | 2,2,2-trifluoroethyl | 4-chlorophenyl | methanesulfonyl | hydrogen | O |
| 43 | 2,2,2-trifluoroethyl | 3,5-dichlorophenyl | hydrogen | hydrogen | O |
| 44 | 2,2,2-trifluoroethyl | benzyl | hydrogen | hydrogen | O |
| 45 | 2,2,2-trifluoroethyl | cyclohexyl | hydrogen | hydrogen | O |
| 46 | 2,2,2-trifluoroethyl | 3-methoxyphenyl | hydrogen | hydrogen | O |
| 47 | 2,2,2-flurooethyl | 3,5-dichloro-4-methylphenyl | hydrogen | hydrogen | O |
| 48 | 2-butyl | cyclohexyl | hydrogen | hydrogen | O |
| 49 | n-pentyl | 3,5-dichloro-4-methylphenyl | hydrogen | hydrogen | O |
| 50 | n-butyl | 4-chlorophenyl | hydrogen | hydrogen | O |
| 51 | 2,2,2-trifluoroethyl | 4-trifluoromethylphenyl | hydrogen | hydrogen | O |
| 52 | 2,2,2-trifluoroethyl | 2-pyridyl | hydrogen | hydrogen | O |

TABLE 1-continued 4,5-Dihydro-1,2,4-triazin-6-ones

| # | R¹ | R³ | R⁴ | R⁵ | Z |
|---|---|---|---|---|---|
| 53 | 2,2,2-tri-fluoroethyl | 2-pyridyl | hydrogen | hydroxy[b] | O |
| 54 | n-pentyl | 4-chlorophenyl | hydrogen | hydrogen | O |
| 55 | n-hexyl | 4-chlorophenyl | hydrogen | hydrogen | O |
| 56 | n-octyl | 4-chlorophenyl | hydrogen | hydrogen | O |
| 57 | n-decyl | 4-chlorophenyl | hydrogen | hydrogen | O |
| 58 | 3-methyl-phenyl | 4-chlorophenyl | hydrogen | hydrogen | O |
| 59 | 2-pyridyl | 4-chlorophenyl | hydrogen | hydrogen | O |
| 60 | cyanomethyl | 4-chlorophenyl | hydrogen | hydrogen | O |
| 61 | trimethyl-silylmethyl | 4-chlorophenyl | hydrogen | hydrogen | O |
| 62 | 2-(5-chloro-thio-phene)-methyl | 4-chlorophenyl | hydrogen | hydrogen | O |
| 63 | 2-(5-chloro-thio-phene)-methyl | 4-chlorophenyl | 2-(5-chloro-thio-phene)-methyl | hydrogen | O |
| 64 | hydrogen | 3,5-dichlorphenyl | hydrogen | hydrogen | O |
| 65 | 2-chloroallyl | 3,5-dichlorphenyl | hydrogen | hydrogen | O |
| 66 | 3-chloro-allyl[a] | 3,5-dichlorphenyl | 3-chloro-allyl[a] | hydrogen | O |
| 67 | 3-chloro-allyl[a] | 3,5-dichlorphenyl | hydrogen | hydrogen | O |
| 68 | n-butyl | 5-(2-methyl-4-tri-fluoro-methylthiazole) | hydrogen | hydrogen | O |
| 69 | n-butyl | 3,4-difluorophenyl | hydrogen | hydrogen | O |
| 70 | 2,2,2-tri-fluoroethyl | 2,5-dichlorophenyl | hydrogen | hydrogen | O |
| 71 | 2,2,2-tri-fluoroethyl | 3,5-dichlorophenyl | methoxy-carbonyl | hydrogen | O |
| 72 | 2,2,2-tri-fluoroethyl | 3,5-dichlorophenyl | acetyl | hydrogen | O |
| 73 | 2,2,2-tri-fluoroethyl | 2,4-dichlorophenyl | hydrogen | hydrogen | O |
| 74 | n-butyl | 2,5-dichlorophenyl | hydrogen | hydrogen | O |
| 75 | n-butyl | methyl | hydrogen | 4-methyl-phenyl | O |
| 76 | n-butyl | methyl | hydrogen | 2-methyl-phenyl | O |
| 77 | n-butyl | methyl | hydrogen | 3-methyl-phenyl | O |
| 78 | n-butyl | methyl | hydrogen | 3-amino-phenyl | O |
| 79 | n-butyl | methyl | hydrogen | 4-methoxy-phenyl | O |
| 80 | n-butyl | methyl | hydrogen | 3-methoxy-phenyl | O |
| 81 | n-butyl | methyl | hydrogen | 4-chloro-phenyl | O |
| 82 | n-butyl | methyl | hydrogen | 2,4,6-tri-methyl-phenyl | O |
| 83 | n-butyl | 2-hydroxyphenyl | hydrogen | hydrogen | O |
| 84 | 2,2,2-tri-fluoroethyl | 3-fluorophenyl | hydrogen | hydrogen | O |
| 85 | n-butyl | 3,4-dichloro-phenyl | methyl-oxalate | hydrogen | O |
| 86 | cyclopropyl-methyl | 3-trifluoromethyl-phenyl | hydrogen | hydrogen | O |
| 87 | propargyl | 3-trifluoromethyl-phenyl | propargyl | hydrogen | O |
| 88 | propargyl | 3-trifluoromethyl-phenyl | hydrogen | hydrogen | O |
| 89 | 2,2,2-tri-fluoroethyl | 3-trifluoromethyl-phenyl | propargyl | hydrogen | O |
| 90 | 2,2,2-tri-fluoroethyl | 3,5-(bis)trifluoromethyl phenyl | hydrogen | hydrogen | O |
| 91 | 2,2,2-tri-fluoroethyl | 3-trifluoromethyl-phenyl | allenyl | hydrogen | O |
| 92 | n-butyl | methyl | hydrogen | phenyl | O |
| 93 | n-butyl | methyl | hydrogen | 4-fluoro-phenyl | O |
| 94 | n-butyl | methyl | hydrogen | 3-methyl-4-fluoro-phenyl | O |
| 95 | n-butyl | methyl | hydrogen | 4-t-butyl phenyl | O |
| 96 | 2,2,2-tri-fluoroethyl | 2-fluorophenyl | hydrogen | hydrogen | O |
| 97 | 2,2,2-tri-fluoroethyl | 2-chlorophenyl | hydrogen | hydrogen | O |
| 98 | 2,2,2-tri-fluoroethyl | 3,4-difluoro-phenyl | hydrogen | hydrogen | O |
| 99 | 2,2,2-tri-fluoroethyl | 3,4-dichloro-phenyl | hydrogen | hydrogen | O |
| 100 | ethyl | 3,4-dichloro-phenyl | hydrogen | hydrogen | O |
| 101 | n-butyl | 3,4-dichloro-phenyl | hydrogen | hydrogen | O |
| 102 | ethoxy-carbonyl-methyl | 3,4-dichloro-phenyl | hydrogen | hydrogen | O |
| 103 | benzyl | 3,4-dichloro-phenyl | hydrogen | hydrogen | O |
| 104 | n-butyl | 3,5-dichloro-phenyl | hydrogen | hydrogen | O |
| 105 | 2,2,2-tri-fluoroethyl | 2-methylphenyl | hydrogen | hydroxy | O |
| 106 | n-butyl | 3-chloro-4-fluoro-phenyl | hydrogen | hydrogen | O |
| 107 | propyl | 3-5-dichloro-phenyl | hydrogen | hydrogen | O |
| 108 | 2-ethoxy-ethyl | 3-5-dichloro-phenyl | hydrogen | hydrogen | O |
| 109 | cyclopropyl-methyl | 3-5-dichloro-phenyl | hydrogen | hydrogen | O |
| 110 | n-butyl | 3-chlorophenyl | hydrogen | hydrogen | O |
| 111 | phenyl | 3-chlorophenyl | hydrogen | hydrogen | O |
| 112 | 3-methyl-phenyl | 3-chlorophenyl | hydrogen | hydrogen | O |
| 113 | 2,2,2-tri-fluoroethyl | 3,5-dichloro-phenyl | vinyloxy-carbonyl | hydrogen | O |
| 114 | n-butyl | 3-methoxyphenyl | hydrogen | hydrogen | O |
| 115 | n-butyl | 3-trifluoromethyl-phenyl | hydrogen | hydrogen | O |
| 116 | n-butyl | 4-ethoxyphenyl | hydrogen | hydrogen | O |
| 117 | n-butyl | 4-trifluoromethyl-phenyl | hydrogen | hydrogen | O |
| 118 | n-butyl | 3,5-dichloro-phenyl | acetoxy-methoxy-carbonyl | hydrogen | O |

TABLE 1-continued 4,5-Dihydro-1,2,4-triazin-6-ones

| # | R¹ | R³ | R⁴ | R⁵ | Z |
|---|---|---|---|---|---|
| 119 | n-butyl | 2-naphthyl | hydrogen | hydrogen | O |
| 120 | n-butyl | 3,5-dibromo-4-methoxyphenyl | hydrogen | hydrogen | O |
| 121 | n-butyl | 3,5-dichloro-4-pyridyl | hydrogen | hydrogen | O |
| 122 | methyl | 4-trifluoromethyl-phenyl | hydrogen | hydrogen | O |
| 123 | 2,2,2-trifluoroethyl | 3,5-dichlorophenyl | methyl-oxalate | hydrogen | O |
| 124 | hydrogen | 2-naphthyl | hydrogen | hydrogen | O |
| 125 | ethoxycarbonyl-methyl | 3,4-difluorophenyl | hydrogen | hydrogen | O |
| 126 | 2,2,2-trifluoroethyl | 3,5-dichlorophenyl | 2-chloroethyl | hydrogen | O |
| 127 | n-butyl | 3,5-dichlorophenyl | vinyloxy-carbonyl | hydrogen | O |
| 128 | allyl | 3,5-dichlorophenyl | hydrogen | hydrogen | O |
| 129 | n-butyl | 3,5-dichlorophenyl | (methylthio)carbonyl | hydrogen | O |
| 130 | n-butyl | 3,5-dichlorophenyl | methoxycarbonyl | hydrogen | O |
| 131 | n-butyl | 3,5-dichlorophenyl | propargyl | hydrogen | O |
| 132 | n-butyl | 3,5-dichlorophenyl | allyloxy-carbonyl | hydrogen | O |
| 133 | n-butyl | 3,5-dichlorophenyl | propargyl-oxy-carbonyl | hydrogen | O |
| 134 | 2,2,2-trifluoroethyl | 3,5-dichlorophenyl | 2-propenyl-oxy-carbonyl | hydrogen | O |
| 135 | n-butyl | 3,5-dichlorophenyl | 2-propenyl-oxy-carbonyl | hydrogen | O |
| 136 | n-butyl | 3,2-dichlorophenyl | vinyloxy-carbonyl | hydrogen | O |
| 137 | 2,2,2-trifluoroethyl | 3,5-dichlorophenyl | acryloyl | hydrogen | O |
| 138 | n-butyl | 3,5-dichlorophenyl | acryloyl | hydrogen | O |
| 139 | benzyl | 3,4-difluorophenyl | hydrogen | hydrogen | O |
| 140 | 2,2,2-trifluoroethyl | 2-furyl | hydrogen | hydrogen | O |
| 141 | 2,2,2-trifluoroethyl | 3-quinoline | hydrogen | hydrogen | O |
| 142 | 2,2,2-trifluoroethyl | 4-(4-nitrophenyl)-phenyl | hydrogen | hydrogen | O |
| 143 | 2,2,2-trifluoroethyl | 2-naphthyl | hydrogen | hydrogen | O |
| 144 | 2,2,2-trifluoroethyl | 4-(4-1,2,3-thiadiazole)phenyl | hydrogen | hydrogen | O |
| 145 | 2,2,2-trifluoroethyl | 4-propoxyphenyl | hydrogen | hydrogen | O |
| 146 | 2,2,2-trifluoroethyl | 4-phenylphenyl | hydrogen | hydrogen | O |
| 147 | 2,2,2-trifluoroethyl | 4-methyl-thiophenyl | hydrogen | hydrogen | O |
| 148 | n-propyl | 4-fluorophenyl | hydrogen | hydrogen | O |
| 149 | 2,2,2-trifluoroethyl | 4-fluorophenyl | hydrogen | hydrogen | O |
| 150 | 2,2,2-trifluoroethyl | 4-ethylphenyl | hydrogen | hydrogen | O |
| 151 | n-propyl | 4-propoxyphenyl | hydrogen | hydrogen | O |
| 152 | hydrogen | 4-propoxyphenyl | hydrogen | hydrogen | O |
| 153 | 2,2,2-trifluoroethyl | 3-trifluoromethylphenyl | hydrogen | hydrogen | O |
| 154 | 2,2,2-trifluoroethyl | 3-methylphenyl | hydrogen | hydrogen | O |
| 155 | 2,2,2-trifluoroethyl | 4-butyloxyphenyl | hydrogen | hydrogen | O |
| 156 | methyl | 4-phenoxyphenyl | hydrogen | hydrogen | O |
| 157 | 2,2,2-trifluoroethyl | 4-nitro-3-methyl-phenyl | hydrogen | hydrogen | O |
| 158 | 2,2,2-trifluoroethyl | 3,5-dibromo-4-methoxyphenyl | hydrogen | hydrogen | O |
| 159 | 2,2,2-trifluoroethyl | 3,5-dichloro-4-pyridyl | hydrogen | hydrogen | O |
| 160 | 2-cyanoethyl | 4-butyloxyphenyl | hydrogen | hydrogen | O |
| 161 | 4-chlorophenyl | 4-ethoxyphenyl | hydrogen | hydrogen | O |
| 162 | n-butyl | 2-benzothiophene | hydrogen | hydrogen | O |
| 163 | 2,2,2-trifluoroethyl | 2-benzothiophene | hydrogen | hydrogen | O |
| 164 | n-propyl | 3,5-dichlorphenyl | hydrogen | hydrogen | O |
| 165 | ethoxycarbonyl-methyl | 3-methylphenyl | hydrogen | hydrogen | O |
| 166 | 2-cyanoethyl | 4-(nitro-phenyl)phenyl | hydrogen | hydrogen | O |
| 167 | 2,2,2-trifluoroethyl | 3-nitrophenyl | hydrogen | hydrogen | O |
| 168 | n-butyl | 3,4-dichlorophenyl | propargyl | hydrogen | O |
| 169 | 2,2,2-trifluoroethyl | 3,5-dichlorophenyl | propargyl | hydrogen | O |
| 170 | n-butyl | 3,4-dichlorophenyl | 2-propenyl-oxy-carbonyl | hydrogen | O |
| 171 | n-butyl | 3,4-dichlorophenyl | propargyl-oxy-carbonyl | hydrogen | O |
| 172 | n-butyl | 3,4-dichlorophenyl | allyloxy-carbonyl | hydrogen | O |
| 173 | n-butyl | 3,4-dichlorophenyl | phenoxy-carbonyl | hydrogen | O |
| 174 | hydrogen | 3,4-dichlorophenyl | hydrogen | hydrogen | O |
| 175 | n-butyl | 3-cyanophenyl | hydrogen | hydrogen | O |
| 176 | 2,2,2-trifluoroethyl | 3-cyanophenyl | hydrogen | hydrogen | O |
| 177 | n-butyl | 3,4-dichlorophenyl | 1-crotonyl | hydrogen | O |
| 178 | n-butyl | 3,4-dichlorophenyl | phenoxy-thio-carbonyl | hydrogen | O |
| 179 | n-butyl | 3,4-dichlorophenyl | 2-chloro-ethyl-oxy-carbonyl | hydrogen | O |
| 180 | n-butyl | 3,4-dichlorophenyl | 2-pentynyl | hydrogen | O |
| 181 | n-butyl | 3,4-dichlorophenyl | cyclopropyl-carbonyl | hydrogen | O |

TABLE 1-continued 4,5-Dihydro-1,2,4-triazin-6-ones

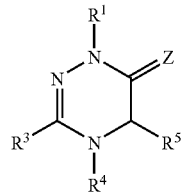

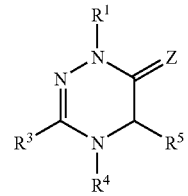

| # | R$^1$ | R$^3$ | R$^4$ | R$^5$ | Z |
|---|---|---|---|---|---|
| 182 | n-butyl | 3,4-dichlorophenyl | benzyl | hydrogen | O |
| 183 | n-butyl | 3,4-dichlorophenyl | butynyl | hydrogen | O |
| 184 | benzyl | 3-nitrophenyl | hydrogen | hydrogen | O |
| 185 | benzyl | 2-pyridyl | hydrogen | hydrogen | O |
| 186 | 3-methylphenyl | 4-phenylphenyl | hydrogen | hydrogen | O |
| 187 | 3-methylphenyl | 4-methylthiophenyl | hydrogen | hydrogen | O |
| 188 | 3-methylphenyl | 6-(2,2,2-trifluoroethoxy)-3-pyridyl | hydrogen | hydrogen | O |
| 189 | 2-phenethyl | 4-ethylphenyl | hydrogen | hydrogen | O |
| 190 | benzyl | 4-(2,6-dichloropyridine) | hydrogen | hydrogen | O |
| 191 | n-butyl | 3,4-dichlorophenyl | allyl-thiocarbonyl | hydrogen | O |
| 192 | n-butyl | 3,4-dichlorophenyl | propargyl-thio-thiocarbonyl | hydrogen | O |
| 193 | 2,2,2-trifluoroethyl | 3,5-dichlorophenyl | phenoxycarbonyl | hydrogen | O |
| 194 | n-butyl | 3,5-dichlorophenyl | phenoxycarbonyl | hydrogen | O |
| 195 | n-butyl | 2-methoxyphenyl | hydrogen | hydrogen | O |
| 196 | 3-chlorophenyl | 3,4-dichlorophenyl | hydrogen | hydrogen | O |
| 197 | n-pentyl | 3,4-dichlorophenyl | hydrogen | hydrogen | O |
| 198 | ethoxycarbonyl | 3-chlorophenyl | hydrogen | hydrogen | O |
| 199 | n-butyl | 3,4-dichlorophenyl | 4-methoxybenzyl | hydrogen | O |
| 200 | n-butyl | 3,4-dichlorophenyl | 3,4-dimethoxybenzyl | hydrogen | O |
| 201 | n-butyl | 3,4-dichlorophenyl | cyclobutylmethyl | hydrogen | O |
| 202 | n-butyl | 3,4-dichlorophenyl | hydrogen | vinyl | O |
| 203 | n-butyl | 3,4-dichlorophenyl | hydrogen | 1-methyl-ethene | O |
| 204 | 4-chlorophenyl | n-butyl | hydrogen | hydrogen | O |
| 205 | 2,2,2-trifluoroethyl | phenethyl | hydrogen | hydrogen | O |
| 206 | n-butyl | 4-(4-carboethoxy-phenyl)phenyl | hydrogen | hydrogen | O |
| 207 | n-butyl | 3-bromo-4-fluorophenyl | hydrogen | hydrogen | O |
| 208 | 2,2,2-trifluoroethyl | 3-bromo-4-fluorophenyl | hydrogen | hydrogen | O |
| 209 | 2-pentynyl | 3,4-dichlorophenyl | 2-pentynyl | hydrogen | O |
| 210 | 2-pentynyl | 3,4-dichlorophenyl | hydrogen | hydrogen | O |
| 211 | n-butyl | 3-bromophenyl | hydrogen | hydrogen | O |
| 212 | 2,2,2-trifluoroethyl | 3-bromophenyl | hydrogen | hydrogen | O |
| 213 | n-butyl | 2-benzyloxyphenyl | hydrogen | hydrogen | O |
| 214 | 2,2,2-trifluoroethyl | 3,5-dichlorophenyl | ethoxycarbonyl | methoxy | O |
| 215 | propargyl | 3,4-dichlorophenyl | hydrogen | hydrogen | O |
| 216 | propargyl | 3,4-dichlorophenyl | propargyl | hydrogen | O |
| 217 | propargyl | 3-bromo-4-fluorophenyl | propargyl | hydrogen | O |
| 218 | propargyl | 3-bromo-4-fluorophenyl | hydrogen | hydrogen | O |
| 219 | cyclopropylmethyl | 3-bromo-4-fluorophenyl | cyclopropylmethyl | hydrogen | O |
| 220 | cyclopropylmethyl | 3-bromo-4-fluorophenyl | hydrogen | hydrogen | O |
| 221 | n-butyl | 3-fluorophenyl | hydrogen | hydrogen | O |
| 222 | cyclopropylmethyl | 3-fluorophenyl | cyclopropylmethyl | hydrogen | O |
| 223 | cyclopropylmethyl | 3-fluorophenyl | hydrogen | hydrogen | O |
| 224 | cyclopropylmethyl | 3-bromophenyl | cyclopropylmethyl | hydrogen | O |
| 225 | propargyl | 3-fluorophenyl | hydrogen | hydrogen | O |
| 226 | propargyl | 3-bromophenyl | propargyl | hydrogen | O |
| 227 | propargyl | 3-bromophenyl | hydrogen | hydrogen | O |
| 293 | 2,2,2-trifluoroethyl | 3-chloro-4-methyl-phenyl | hydrogen | hydrogen | O |
| 294 | n-butyl | 3-chloro-4-methylphenyl | hydrogen | hydrogen | O |
| 295 | n-butyl | 3,5-dimethylphenyl | hydrogen | hydrogen | O |
| 296 | 2,2,2-trifluoroethyl | 3,5-dimethylphenyl | hydrogen | hydrogen | O |

[a]Cis/trans isomers
[b]Ethoxy also present

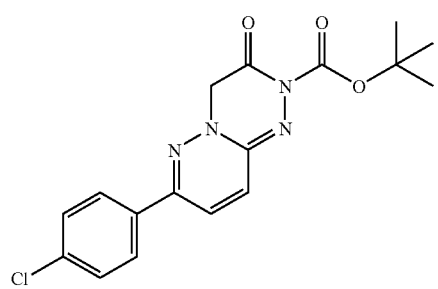

Compound 228

-continued
Compound 229
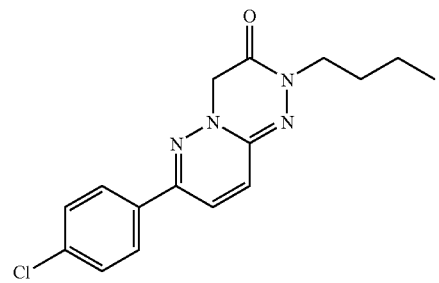
Compound 230
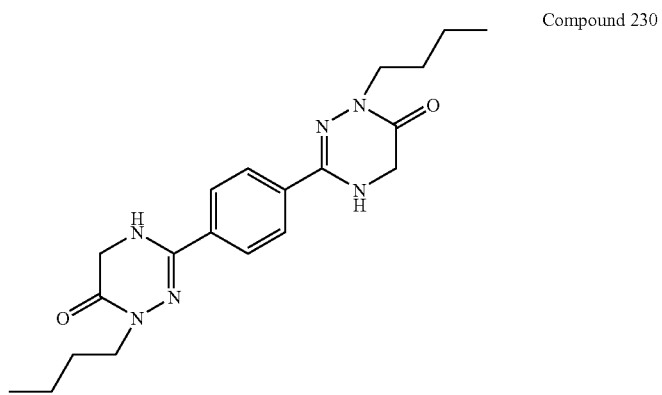
Compound 231
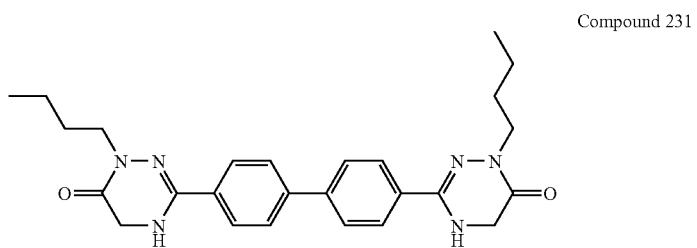
Compound 232
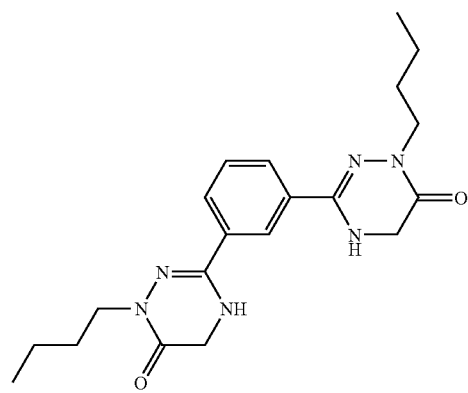

TABLE 2

1,2,4-Triazin-6-ones

| # | $R^1$ | $R^3$ | $R^5$ | Z |
|---|---|---|---|---|
| 233 | 2,2,2-trifluoroethyl | 4-chlorophenyl | hydrogen | O |
| 234 | n-pentyl | 4-chlorophenyl | hydrogen | O |
| 235 | ethyl | 4-chlorophenyl | hydrogen | O |
| 236 | allyl | 4-chlorophenyl | hydrogen | O |
| 237 | 2-pentynyl | 4-chlorophenyl | methyl | O |
| 238 | methyl | 4-chlorophenyl | hydrogen | O |
| 239 | 2,2,2-trifluoroethyl | 4-chlorophenyl | methyl | O |
| 240 | benzyl | 4-chlorophenyl | hydrogen | O |
| 241 | t-butyl | 4-chlorophenyl | hydrogen | O |
| 242 | methyl | phenyl | hydrogen | O |
| 243 | hydrogen | phenyl | hydrogen | O |
| 244 | n-butyl | 4-methoxyphenyl | hydrogen | O |
| 245 | 2,2,2-trifluoroethyl | 3-chlorophenyl | hydrogen | O |
| 246 | 2,2,2-trifluoroethyl | 3-chlorophenyl | hydrogen | S |
| 247 | 2,2,2-trifluoroethyl | 4-methylphenyl | hydrogen | O |
| 248 | 2,2,2-trifluoroethyl | 3,5-dichlorophenyl | hydrogen | O |
| 249 | 2,2,2-trifluoroethyl | benzyl | hydrogen | O |
| 250 | ethoxycarbonylmethyl | 4-chlorophenyl | hydrogen | O |
| 251 | 2,2,2-trifluoroethyl | cyclohexyl | hydrogen | O |
| 252 | 2,2,2-trifluoroethyl | 3-methoxyphenyl | hydrogen | O |
| 253 | 2,2,2-trifluoroethyl | 3,5-dichloro-4-methylphenyl | hydrogen | O |
| 254 | 2-pentyl | 4-chlorophenyl | hydrogen | O |
| 255 | 2-butyl | cyclohexyl | hydrogen | O |
| 256 | cyclohexyl | 4-chlorophenyl | hydrogen | O |
| 257 | n-pentyl | 3,5-dichloro-4-methylphenyl | hydrogen | O |
| 258 | n-butyl | 4-chlorophenyl | hydrogen | O |
| 259 | n-octyl | 4-chlorophenyl | hydrogen | O |
| 260 | n-decyl | 4-chlorophenyl | hydrogen | O |
| 261 | 2-pyridyl | 4-chlorophenyl | hydrogen | O |
| 262 | n-hexyl | 4-chlorophenyl | hydrogen | O |
| 263 | 2,2,2-trifluoroethyl | 2-fluorophenyl | hydrogen | O |
| 264 | cyanomethyl | 4-chlorophenyl | hydrogen | O |
| 265 | trimethylsilylmethyl | 4-chlorophenyl | hydrogen | O |
| 266 | 2-(5-chlorothiophene)-methyl | 4-chlorophenyl | hydrogen | O |
| 267 | 2,2,2-trifluoroethyl | 2-chlorophenyl | hydrogen | O |
| 268 | n-butyl | 5-(2-methyl-4-trifluoromethylthiazole) | hydrogen | O |
| 269 | n-butyl | 2,5-dichlorophenyl | hydrogen | O |
| 270 | n-butyl | 3,4-dichlorophenyl | hydrogen | O |
| 271 | n-butyl | 3,5-dichlorophenyl | hydrogen | O |
| 272 | cyclopropylmethy | 3,4-dichlorophenyl | hydrogen | O |
| 273[a] | n-butyl | 4-methylphenyl | hydrogen | O |
| 274 | 4-chlorophenyl | 4-ethoxyphenyl | hydrogen | O |
| 275 | ethoxycarbonylmethyl | 3-methylphenyl | hydrogen | O |
| 276 | 2-cyanoethyl | 4-(4-nitrophenyl)phenyl | hydrogen | O |
| 277 | n-butyl | 3-chlorophenyl | hydrogen | O |
| 278 | 3-methylphenyl | 3-chlorophenyl | hydrogen | O |
| 279 | 4-chlorophenyl | 4-(4-hexyloxyphenoxy)phenyl | hydrogen | O |
| 280 | n-propyl | 4-butyloxyphenyl | hydrogen | O |
| 281 | 2,2,2-trifluoroethyl | 4-propoxyphenyl | hydrogen | O |
| 282 | methyl | 4-phenoxyphenyl | hydrogen | O |
| 283 | n-butyl | 2-methoxyphenyl | hydrogen | O |
| 284 | n-butyl | methyl | 4-methylphenyl | O |
| 285 | n-butyl | methyl | 3-methylphenyl | O |
| 286 | n-butyl | methyl | 4-methoxyphenyl | O |
| 287 | n-butyl | 2-hydroxyphenyl | hydrogen | O |
| 288 | n-butyl | 3,5-bistrifluoromethylphenyl | hydrogen | O |
| 289 | n-butyl | 3-bromo-4-fluorophenyl | hydrogen | O |
| 290 | 2,2,2-trifluoroethyl | 3-bromo-4-fluorophenyl | hydrogen | O |

[a]Compound 273 was prepared and tested as a 1:1 mixture with its unoxidized (dihydro) form.

The diketone, compound 291 was obtained as a side product from an attempted preparation of 6-(2-methylphenyl)-1-(2,2,2-trifluoroethyl)-4,5-dihydro-1,2,4-triazin-6-one.

Compound 291

Compound 292 was also prepared by Method G as previously described.

Compound 292

TABLE 3

Spectral Characterization for Compounds 1=292

| # | HPLC/MS | NMR DATA(300 MHZ) |
|---|---|---|
| 1 | | (DMSO-d6): 4.01(s, 2H), 4.47(q, 2H), 7.54(t, 1H), 7.75(m, 1H), 7.84(br s, 1H), 7.93(d, 1H). |
| 2 | | (CDCl$_3$): 0.95(t, 3H), 1.37(hextet, 2H), 1.69(pentet, 2H), 3.73(t, 2H), 4.04(d, 2H), 5.09(br s, 1H), 7.30(dd, 1H), 7.45(d, 1H), 7.50(d, 1H). |
| 3 | 98%, 324(M + H) | |
| 4 | | (CDCl$_3$): 4.15(d, 2H), 4.39(q, 2H), 5.0(bs, 1H), 7.41(d, 2H), 7.60(d, 2H). |
| 5 | | (DMSO-d6): 3.87(s, 2H), 7.53(d, 2H), 7.66(d, 2H), 10.50(s, 1H). |
| 6 | | (CDCl$_3$): 1.58(s, 9H), 3.97(d, 2H), 4.9(bs, 1H), 7.38(d, 2H), 7.60(d, 2H). |
| 7 | | (CDCl$_3$): 4.77(q, 2H), 7.48(m, 3H), 8.14(m, 2H), 8.56(s, 1H). |
| 8 | | (CDCl$_3$): 1.14(t, 3H), 2.22(dq, 2H), 4.89(t, 2H), 7.45(d, 2H), 8.13(d, 2H), 8.48(s, 1H). |
| 9 | | (CDCl$_3$): 0.30(m, 2H), 0.44(m, 2H), 1.18(m, 1H), 3.55(d, 2H), 3.98(d, 2H), 5.60(br s, 1H), 7.40(d, 1H), 7.47(dd, 1H), 7.73(d, 1H). |
| 10 | | (CDCl$_3$): 4.46(s, 2H), 4.48(q, 2H), 4.55(d, 2H), 5.12(d, 1H), 5.20(d, 1H), 5.65(m, 1H), 7.43 (m, 3H). |
| 11 | | (CDCl$_3$): 1.23(s, 9H), 1.63(s, 9H), 4.38(s, 2H), 7.50(m, 3H). |
| 12 | | (CDCl$_3$): 0.96(t, 3H), 1.36(m, 2H), 1.72(m, 2H), 2.58(s, 3H), 3.86(t, 2H), 4.94(s, 2H), 7.39 (dd, 1H), 7.47(d, 1H), 7.73(d, 1H). |
| 13 | | (CDCl$_3$): 0.95(t, 3H), 1.35(m, 2H), 1.68(m, 2H), 3.78(t, 2H), 4.08(s, 2H), 5.63(d, 1H), 7.33 (dd, 1H), 7.56(m, 6H), 7.82(d, 2H). |
| 14 | | (CDCl$_3$): 3.88(s, 3H), 4.35(s, 2H), 4.45(br q, 2H), 7.45(m, 3H). |
| 15 | | (CDCl$_3$): 0.96(t, 3H), 1.36(m, 2H), 1.71(m, 2H), 3.84(t, 2H), 4.39(s, 2H), 5.64(s, 2H), 7.42(t, 1H), 7.47(d, 2H). |
| 16 | | (CDCl$_3$): 0.96(t, 3H), 1.36(m, 2H), 1.70(m, 2H), 3.83(t, 2H), 4.37(s, 2H), 5.84(s, 2H), 7.44 (m, 3H). |
| 17 | | (CDCl$_3$): 0.99(t, 3H), 1.42(m, 2H), 1.86(m, 2H), 4.31(t, 2H), 4.46(d, 2H), 5.00(br s, 1H), 7.52 (s, 2H), 7.80(s, 1H). |
| 18 | | (CDCl$_3$): 3.45(s, 3H), 4.39(m, 1H), 4.57(m, 1H), 5.10(d, 1H), 6.56(br, 1H), 7.47(t, 1H), 7.61 (d, 2H). |
| 19 | | (Acetone-d6): 0.95(t, 3H), 1.6(hextet, 2H), 2.75(dt, 2H), 4.3-4.8(m, 2H), 5.3(s, 1H), 7.55(d, 2H), 7.85(d, 2H). |
| 20 | | (CDCl$_3$): 2.27(s, 3H), 2.85(dd, 1H), 3.35(dd, 1H), 4.2-4.6(m, 3H), 5.95(bs, 1H), 7.39(d, 2H), 7.57(d, 2H), 8.48(s, 1H). |
| 21 | | (CDCl$_3$): 4.82(q, 2H), 7.46(d, 1H), 7.97(d, 2H), NH not resolved. |
| 23 | | (CDCl$_3$): 0.88(t, 3H), 1.32(m, 4H), 1.68(m, 2H), 3.72(br t, 2H), 4.63(s, 2H), 6.87(d, 1H), 6.99(d, 1H), 7.38(d, 2H), 7.63(d, 2H). |
| 24 | | (DMSO-d6): 4.03(s, 2H), 4.44(s, 2H), 7.79(s, 1H), 7.91(s, 1H), 10.63(bs, 1H). |
| 25 | | (CDCl$_3$): 0.82(t, 3H), 1.21(m, 2H), 1.39(m, 2H), 4.04(t, 2H), 4.31(s, 2H), 7.26(d, 1H), 7.37(t, 1H), 7.60(dt, 1H), 7.95(dd, 1H). |
| 26 | | (CDCl$_3$): 3.47(s, 3H), 4.45(dq, 2H), 4.55(dq, 2H), 5.05(d, 1H), 6.10(bs, 1H), 7.43(d, 2H), 7.64(d, 2H). |
| 27 | | (DMSO-d6): 3.22(s, 3H), 3.89(s, 2H), 7.51(d, 2H), 7.6(s, 1H), 7.75(d, 2H). |
| 28 | | (CDCl$_3$): 4.25(d, 2H), 5.10(bs, 1H), 7.27(m, 1H), 7.41(m, 4H), 7.66(m, 4H). |
| 29 | | (CDCl$_3$): 7.6(m, 3H), 7.54(t, 2H), 7.83(d, 2H), 8.15,(d, 2H), 8.60(s, 1H). |
| 30 | | (CDCl$_3$): 4.12(d, 2H), 4.95( s, 3H), 7.3-7.5(m, 7H), 7.56(d, 2H). |
| 31 | | (CDCl$_3$): 3.40(s, 3H), 4.11(d, 2H), 5.05(bs, 1H), 7.43(m, 3H), 7.64(m, 2H), |
| 32 | | (DMSO-d6): 3.84(d, 2H), 7.43(m, 3H), 7.71(m, 2H), 10.41(bs, 1H). |
| 33 | | (CDCl$_3$): 4.15(d, 2H), 4.41(q, 2H), 5.1(bs, 1H), 7.47(m, 3H), 7.65(m, 2H). |
| 34 | | (CDCl$_3$): 2.88(s, 3H), 4.03(s, 3H), 4.38(q, 2H), 7.44(s, 5H). |
| 35 | | (CDCl$_3$): 3.85(s, 3H), 4.12(d, 2H), 4.41(q, 2H), 5.0(bs, 1H), 6.94(d, 2H), 7.59(d, 2H). |
| 36 | | (CDCl$_3$): 0.96(t, 2H), 1.37(hextet, 2H), 1.70(pentet, 2H), 3.76(t, 2H), 3.84(s, 3H), 4.05(d, 2H), 4.95(bs, 1H), 6.93(d, 2H), 7.59(d, 2H). |
| 37 | | (CDCl$_3$): 4.15(s, 2H), 4.42(q, 2H), 5.12(bs, 1H), 7.37(t, 1H), 7.43(dd, 1H), 7.53(dd, 1H), 7.66 (dd, 1H). |
| 38 | | (CDCl$_3$): 0.95(t, 2H), 1.35(hextet, 2H), 1.45(d, 3H), 1.70(pentet, 2H), 3.75(t, 2H), 3.84(s, 3H), 4.05(d, 2H), 4.10(bq, 1H), 5.00(bs, 1H), 6.93(d, 2H), 7.60(d, 2H). |
| 39 | | (CDCl$_3$): 3.88(s, 3H), 4.75(q, 2H), 6.98(d, 2H), 8.09(d, 2H), 8.53(s, 1H). |
| 40 | | (CDCl$_3$): 1.84(s, 3H), 4.48(q, 2H), 7.47(d, 2H), 7.58(d, 2H). |
| 41 | | (CDCl$_3$): 2.39(s, 3H), 4.13(d, 2H), 4.41(q, 2H), 5.05(bs, 1H), 7.22(d, 2H), 7.54(d, 2H). |
| 42 | | (CDCl$_3$): 2.93(s, 3H), 4.39(d, 2H), 4.53(q, 2H), 7.42(d, 2H), 7.74(d, 2H). |
| 43 | | (CDCl$_3$): 4.15(d, 2H), 4.40(q, 2H), 5.05(bs, 1H), 7.46(t, 1H), 7.54(d, 2H). |
| 44 | | (CDCl$_3$): 3.54(s, 2H), 3.89(d, 2H), 4.32(q, 2H), 4.40(bs, 1H), 7.25-7.37(m, 5H). |
| 45 | | (CDCl$_3$): 1.1-1.4(m, 5H), 1.6-1.9(m, 5H), 2.1(m, 1H), 3.97(d, 2H), 4.28(q, 2H), 4.5(bs, 1H). |
| 46 | | (CDCl$_3$): 3.84(s, 3H), 4.12(d, 2H), 4.41(q, 2H), 5.15(bs, 1H), 7.01(ddd, 1H), 7.18(m, 2H), 7.35(t, 1H). |
| 47 | | (CDCl$_3$): 2.50(s, 3H), 4.14(d, 2H), 4.40(q, 2H), 5.0(bs, 1H), 7.57(s, 2H). |
| 48 | | (CDCl$_3$): 0.93(t, 2H), 1.1-1.4(m, 6H), 1.55-1.9(m, 7H), 2.15(m, 1H), 3.65(t, 2H), 3.89(s, 2H), 4.45(bs, 1H), 7.43(d, 2H), 8.10(d, 2H), 8.43(s, 1H). |
| 49 | | (CDCl$_3$): 0.91(t, 2H), 1.35(m, 4H), 1.72(pentet, 2H), 2.49(s, 3H), 3.76(t, 2H), 4.06(d, 2H), 5.05(bs, 1H), 7.58(s, 1H). |
| 50 | | (CDCl$_3$): 0.96(t, 3H), 1.38(hextet, 2H), 1.72(pentet, 2H), 3.78(t, 2H), 4.07(d, 2H), 4.95(bs, 1H), 7.41(d, 2H), 7.59(d, 2H). |
| 51 | | (CDCl$_3$): 4.19(d, 2H), 4.42(q, 2H), 5.10(bs, 1H), 7.70(d, 2H), 7.9(d, 2H). |
| 52 | | (CDCl$_3$): 4.18(d, 2H), 4.43(q, 2H), 6.80(bs, 1H), 7.36(m, 1H), 7.76(dt, 1H), 8.08(d, 1H), 8.53 (m, 1H). |

TABLE 3-continued

Spectral Characterization for Compounds 1=292

| # | HPLC/MS | NMR DATA(300 MHZ) |
|---|---|---|
| 53 | | (CDCl$_3$): 4.3-4.7(m, 2H), 5.20(d, 1H), 5.6(m, 1H), 7.35(m, 1H), 7.75(t, 1H), 7.8(bs, 1H), 8.11 (d, 1H), 8.55(d, 1H). |
| 54 | | (CDCl$_3$): 0.91(t, 3H), 1.35(m, 4H), 1.73(m, 2H), 3.76(t, 2H), v4.07(s, 2H), 5.00(bs, 1H), 7.41 (d, 2H), 7.56(d, 2H). |
| 55 | | (CDCl$_3$): 0.89(t, 2H), 1.32(m, 4H), 1.73(pentet, 2H), 1.86(m, 2H), 3.77(t, 2H), 4.08(s, 2H), 5.15(bs, 1H), 7.40(d, 2H), 7.60(d, 2H). |
| 56 | | (CDCl$_3$): 0.87(t, 2H), 1.2-1.45(m, 8H), 1.5-1.9(m, 4H), 3.76(t, 2H), 4.08(s, 2H), 4.95(bs, 1H), 7.40(d, 2H), 7.60(d, 2H). |
| 57 | | (CDCl$_3$): 0.87(t, 2H), 1.2-1.45(m, 12H), 1.6-1.9(m, 4H), 3.76(t, 2H), 4.06(s, 2H), 5.15(bs, 1H), 7.39(d,2H), 7.61(d, 2H). |
| 58 | | (CDCl$_3$): 2.39(s, 3H), 4.23(d, 2H), 5.10(bs, 1H), 7.08(d, 1H), 7.30(t, 1H), 7.41(m, 4H), 7.65 (d, 2H). |
| 59 | | (CDCl$_3$): 4.23(d, 2H), 5.45(bs, 1H), 7.26(m, 1H), 7.36(d, 2H), 7.57(d, 1H), 7.65(d, 2H), 7.79 (m, 1H), 8.58(m, 1H). |
| 60 | | (CDCl$_3$): 4.16(d, 2H), 4.70(s, 2H), 5.10(bs, 1H), 7.43(d, 2H), 7.62(d, 2H). |
| 61 | | (CDCl$_3$): 0.14(s, 9H), 3.39(s, 2H), 4.08(s, 2H), 5.16(br s, 1H), 7.39(dt, 2H), 7.60(dt, 2H). |
| 62 | | (CDCl$_3$): 4.09(d, 2H), 4.98(s, 2H + NH), 6.76(d, 1H), 6.89(d, 1H), 7.41(dt, 2H), 7.61(dt, 2H). |
| 63 | | (CDCl$_3$): 3.93(s, 2H), 4.29(s, 2H), 4.93(s, 2H), 6.61(d, 1H), 6.73(d, 1H), 6.76(d, 1H), 6.84(d, 1H), 7.45(d, 2H), 7.50(d, 2H). |
| 64 | | (DMSO-d6): 3.89(s, 2H), 7.56(s, 1H), 7.66(s, 1H), 7.75(s, 2H), 10.58(s, 1H). |
| 65 | | (CDCl$_3$): 4.15(s, 2H), 4.56(s, 2H), 5.01(br s, 1H), 5.40(s, 2H), 7.44(m, 1H), 7.55(m, 2H). |
| 66 | | (CDCl$_3$): 3.66-3.95(m, 4H), 4.32(d, 1H), 4.57(dd, 1H), 5.69-6.31(m, 4H), 7.41(s, 4H). |
| 67 | | (CDCl$_3$): 4.09(s, 2H), 4.36(d, 1H), 4.61(d, 1H), 5.12(br s, 1H), 5.98(dt, 1H, cis isomer), 6.09 (dt, 1H, trans isomer), 6.23(dd, 1H, cis isomer), 6.31(dd, 1H, trans isomer), 7.39(dd, 2H), 7.60 (dd, 2H). |
| 68 | | (CDCl$_3$): 0.95(t, 3H), 1.35(hextet, 2H), 1.65(pentet, 2H), 2.72(s, 3H), 3.72(t, 2H), 4.05(d, 2H), 4.95(bs, 1H). |
| 69 | | (CDCl$_3$): 0.96(t, 3H), 1.39(hextet, 2H), 1.71(pentet, 2H), 3.76(t, 2H), 4.07(d, 2H), 5.17(br s, 1H), 7.21(q, 1H), 7.39(m, 1H), 7.58(dt, 1H). |
| 70 | | (DMSO-d6): 4.01(s, 2H), 4.41(q, 2H), 7.59(s, 2H), 7.76(s, 1H), NH not resolved. |
| 71 | | (CDCl$_3$): 3.78(s, 3H), 3.85(s, 2H), 4.07(s, 2H), 4.38(q, 2H), 7.37(d, 1H), 7.46(t, 2H). |
| 72 | | (CDCl$_3$): 1.92(s, 3H), 4.48(q, 2H), 4.50(s, 2H), 7.51(m, 3H). |
| 73 | | (CDCl$_3$): 4.12(s, 2H), 4.38(q, 2H), 5.07(br s, 1H), 7.33(dd, 1H), 7.47(d, 1H), 7.51(d, 1H). |
| 74 | | (CDCl$_3$): 0.96(t, 3H), 1.38(hextet, 2H), 1.69(pentet, 2H), 3.74(t, 2H), 4.04(s, 2H), 5.09(br s, 1H), 7.36(s, 2H), 7.55(s, 1H). |
| 75 | | (CDCl$_3$): 0.91(t, 3H), 1.32(m, 2H), 1.67(m, 2H), 2.02(s, 3H), 2.33(s, 3H), 3.69(m, 2H), 4.85 (broad s, 0.5 H), 4.94(s, 1H), 7.17(d, 2H), 7.23(d, 2H). |
| 76 | | (CDCl$_3$): 0.92(t, 3H), 1.35(dt, 2H), 1.69(m, 2H), 1.99(s, 3H), 3.70(m, 2H), 4.76(broad s, 0.7 H), 5.26(s, 1H), 7.21(m, 4H). |
| 77 | | (CDCl$_3$): 0.91(t, 3H), 1.35(dt, 2H), 1.66(m, 2H), 2.02(s, 3H), 2.35(s, 3H), 3.66(t, 2H), 4.87 (broad s, 0.6 H), 4.91(s, 1H), 7.14(m, 1H), 7.15(s, 2H), 7.27(m, 1H). |
| 78 | | (CDCl$_3$): 0.91(t, 3H), 1.32(dt, 2H), 1.66(m, 2H), 2.02(s, 3H), 3.66(t, 2H), 4.88(broad s, 0.7 H), 4.84(s, 1H), 6.62(d, 1H), 6.64(s, 1H), 6.70(d, 1H), 7.1(t, 1H). |
| 79 | | (CDCl$_3$): 0.92(t, 3H), 1.34(dt, 2H), 1.65(m, 2H), 2.03(s, 3H), 3.80(s, 3H), 3.65(m, 2H), 4.80 (broad s, 0.5 H), 4.88(s, 1H), 6.89(d, 2H), 7.26(d, 2H). |
| 80 | | (CDCl$_3$): 0.90(t, 3H), 1.33(dt, 2H), 1.68(m, 2H), 2.04(s, 3H), 3.80(s, 3H), 3.64(m, 2H), 4.88 (broad s, 0.7 H), 4.96(s, 1H), 6.90(m, 3H), 7.28(m, 1H). |
| 81 | | (CDCl$_3$): 0.60(t, 3H), 0.96(dt, 2H), 1.30(m, 2H), 1.63(s, 3H), 3.25(m, 2H), 4.45(s, 1H), 5.70(s, 1H), 6.99(d, 2H). |
| 82 | | (CDCl$_3$): 0.83(t, 3H), 1.23(m, 2H), 1.50(m, 2H), 1.63(s, 3H), 2.14(s, 9H), 3.32(m, 1H), 3.48 (m, 1H), 5.20(s, 1H), 5.33(s, 1H), 6.70(s, 2H). |
| 83 | | (CDCl$_3$): 0.96(t, 3H), 1.39(m, 2H), 1.71(m, 2H), 3.81(t, 2H), 4.11(d, 2H), 5.25(br s, 1H), 6.90 (t, 1H), 7.01(dd, 1H), 7.21(dd, 1H), 7.34(dt, 1H), 11.75(br s, 1H). |
| 84 | | (CDCl$_3$): 4.16(d, 2H), 4.41(q, 2H), 5.07(br s, 1H), 7.17(m, 1H), 7.40(m, 3H). |
| 85 | | (CDCl$_3$): 0.97(t, 3H), 1.40(m, 2H), 1.73(m, 2H), 3.88(t, 2H), 3.92(d, 3H), 4.48(s, 2H), 7.38 (dd, 1H), 7.52(d, 1H), 7.68(d, 1H). |
| 86 | | (CDCl$_3$): 0.41(m, 2H), 0.53(m, 2H), 1.29(m, 1H), 3.67(d, 2H), 4.14(d, 2H), 5.01(br s, 1H), 7.56(t, 1H), 7.71(d, 1H), 7.87(d, 1H), 7.93(s, 1H). |
| 87 | | (CDCl$_3$): 2.27(t, 1H), 2.46(t, 1H), 3.83(d, 2H), 4.10(s, 2H), 4.56(d, 2H), 7.60(t, 1H), 7.74(d, 1 H), 7.80(d, 1H), 7.90(s, 1H). |
| 88 | | (CDCl$_3$): 2.28(t, 1H), 4.15(d, 2H), 4.59(d, 2H), 5.04(br, 1H), 7.57(t, 1H), 7.72(d, 1H), 7.89(d, 1H), 7.92(d, 1H). |
| 89 | | (CDCl$_3$): 2.49(t, 1H), 3.86(d, 2H), 4.12(s, 2H), 4.38(q, 2H), 7.61(t, 1H), 7.78(t, 2H), 7.89(s, 1H). |
| 90 | | (CDCl$_3$): 4.22(s, 2H), 4.44(q, 2H), 5.18(broad s, 1H), 7.97(s, 1H), 8.12(s, 2H). |
| 91 | | (CDCl$_3$): 4.12(s, 2H), 4.42(q, 2H), 5.55(d, 2H), 6.44(t, 1H), 7.61(t, 1H), 7.78(m, 3H). |
| 92 | | (CDCl$_3$): 1.00(t, 3H), 1.43(dt, 2H), 1.67(m, 2H), 2.04(s, 3H), 3.61(m, 2H), 4.87(broad s, 0.5 H), 5.00(s, 1H),, 7.28(d, 5H). |
| 93 | | (CDCl$_3$): 0.80(t, 3H), 1.42(dt, 2H), 1.65(m, 2H), 2.03(s, 3H), 3.65(m, 2H), 4.87(broad s, 0.8 H), 4.97(s, 1H), 7.05(dd, 2H), 7.31(dd, 2H). |
| 94 | | (CDCl$_3$): 0.91(t, 3H), 1.35(dt, 2H), 1.68(m, 2H), 2.03(s, 3H), 2.28(s, 3H), 3.70(t, 2H), 4.84 (broad s, 0.7 H), 4.94(s, 1H), 7.00(m, 1H), 7.16(m, 2H). |
| 95 | | (CDCl$_3$): 0.89(t, 3H), 1.36(s, 9H), 1.41(m, 2H), 1.74(m, 2H), 1.98(s, 3H), 3.66(t, 2H), 4.85 (broad s, 0.5 H), 4.94(s, 1H), 7.26(d, 2H), 7.38(d, 2H). |

TABLE 3-continued

Spectral Characterization for Compounds 1=292

| # | HPLC/MS | NMR DATA(300 MHZ) |
|---|---|---|
| 96 | | (CDCl$_3$): 4.14(s, 2H), 4.41(q, 2H), 5.56(br d, 1H), 7.13(dd, 1H), 7.24(m, 1H), 7.44(dddd, 1H), 7.86(td, 1H). |
| 97 | | (CDCl$_3$): 4.14(s, 2H), 4.40(q, 2H), 5.04(br s, 1H), 7.40(m, 3H), 7.57(d, 1H). |
| 98 | | (CDCl$_3$): 4.15(d, 2H), 4.40(q, 2H), 5.02(bs, 1H), 7.24(m, 1H), 7.37(m, 1H), 7.56(m, 1H). |
| 99 | | (CDCl$_3$): 4.16(d, 2H), 4.40(q, 2H), 5.03(br s, 1H), 7.50(s, 2H), 7.76(m, 1H). |
| 100 | | (CDCl$_3$): 1.29(t, 3H), 3.83(q, 2H), 4.08(d, 2H), 4.94(br s, 1H), 7.50(d, 2H), 7.78(s, 1H). |
| 101 | | (CDCl$_3$): 0.96(t, 3H), 1.37(hextet, 2H), 1.71(pentet, 2H), 3.77(t, 2H), 4.07(s, 2H), 5.24(br s, 1H), 7.50(s, 2H), 7.79(d, 1H). |
| 102 | | (CDCl$_3$): 1.31(t, 3H), 4.15(d, 2H), 4.25(q, 2H), 4.52(s, 2H), 5.17(br s, 1H), 7.45(m, 2H), 7.74(m, 1H). |
| 103 | | (CDCl$_3$): 4.11(d, 2H), 4.94(s, 2H), 4.96(br s, 1H), 7.33(m, 3H), 7.45(m, 4H), 7.72(d, 1H). |
| 104 | | (CDCl$_3$): 0.96(t, 3H), 1.38(hextet, 2H), 1.71(pentet, 2H), 3.77(t, 2H), 4.08(d, 2H), 5.00(br s, 1 H), 7.43(t, 1H), 7.55(d, 2H). |
| 105 | | (DMSO-d6): 2.40(s, 3H), 4.40(m, 1H), 4.71(m, 1H), 5.54(br s, 1H), 7.28(m, 2H), 7.36(m, 1H), 7.48(d, 1H), 8.88(br s, 1H), 12.10(s, 1H). |
| 106 | | (CDCl$_3$): 0.96(t, 3H), 1.40(hextet, 2H), 1.71(pentet, 2H), 3.77(t, 2H), 4.08(s, 2H), 4.99(br s, 1H), 7.22(t, 1H), 7.53(m, 1H), 7.75(dd, 1H). |
| 107 | | (CDCl$_3$): 0.95(t, 3H), 1.75(hextet, 2H), 3.73(t, 2H), 4.07(d, 2H), 5.45(br s, 1H), 7.42(t, 1H), 7.58(d, 2H). |
| 108 | | (CDCl$_3$): 1.20(t, 3H), 3.56(q, 2H), 3.75(t, 2H), 3.99(t, 2H), 4.10(s, 2H), 5.01(br s, 1H), 7.42(t, 1H), 7.54(d, 2H). |
| 109 | | (CDCl$_3$): 0.37(m, 2H), 0.52(m, 2H), 1.26(m, 1H), 3.63(d, 2H), 4.08(d, 2H), 5.59(br s, 1H), 7.41(t, 1H), 7.59(d, 2H). |
| 110 | | (CDCl$_3$): 0.96(t, 3H), 1.38(hextet, 2H), 1.72(pentet, 2H), 3.77(t, 2H), 4.07(d, 2H), 5.14(br s, 1H), 7.33(dd, 1H), 7.42(dt, 1H), 7.53(dt, 1H), 7.68(t, 1H). |
| 111 | | (CDCl$_3$): 4.21(d, 2H), 5.25(br s, 1H), 7.37(m, 5H), 7.57(dd, 1H), 7.64(dd, 2H), 7.72(t, 1H). |
| 112 | | (CDCl$_3$): 2.40(s, 3H), 4.23(d, 2H), 5.18(br s, 1H), 7.11(d, 1H), 7.36(m, 5H), 7.58(dt, 1H), 7.71(t, 1H). |
| 113 | | (CDCl$_3$): 4.48(q, 2H), 4.49(s, 2H), 4.56(br d, 2H), 7.02(dd, 1H), 7.45(m, 3H). |
| 114 | 91%, 262 (M + H) | |
| 115 | 86%, 300 (M + H) | |
| 116 | 71%, 298 (M + Na) | |
| 117 | 91%, 322 (M + Na) | |
| 118 | | |
| 119 | | (CDCl$_3$): 0.97(t, 3H), 1.42(m, 2H), 1.77(m, 2H), 3.83(t, 2H), 4.11(s, 2H), 5.20(bs, 1H), 7.54 (m, 2H), 7.85(m, 4H), 8.04(s, 1H). |
| 120 | 80%, 440 (M + Na) | |
| 121 | 79%, 323 (M + Na) | |
| 122 | 89%, 257 (GC/MS) | |
| 123 | | (CDCl$_3$): 3.48(br s, 3H), 4.51(q, 2H), 4.55(s, 2H), 7.45(d, 2H), 7.49(t, 1H). |
| 124 | 93%, 248 (M + Na) | |
| 125 | | (CDCl$_3$): 1.31(t, 3H), 4.11(s, 2H), 4.24(c, 2H), 4.50(s, 2H), 5.50(bs, 1H), 7.15(m, 1H), 7.35 (m, 1H), 7.45(m, 1H). |
| 126 | | (CDCl$_3$): 3.51(t, 2H), 3.55(t, 2H), 4.06(s, 2H), 4.39(q, 2H), 7.41(d, 2H), 7.48(s, 1H). |
| 127 | | (CDCl$_3$): 0.97(t, 3H), 1.37(m, 2H), 1.71(m, 2H), 3.84(t, 2H), 4.40(s, 2H), 4.55(br d, 2H), 7.04 (dd, 1H), 7.43(t, 1H), 7.46(d, 2H). |
| 128 | | (CDCl$_3$): 4.11(d, 2H), 4.39(d, 2H), 5.06(br s, 1H), 5.23(dd, 1H), 5.29(dd, 1H), 5.95(m, 1H), 7.42(t, 1H), 7.55(d, 2H). |
| 129 | | (CDCl$_3$): 0.96(t, 3H), 1.36(m, 2H), 1.71(m, 2H), 2.34(s, 3H), 3.84(t, 2H), 4.42(s, 2H), 7.42(t, 1H), 7.48(d, 2H). |
| 130 | | (CDCl$_3$): 0.96(t, 3H), 1.36(m, 2H), 1.70(m, 2H), 3.69(s, 3H), 3.83(t, 2H), 4.35(s, 2H), 7.41(t, 1H), 7.44(d, 2H). |
| 131 | | (CDCl$_3$): 0.95(t, 3H), 1.36(m, 2H), 1.68(m, 2H), 2.45(t, 1H), 3.74(t, 2H), 3.82(d, 2H), 4.02(s, 2H), 7.47(m, 3H). |
| 132 | | (CDCl$_3$): 0.89(t, 3H), 1.29(m, 2H), 1.63(m, 2H), 3.75(t, 2H), 4.29(s, 2H), 4.47(d, 2H), 5.05(d, 1H), 5.12(dd, 1H), 5.59(m, 1H), 7.32(t, 1H), 7.37(d, 2H). |
| 133 | | (CDCl$_3$): 0.96(t, 3H), 1.36(m, 2H), 1.71(m, 2H), 2.53(t, 1H), 3.83(t, 2H), 4.38(s, 2H), 4.65(d, 2H), 7.41(t, 1H), 7.46(d, 2H). |
| 134 | | (CDCl$_3$): 1.78(s, 3H), 4.47(s, 2H), 4.49(q, 2H), 4.63(d, 1H), 4.65(d, 1H), 7.45(t, 1H), 7.48(d, 2H). |
| 135 | | (CDCl$_3$): 0.97(t, 3H), 1.39(m, 2H), 1.72(m, 2H), 1.78(s, 3H), 3.85(t, 2H), 4.38(s, 2H), 4.63(d, 2H), 7.42(t, 1H), 7.48(d, 2H). |
| 136 | | (CDCl$_3$): 0.97(t, 3H), 1.37(m, 2H), 1.71(m, 2H), 3.84(t, 2H), 4.40(s, 2H), 4.54(br d, 2H), 7.03 (dd, 1H), 7.39(dd, 1H), 7.49(d, 1H), 7.71(d, 1H). |
| 137 | | (CDCl$_3$): 4.50(q, 2H), 4.54(s, 2H), 5.65(dd, 1H), 5.85(dd, 1H), 6.38(dd, 1H), 7.47(m, 3H). |
| 138 | | (CDCl$_3$): 0.97(t, 3H), 1.37(m, 2H), 1.71(m, 2H), 3.85(t, 2H), 4.46(s, 2H), 5.63(dd, 1H), 5.87 (dd, 1H), 6.38(dd, 1H), 7.44(m, 1H), 7.48(m, 2H). |

TABLE 3-continued

Spectral Characterization for Compounds 1=292

| # | HPLC/MS | NMR DATA(300 MHZ) |
|---|---|---|
| 139 | | (CDCl$_3$): 4.04(s, 2H), 4.92(s, 2H), 5.30(bs, 1H), 7.10-7.60(m, 8H). |
| 140 | | (CDCl$_3$): 1.29(t, 3H), 4.09(s, 2H), 4.22(c, 2H), 4.50(s, 2H), 5.50(bs, 1H), 6.47(bs, 1H), 6.80 (bs, 1H), 7.45(s, 1H). |
| 141 | 93%, 309 (M + H) | |
| 142 | 100%, 379 (M + H) | |
| 143 | 100%, 308 (M + H) | |
| 144 | 100%, 342 (M + H) | |
| 145 | 100%, 316 (M + H) | |
| 146 | 100%, 334 (M + H) | |
| 147 | 100%, 304 (M + H) | |
| 148 | 100%, 236 (M + H) | |
| 149 | 100%, 276 (M + H) | |
| 150 | 100%, 286 (M + H) | |
| 151 | 89%, 290 (M + H) | |
| 152 | 100%, 248 (M + H) | |
| 153 | 100%, 326 (M + H) | |
| 154 | 100%, 272 (M + H) | |
| 155 | 100%, 330 (M + H) | |
| 156 | 98%, 282 (M + H) | |
| 157 | 100%, 317 (M + H) | |
| 158 | 86%, 444 (M + H) | |
| 159 | 100%, 327 (M + H) | |
| 160 | 93%, 301 (M + H) | |
| 161 | 100%, 330 (M + H) | |
| 162 | | (DMSO-d6): 0.97(t, 3H), 1.36(m, 2H), 1.68(m, 2H), 3.70(t, 2H), 3.99(s, 2H), 7.45(m, 1H&NH), 7.97(m, 4H). |
| 163 | | (DMSO-d6): 4.10(s, 2H), 4.52(q, 2H), 7.46(m, 1H&NH), 7.98(m, 4H). |
| 164 | | (CDCl$_3$): 0.96(t, 3H), 1.76(m, 2H), 3.74(t, 2H), 4.08(d, 2H), 4.92(br s, 1H), 7.49(s, 1H), 7.77 (s, 1H). |
| 165 | 83%, 276 (M + H) | |
| 166 | 85%, 350 (M + H) | |
| 167 | | (CDCl$_3$): 4.22(s, 2H), 4.43(c, 2H), 5.25(bs, 1H), 7.64(dxd, 1H), 8.06(d, 1H), 8.32(d, 1H), 8.49 (s, 1H). |
| 168 | | (CDCl$_3$): 0.95(t, 3H), 1.36(m, 2H), 1.68(m, 2H), 2.44(t, 1H), 3.74(t, 2H), 3.83(d, 2H), 4.02(s, 2H), 7.43(dd, 1H), 7.53(d, 1H), 7.68(d, 1H). |
| 169 | | (CDCl$_3$): 2.49(t, 1H), 3.86(d, 2H), 4.09(s, 2H), 4.37(q, 2H), 7.49(m, 3H). |
| 170 | | (CDCl$_3$): 0.97(t, 3H), 1.38(m, 2H), 1.72(m, 2H), 1.78(s, 3H), 3.84(t, 2H), 4.37(s, 2H), 4.63(d, 2H), 7.44(dd, 1H), 7.49(d, 1H), 7.70(d, 1H). |
| 171 | | (CDCl$_3$): 0.96(t, 3H), 1.37(m, 2H), 1.71(m, 2H), 2.48(t, 1H), 3.83(t, 2H), 4.38(s, 2H), 4.64(d, 2H), 7.41(dd, 1H), 7.48(d, 1H), 7.67(d, 1H). |
| 172 | | (CDCl$_3$): 0.96(t, 3H), 1.38(m, 2H), 1.71(m, 2H), 3.83(t, 2H), 4.36(s, 2H), 4.54(d, 2H), 5.11(d, 1H), 5.18(d, 1H), 5.67(m, 1H), 7.39(dd, 1H), 7.47(d, 1H), 7.66(d, 1H). |
| 173 | | (CDCl$_3$): 0.98(t, 3H), 1.39(m, 2H), 1.75(m, 2H), 3.88(t, 2H), 4.46(s, 2H), 6.90(d, 2H), 7.19 (dd, 1H), 7.31(dd, 1H), 7.50(s, 2H), 7.79(s, 1H). |
| 174 | | (DMSO-d6): 3.85(d, 2H), 7.50(br s, 1H), 7.70(d, 2H), 7.94(t, 1H), 10.51(br s, 1H). |
| 175 | | (CDCl$_3$): 0.97(t, 3H), 1.40(m, 2H), 1.72(m, 2H), 3.79(t, 2H), 4.11(d, 2H), 5.02(br s, 1H), 7.55 (t, 1H), 7.74(dt, 1H), 7.89(dt, 1H), 8.00(t, 1H). |
| 176 | | (CDCl$_3$): 3.83(s, 2H), 4.27(d, 2H), 6.72(br s, 1H), 7.60(t, 1H), 7.81(d, 1H), 8.05(d, 1H), 8.12 (t, 1H). |
| 177 | | (CDCl$_3$): 0.96(t, 3H), 1.37(m, 2H), 1.70(dd, 3H), 1.71(m, 2H), 3.84(t, 2H), 4.42(s, 2H), 5.60 (d, 1H), 6.94(dq, 1H), 7.39(dd, 1H), 7.49(d, 1H), 7.73(d, 1H). |
| 178 | | (CDCl$_3$): 0.98(t, 3H), 1.40(m, 2H), 1.76(m, 2H), 3.90(t, 2H), 4.89(s, 2H), 6.77(d, 2H), 7.23(d, |

TABLE 3-continued

Spectral Characterization for Compounds 1=292

| # | HPLC/MS | NMR DATA(300 MHZ) |
|---|---|---|
| | | 1H), 7.32(t, 2H), 7.52(s, 2H), 7.79(s, 1H). |
| 179 | | (CDCl$_3$): 0.96(t, 3H), 1.37(m, 2H), 1.75(m, 2H), 3.47(br t, 2H), 3.83(t, 2H), 4.31(t, 2H), 4.37 (s, 2H), 7.41(dd, 1H), 7.49(d, 1H), 7.69(d, 1H). |
| 180 | | (CDCl$_3$): 0.95(t, 3H), 1.17(t, 3H), 1.36(m, 2H), 1.68(m, 2H), 2.24(qt, 2H), 3.73(t, 2H), 3.78(t, 2H), 4.00(s, 2H), 7.42(dd, 1H), 7.52(d, 1H), 7.72(d, 1H). |
| 181 | | (CDCl$_3$): 0.69(m, 2H), 0.96(m, 1H), 0.97(t, 3H), 1.06(m, 2H), 1.39(m, 2H), 1.74(m, 2H), 3.86 (t, 2H), 4.42(s, 2H), 7.51(m, 2H), 7.79(d, 1H). |
| 182 | | (CDCl$_3$): 0.95(t, 3H), 1.35(m, 2H), 1.67(m, 2H), 3.73(t, 2H), 3.88(s, 2H), 4.28(s, 2H), 7.12(d, 2H), 7.35(m, 4H), 7.49(d, 1H), 7.65(d, 1H). |
| 183 | | (CDCl$_3$): 0.94(t, 3H), 1.36(m, 2H), 1.68(m, 2H), 1.87(t, 3H), 3.73(t, 2H), 3.76(q, 2H), 4.01(s, 2H), 7.42(dd, 1H), 7.52(d, 1H), 7.70(d, 1H). |
| 184 | 91%, 311 (M + H) | |
| 185 | 85%, 267 (M + H) | |
| 186 | 90%, 342 (M + H) | |
| 187 | 90%, 312 (M + H) | |
| 188 | 90%, 365 (M + H) | |
| 189 | 92%, 308 (M + H) | |
| 190 | 90% 335 (M + H) | |
| 191 | | (CDCl$_3$): 0.96(t, 3H), 1.36(m, 2H), 1.72(m, 2H), 3.86(t, 2H), 4.92(s, 2H), 5.16(d, 1H), 5.23 (dd, 1H), 5.72(m, 1H), 7.39(dd, 1H), 7.47(d, 1H), 7.70(d, 1H). |
| 192 | | (CDCl$_3$): 0.96(t, 3H), 1.37(m, 2H), 1.72(m, 2H), 2.21(t, 1H), 3.87(t, 2H), 3.94(d, 2H), 4.93(s, 2H), 7.40(dd, 1H), 7.48(d, 1H), 7.71(d, 1H). |
| 193 | | (CDCl$_3$): 3.45(s, 3H), 4.39(m, 1H), 4.57(m, 1H), 5.10(d, 1H), 6.56(br, 1H), 7.47(t, 1H), 7.61 (d, 2H). |
| 194 | | (CDCl$_3$): 0.99(t, 3H), 1.40(m, 2H), 1.75(m, 2H), 3.88(t, 2H), 4.47(s, 2H), 6.90(d, 2H), 7.22 (dd, 1H), 7.33(m, 2H), 7.42(t, 1H), 7.56(d, 2H). |
| 195 | | (CDCl$_3$): 0.95(t, 3H), 1.39(m, 2H), 1.72(m, 2H), 3.77(t, 2H), 3.91(s, 3H), 4.02(d, 2H), 6.21(br s, 1H), 6.96(d, 1H), 7.03(dt, 1H), 7.39(ddd, 1H), 7.89(dd, 1H). |
| 196 | | (CDCl$_3$): 2.22(quintet, 2H), 3.62(t, 2H), 3.94(t, 2H), 4.09(d, 2H), 5.03(br s, 1H), 7.50(d, 2H), 7.77(t, 1H). |
| 197 | | (CDCl$_3$): 0.91(t, 3H), 1.36(m, 4H), 1.73(m, 2H), 3.75(t, 2H), 4.08(d, 2H), 4.94(br s, 1H), 7.49 (s, 2H), 7.77(s, 1H). |
| 198 | | (CDCl$_3$): 1.31(t, 3H), 4.16(s, 2H), 4.24(q, 2H), 6.90(1H, br s), 7.29-7.49(m, 4H). |
| 199 | | (CDCl$_3$): 0.94(t, 3H), 1.34(m, 2H), 1.65(m, 2H), 3.71(t, 2H), 3.80(s, 3H), 3.85(s, 2H), 4.21(s, 2H), 6.86(d, 2H), 7.03(d, 2H), 7.37(dd, 1H), 7.50(d, 1H), 7.64(d, 1H). |
| 200 | | (CDCl$_3$): 0.95(t, 3H), 1.35(m, 2H), 1.67(m, 2H), 3.76(m, 2H), 3.77(s, 6H), 3.89(s, 2H), 4.20 (s, 2H), 6.25(d, 2H), 6.38(t, 1H), 7.37(dd, 1H), 7.50(d, 1H), 7.63(d, 1H). |
| 201 | | (CDCl$_3$): 0.95(t, 3H), 1.36(m, 2H), 1.54(m, 2H), 1.67(m, 3H), 1.86(m, 1H), 1.97(m, 2H), 2.53 (m, 1H), 3.09(d, 2H), 3.73(t, 2H), 3.89(s, 2H), 7.31(dd, 1H), 7.52(d, 1H), 7.57(d, 1H). |
| 202 | | (CDCl$_3$): 0.93(t, 3H), 1.34(dt, 2H), 1.67(quintet, 2H), 3.74(t, 1H), 4.58(m, 1H), 5.29(d, 1H), 5.34(m, 1H), 5.86(s, 1H), 5.97(m, 1H), 7.48(d, 1H), 7.62(dd, 1H), 7.86(d, 1H). |
| 203 | | (CDCl$_3$): 0.92(t, 3H), 1.34(m, 2H), 1.70(quintet, 2H), 1.79(s, 3H), 3.70(m, 1H), 3.77(m, 1H), 4.50(d, 1H), 4.97(s, 2H), 5.74(m, 1H), 7.46(d, 1H), 7.56(dd, 1H), 7.82(d, 1H). |
| 204 | | (CDCl$_3$): 0.93(t, 3H), 1.37(dt, 2H), 1.58(quintet, 2H), 2.21(t, 2H), 4.00(s, 2H), 4.95(broad s, 1H), 7.33(d, 2H), 7.56(d, 2H). |
| 205 | | (CDCl$_3$): 2.49(t, 2H), 2.92(t, 2H), 3.85,(s, 2H), 4.24(m, 3H), 7.26(m, 5H). |
| 206 | | (Methanol-d4): 1.00(t, 2H), 1.43(t, 3H), 1.43(m, 2H), 1.75(quintet, 2H), 3.79(t, 2H), 4.03(s, 2H), 4.41(q, 2H), 7.83(m, 6H), 8.13(d, 2H). |
| 207 | | (CDCl$_3$): 0.96(t, 3H), 1.38(dt, 2H), 1.68(quintet, 2H), 3.77(t, 2H), 4.06(s, 2H), 5.12(broad s, 1H), 7.16(t, 1H), 7.58(m, 1H), 7.89(dd, 1H). |
| 208 | | (Methanol-d4): 4.22(s, 2H), 4.59(q, 2H), 7.45(t, 1H), 7.90(m, 1H), 8.16(dd, 1H). |
| 209 | | (CDCl$_3$): 1.13(t, 3H), 1.18(t, 3H), 2.22(m, 4H), 3.80(t, 2H), 4.04(s, 2H), 4.50(t, 2H), 7.46(dd, 1H), 7.52(d, 1H), 7.75(d, 1H). |
| 210 | | (DMSO-d6): 1.04(t, 3H), 2.18(q, 2H), 3.94(br s, 2H), 4.40(s, 2H), 7.74(s, 2H), 7.98(s, 1H), NH not resolved. |
| 211 | | (CDCl$_3$): 0.93(t, 3H), 1.34(m, 2H), 1.68(m, 2H), 3.73(t, 2H), 4.01(d, 2H), 6.02(br s, 1H), 7.26 (t, 1H), 7.53(dt, 1H), 7.62(d, 1H), 7.85(t, 1H). |
| 212 | | (CDCl$_3$): 4.08(d, 2H), 4.38(q, 2H), 5.62(br s, 1H), 7.28(t, 1H), 7.58(dd, 2H), 7.80(t, 1H). |
| 213 | | (CDCl$_3$): 0.94(t, 3H), 1.37(m, 2H), 1.70(m, 2H), 3.75(t, 2H), 3.82(d, 2H), 5.12(s, 2H), 6.17(br s, 1H), 7.03(dt, 2H), 7.36(m, 6H), 7.87(dd, 1H). |
| 214 | | (CDCl$_3$): 1.06(t, 3H), 3.65,(s, 3H), 4.2(m, 3H), 4.77(dq, 1H), 5.74(s, 1H), 7.38(d, 2H), 7.45(t, 1H). |
| 215 | | (Acetone-d6): 2.76(t, 1H), 3.10(t, 1H), 4.11(d, 2H), 4.11(s, 2H), 4.52(d, 2H), 7.68(dd, 1H), 7.76(d, 1H), 7.86(d, 1H). |
| 216 | | (Acetone-d6): 2.79(t, 1H), 4.10(s, 2H), 4.58(d, 2H), 7.09(broad s, 1H), 7.73(d, 1H), 7.84(dd, 1H), 8.06(d, 1H). |
| 217 | | (CDCl$_3$): 2.28(t, 1H), 2.48(t, 1H), 3.85(d, 2H), 4.07(s, 2H), 4.53(d, 2H), 7.24(t, 1H), 7.56(m, 1H), 7.84(dd, 1H). |

TABLE 3-continued

Spectral Characterization for Compounds 1=292

| # | HPLC/MS | NMR DATA(300 MHZ) |
|---|---|---|
| 218 | | (Acetone-d6): 3.15(t, 1H), 4.21(s, 2H), 4.68(d, 2H), 7.16(broad s, 1H), 7.55(t, 1H), 8.04(m, 1H), 8.26(dd, 1H). |
| 219 | | (CDCl$_3$): −0.01(m, 2H), 0.27(m, 2H), 0.41(m, 2H), 0.45(m, 2H), 0.79,(m, 1H), 1.17(m, 1H), 2.85(d, 2H), 3.53(d, 2H), 3.98(s, 2H), 7.09(t, 1H), 7.35(m, 1H), 7.62(dd, 1H). |
| 220 | | (CDCl$_3$): 0.35(m, 2H), 0.50(m, 2H), 1.23(m, 1H), 3.57(d, 2H), 4.00(s, 2H), 6.19(s, 1H), 7.10 (t, 1H), 7.64(m, 1H), 7.93 m 1H). |
| 221 | | (CDCl$_3$): 0.93(t, 3H), 1.33(m, 2H), 1.68(m, 2H), 3.72(t, 2H), 3.98(s, 2H), 6.46(s, 1H), 7.11 (dt, 1H), 7.35(dd, 1H), 7.49(t, 2H). |
| 222 | | (CDCl$_3$): 0.08(m, 2H), 0.38(m, 2H), 0.52(m, 4H), 0.88(m, 1H), 1.26(m, 1H), 2.95(d, 2H), 3.63 (d, 2H), 4.08(s, 2H), 7.20(m, 3H), 7.40(m, 1H). |
| 223 | | (CDCl$_3$): 0.37(m, 2H), 0.51(m, 2H), 1.26(m, 1H), 3.63(d, 2H), 4.05(d, 2H), 5.68(br s, 1H), 7.13(ddt, 1H), 7.38(dd, 1H), 7.45(m, 2H). |
| 224 | | (CDCl$_3$): 0.08(m, 2H), 0.37(m, 2H), 0.53(m, 4H), 0.87(m, 1H), 1.26(m, 1H), 2.93(d, 2H), 3.62 (d, 2H), 4.08(d, 2H), 7.31(dd, 1H), 7.41(dd, 1H), 7.57(dd, 1H), 7.63(d, 1H). |
| 225 | | (CDCl$_3$): 2.28(t, 1H), 4.12(s, 2H), 4.57(d, 2H), 5.20(br s, 1H), 7.16(ddt, 1H), 7.42(m, 3H). |
| 226 | | (CDCl$_3$): 2.27(t, 1H), 2.47(t, 1H), 3.84(d, 2H), 4.08(s, 2H), 4.53(d, 2H), 7.31(dd, 1H), 7.53(d, 1H), 7.60(dd, 1H), 7.74(d, 1H). |
| 227 | | (CDCl$_3$): 2.28(t, 1H), 4.12(s, 2H), 4.57(d, 2H), 5.14(br s, 1H), 7.31(d, 1H), 7.59(ddd, 2H), 7.85(d, 1H). |
| 228 | | (DMSO-d6): 1.50(s, 9H), 4.75(s, 2H), 7.09(d, 1H), 7.52(d, 1H), 7.54(d, 2H), 7.87(d, 2H). |
| 229 | | (CDCl$_3$): 0.95(br t, 3H), 1.37(m, 2H), 1.69(m, 2H), 3.76(br, 2H), 4.65(s, 2H), 6.90(d, 1H), 7.02(d, 1H), 7.40(d, 2H), 7.66(d, 2H). |
| 230 | | (Acetone-d6): 1.03(t, 6H), 1.40(m, 4H), 1.70(m, 4H), 3.74(t, 4H), 3.95(s, 4H), 7.88(s, 4H). |
| 231 | | (CDCl$_3$): 0.97(t, 6H), 1.40(m, 4H), 1.74(quintet, 4H), 3.80(t, 4H), 4.09(s, 4H), 5.27(s, 2H), 7.64(d, 4H), 7.75(d, 4H). |
| 232 | | (CDCl$_3$): 0.95(t, 6H), 1.37(dq, 4H), 1.71(quintet, 4H), 3.76(t, 4H), 4.05(s, 4H), 5.52(s, 2H), 7.48(t, 2H), 7.76(dd, 4H), 7.96(s, 2H). |
| 233 | | (CDCl$_3$): 4.76(q, 2H), 7.45(d, 2H), 8.09(d, 2H), 8.55(s, 1H). |
| 234 | | (CDCl$_3$): 0.92(t, 3H), 1.38(m, 4H), 1.9(pentet, 2H), 4.15(t, 3H), 7.43(d, 2H), 8.09(d, 2H), 8.45 (s, 1H). |
| 235 | | (CDCl$_3$): 1.46(t, 3H), 4.22(q, 2H), 7.43(d, 2H), 8.10(d, 2H), 8.45(s, 1H). |
| 236 | | (CDCl$_3$): 4.77(d, 2H), 5.34, 5.38(2ds, 2H), 6.0(m, 1H), 7.43(d, 2H), 8.10(d, 2H), 8.48(s, 1H). |
| 237 | | (methanol-d4): 1.02(t, 3H), 2.1(qt, 2H), 2.46(s, 3H), 4.7(under solvent peak), 7.37(d, 2H), 8.05(d, 2H). |
| 238 | | (CDCl$_3$): 3.83(s, 3H), 7.43(d, 2H), 8.10(d, 2H), 8.46(s, 1H). |
| 239 | | (CDCl$_3$): 2.65(s, 3H), 4.75(q, 2H), 7.43(d, 2H), 8.10(d, 2H). |
| 240 | | (CDCl$_3$): 5.30(s, 2H), 7.34-7.52(m, 7H), 8.08,(d, 2H), 8.46(s, 1H). |
| 241 | | (CDCl$_3$): 1.72(s, 9H), 7.40(d, 2H), 8.05(d, 2H), 8.32(s, 1H). |
| 242 | | (CDCl$_3$): 3.83(s, 3H), 7.47(m, 3H), 8.15(m, 2H), 8.48(s, 1H). |
| 243 | | (DMSO-d6): 7.5(m, 3H), 8.05(m, 2H), 8.55(s, 1H). |
| 244 | | (CDCl$_3$): 0.91(t, 2H), 1.32(hextet, 2H), 1.75(pentet, 2H), 3.79(s, 3H), 4.05(t, 2H), 6.90(d, 2H), 8.02(d, 2H), 8.35(s, 1H). |
| 245 | | (CDCl$_3$): 4.77(q, 2H), 7.35-7.5(m, 2H), 8.04(d, 1H), 8.14(t, 1H), 8.57(s, 1H). |
| 246 | | (CDCl$_3$): 5.28(q, 2H), 7.46(t, 1H), 7.49(dt, 1H), 8.09(dt, 1H), 8.18(t, 1H), 8.86(s, 1H). |
| 247 | | (CDCl$_3$): 2.42(s, 3H), 4.75(q, 2H), 7.27(d, 2H), 8.02(d, 2H), 8.54(s, 1H). |
| 248 | | (CDCl$_3$): 4.77(q, 2H), 7.47(t, 1H), 8.03(d, 2H), 8.56(s, 1H). |
| 249 | | (CDCl$_3$): 4.04(s, 2H), 4.66(q, 2H), 7.25-7.37(m, 5H), 8.39(s, 1H). |
| 250 | | (methanol-d4): 1.27(t, 3H), 4.22(q, 2H), 7.47(d, 2H), 7.76(d, 2H). |
| 251 | | (CDCl$_3$): 1.1-1.55(m, 5H), 1.65-2.0(m, 5H), 2.69(tt, 1H), 4.64(q, 2H), 8.42(s, 1H). |
| 252 | | (CDCl$_3$): 3.88(s, 3H), 4.77(q, 2H), 7.03(ddd, 1H), 7.39(t, 1H), 7.68(t, 1H), 7.75(d, 1H). |
| 253 | | (CDCl$_3$): 2.53(s, 3H), 4.77(q, 2H), 8.05(s, 2H), 8.54(s, 1H). |
| 254 | | (CDCl$_3$): 0.92(t, 2H), 1.30(m, 2H), 1.42(d, 3H), 1.65(m, 1H), 1.90(m, 1H), 5.10(m, 1H), 7.43 (d, 2H), 8.10(d, 2H), 8.43(s, 1H). |
| 255 | | (CDCl$_3$): 0.96(t, 3H), 1.15-1.6(m, 6H), 1.65-2.0(m, 8H), 4.04(t, 2H), 8.32(s, 1H). |
| 256 | | (CDCl$_3$): 1.30(m, 1H), 1.45(m, 2H), 1.7-2.0(m, 7H), 4.8(tt, 2H), 7.43(d, 2H), 8.10(d, 2H), 8.43 (s, 1H). |
| 257 | | (CDCl$_3$): 0.93(t, 2H), 1.39(m, 4H), 1.85(pentet, 2H), 2.52(s, 3H), 4.13(t, 2H), 8.06(s, 2H), 8.43(s, 1H). |
| 258 | | (CDCl$_3$): 0.99(t, 3H), 1.4(m, 2H), 1.85(pentet, 2H), 4.15(t, 2H), 7.45(d, 2H), 8.08(d, 2H), 8.44 (s, 1H). |
| 259 | | (CDCl$_3$): 0.88(t, 3H), 1.23-1.4(m, 10 H), 1.85(pentet, 2H), 4.15(t, 2H), 7.43(d, 2H), 8.08(d, 2H), 8.44(s, 1H). |
| 260 | | (CDCl$_3$): 0.88(t, 3H), 1.23-1.4(m, 14 H), 1.85(pentet, 2H), 4.15(t, 2H), 7.43(d, 2H), 8.09(d, 2H), 8.44(s, 1H). |
| 261 | | (CDCl$_3$): 7.45(m, 3H), 7.77(d, 1H), 7.95(m, 1H), 8.15(d, 1H), 8.63(s, 1H), 8.73(m, 1H). |
| 262 | | (CDCl$_3$): 0.89(t, 3H), 1.35(m, 6H), 1.85(pentet, 2H), 4.15(t, 2H), 7.44(d, 2H), 8.09(d, 2H), 8.44(s, 1H). |
| 263 | | (CDCl$_3$): 4.78(q, 2H), 7.23(m, 2H), 7.48(dddd, 1H), 7.90(td, 1H), 8.57(s, 1H). |
| 264 | | (CDCl$_3$): 4.97(s, 2H), 7.39(d, 2H), 8.03(d, 2H), 8.49(s, 1H). |
| 265 | | (CDCl$_3$): 0.18(s, 9H), 3.85(s, 2H), 7.44(d, 2H), 8.07(d, 2H), 8.42(s, 1H). |
| 266 | | (CDCl$_3$): 5.34(s, 2H), 6.79(d, 1H), 7.02(d, 1H), 7.44(d, 2H), 8.09(d, 2H), 8.47(s, 1H). |
| 267 | | (CDCl$_3$): 4.77(q, 2H), 7.40(td, 1H), 7.41(td, 1H), 7.52(dd, 1H), 7.69(dd, 1H), 8.56(s, 1H). |
| 268 | | (CDCl$_3$): 0.97(t, 3H), 1.37(hextet, 2H), 1.80(pentet, 2H), 2.76(s, 3H), 4.14(t, 2H), 8.38(s, 1H). |

TABLE 3-continued

Spectral Characterization for Compounds 1=292

| # | HPLC/MS | NMR DATA(300 MHZ) |
|---|---|---|
| 269 | | (CDCl$_3$): 0.98(t, 3H), 1.42(hextet, 2H), 1.87(pentet, 2H), 4.17(t, 2H), 7.36(dd, 1H), 7.44(d, 1H), 7.71(d, 1H), 8.46(s, 1H). |
| 270 | | (CDCl$_3$): 0.99(t, 3H), 1.43(hextet, 2H), 1.86(pentet, 2H), 4.17(t, 2H), 7.54(d, 1H), 7.99(dd 1H), 8.25(s, 1H), 8.44(s, 1H). |
| 271 | | (CDCl$_3$): 1.00(t, 3H), 1.43(m, 2H), 1.86(m, 2H), 4.17(t, 2H), 7.42(t, 1H), 8.03(d, 2H), 8.44(s, 1H). |
| 272 | | (CDCl$_3$): 0.50(m, 2H), 0.62(m, 2H), 1.43(m, 1H), 4.02(d, 2H), 7.54(d, 1H), 7.99(dd, 1H), 8.25 (d, 1H), 8.46(s, 1H). |
| 273 | 37% 266 (M + Na)$^a$ 40% 268 (M + Na) | |
| 274 | | (CDCl$_3$): 1.45(t, 3H), 4.11(q, 2H), 6.98(d, 2H), 7.48(d, 2H), 7.86(d, 2H), 8.12(d, 2H), 8.57(s, 1H). |
| 275 | | (CDCl$_3$): 1.31(t, 3H), 2.42(s, 3H), 4.28(q, 2H), 4.89(s, 2H), 7.3(m, 2H), 7.9(m, 2H), 8.53(s, 1H). |
| 276 | | (CDCl$_3$): 3.01(t, 2H), 4.49(t, 2H), 7.75(d, 2H), 7.80(d, 2H), 8.29(d, 2H), 8.34(d, 2H), 8.56(s, 1H). |
| 277 | | (CDCl$_3$): 0.99(t, 3H), 1.44(hextet, 2H), 1.87(pentet, 2H), 4.17(t, 2H), 7.4(m, 2H), 8.05(d, 1H), 8.15(s, 1H), 8.45(s, 1H). |
| 278 | | (CDCl$_3$): 2.47(s, 3H), 7.29(m, 1H), 7.41(m, 3H), 7.55(m, 2H), 8.10(m, 1H), 8.20(bs, 1H), 8.60(s, 1H). |
| 279 | | (CDCl$_3$): 0.92(t, 3H), 1.25(m, 2H), 1.36(m, 4H), 1.83(pentet, 2H), 7.01(d, 1H), 7.50(d, 1H), 7.58(d, 1H), 7.68(d, 1H), 7.89(d, 1H), 8.24(d, 1H), 8.62(s, 1H). |
| 280 | | (CDCl$_3$): 0.99, 1.01(2t, 6H), 1.53,(m, 2H), 1.80(pentet, 2H), 1.91(hextet, 2H), 4.03(t, 2H), 4.11(t, 2H), 6.97(d, 2H), 8.07(d, 2H), 8.43,(s, 1H). |
| 281 | | (CDCl$_3$): 1.06(t, 3H), 1.84(hextet, 2H), 3.99(t, 2H), 4.74(q, 2H), 6.98(d, 2H), 8.06(d, 2H), 8.53,(s, 1H). |
| 282 | | (CDCl$_3$): 3.82(s, 3H), 7.08(m, 4H), 7.13(s, 3H), 7.37(t, 1H), 8.2(d, 1H), 8.46,(s, 1H). |
| 283 | | (CDCl$_3$): 0.97(t, 3H), 1.43(m, 2H), 1.85(m, 2H), 3.86(s, 3H), 4.15(t, 2H), 7.03(m, 2H), 7.43 (dt, 1H), 7.58(dd, 1H), 8.44(s, 1H). |
| 284 | | (CDCl$_3$): 0.97(t, 3H), 1.43(dt, 2H), 1.86(quintet, 2H), 2.42(s, 3H), 2.52(s, 3H), 4.14(t, 2H), 7.27(d, 2H), 8.46(d, 2H). |
| 285 | | (CDCl$_3$): 0.97(t, 3H), 1.43(dt, 2H), 1.83(quintet, 2H), 2.43(s, 3H), 2.53(s, 3H), 4.13(t, 2H), 7.36(m, 2H), 8.30(m, 2H). |
| 286 | | (CDCl$_3$): 0.97(t, 3H), 1.43(dt, 2H), 1.80(quintet, 2H), 2.50(s, 3H), 3.88(s, 3H), 4.13(t, 2H), 6.97(d, 2H), 8.63(d, 2H). |
| 287 | | (CDCl$_3$): 0.99(t, 3H), 1.43(m, 2H), 1.85(m, 2H), 4.15(t, 2H), 6.97(m, 2H), 7.36(dt, 1H), 8.14 (dd, 1H), 8.45(s, 1H), 10.37(s, 1H). |
| 288 | | (CDCl$_3$): 1.00(t, 3H), 1.43(dq, 2H), 1.88(quintet, 2H), 4.21(t, 2H), 7.94(s, 1H), 8.42(s, 1H), 8.54(s, 2H). |
| 289 | | (CDCl$_3$): 1.00(t, 3H), 1.44(dt, 2H), 1.86(quintet, 2H), 4.16(t, 2H), 7.18(t, 1H), 8.07(m, 1H), 8.34(dd, 1H), 8.43(s, 1H). |
| 290 | | (CDCl$_3$): 4.77(q, 2 H), 7.21(t, 1H), 8.10(m, 1H), 8.35(dd, 1H), 8.55(s, 1H). |
| 291 | | (DMSO-d6): 2.32(s, 3H), 4.68(q, 2H), 7.27(d, 2H), 7.36(d, 2H), NH not resolved. |
| 292 | | (CDCl$_3$): 3.88(s, 3H), 4.35(s, 2H), 4.45(br q, 2H), 7.45(s, 3H). |

$^a$Compound 273 was prepared and tested as a 1:1 mixture with its unoxidized(dihydro) form.

The compounds of the present invention have fungitoxic activity, particularly against phytopathogenic fungi. They are active against fungi of a number of classes including Deuteromycetes (Fungi Imperfecti), Basidiomycetes, Phycomycetes and Ascomycetes. More particularly, the method of this invention provides for activity against organisms including, but not limited to, Pyricularia oryzae, Erysiphe graminis, Puccinia recondita, Colletotrichum lagenarium, Helminthosporium species, Alternaria solani, Septoria nodorum, Sclerotinia species, Sphaerotheca fuliginea, Plasmopara viticola, Pseudoperonospora cubensis, Cercospora species, Uncinula necator and Podosphaera leucotricha. More particularly, rice diseases are controlled by the method of the invention. Examples of such rice diseases are seedborne diseases, soilborne diseases, and seedling box and field diseases such as those caused by Pyricularia oryzae and Rhizoctonia species. Additional diseases include powdery mildew incited by Sphaerotheca fulignea (e.g, cucurbit powdery mildew), Uncinula necator (e.g, grape powdery mildew), and Podosphaera leucotricha (e.g, apple powdery mildew). Cereal diseases are controlled such as those caused by Erysiphe graminis, Puccinia recondita, Septoria nodurum and Helminthosporium species. Tomato and potato diseases are controlled such as those caused by Alternaria solani. The compounds of the invention can be applied as fungicidal sprays by methods commonly employed, such as conventional high-gallonage hydraulic sprays, low-gallonage sprays, air-blast, aerial sprays and dusts. Such use conveniently permits treatment of fungal infestations in crops such as vegetables, fruits, ornamentals, seeds, turf, cereal and vines among other plants. The dilution and rate of application will depend upon the type of equipment employed, the method and frequency of application desired and diseases to be controlled, but the effective amount is usually from about 0.01 kilogram (kg) to about 20 kg, of active ingredient (a.i.) per hectare (ha). As a foliar fungicide, a compound of the present invention is usually applied to growing plants at a rate of about 0.1 to about 5 and preferably from about 0.125 to about 0.5 kg per hectare.

As a seed protectant, the amount of toxicant coated on the seed is usually at a dosage rate of about 10 to about 250 grams (g) and preferably from about 20 to about 60 g per 50 kilograms of seed. As a soil fungicide, the chemical can be incorporated in the soil or applied to the surface usually at a rate of 0.5 to about 20 kg and preferably about 1 to about 5 kg per hectare.

The compounds of the present invention are useful for the control of fungi and can be utilized at various loci such as the seed, the water surface, the soil or the foliage. For such purposes, these compounds can be used in the technical or pure form as prepared, as solutions or as formulations. The compounds are usually taken up in a carrier or are formulated so as to render them suitable for subsequent use as fungicides. For example, these chemical agents can be formulated as wettable powders, dry powders, emulsifiable concentrates, dusts, granular formulations, aerosols, or flowable emulsion concentrates. In such formulations, the compounds are extended with a liquid or solid carrier and when desired suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in McCutcheon's Emulsifiers and Detergents, McCutcheon's Emulsifiers and Detergents and McCutcheon's Functional Materials all published annually by McCutcheon Division of MC Publishing Company (New Jersey).

In general, the compounds utilized in this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5 to 50%.

For the preparation of emulsifiable concentrates, the compounds of the invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates; this can be as high as 75%.

Wettable powders suitable for spraying can be prepared by admixing the compound with finely divided solid, such as inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of a compound of this invention, 45 parts of a synthetic precipitated hydrated silicon dioxide sold under the trademark Hi-Sil® and 5 parts of sodium lignosulfonate (Marasperse® N-22). In another preparation of a Kaolin type, (Barden) clay is used in place of the Hi-Sil in the above wettable powder and in another such preparation 25% of the Hi-Sil is replaced with a synthetic sodium silicoaluminate sold under the trademark Zeolex® 7.

Dusts are prepared by mixing the compounds of the invention with finely divided inert solids which can be organic or inorganic in nature. Materials useful for this purpose include botanical flours, silicas, silicates and carbonates. One convenient method for preparing a dust is to dilute a wettable powder with a finely divided carrier. Dust concentrates containing 20% to 80% of the active ingredient are commonly made and are subsequently diluted to 1% to 10% use concentration.

The compounds of the present invention may be utilized in combination with other fungicides such as ferbam, ziram, maneb, mancozeb, zineb, propineb, metham, thiram, the complex of zineb and polyethylene thiuram disulfide, dazomet and mixtures of these with copper salts, dinocap, binapacryl, 2-sec-butyl-4,6-dinitrophenyl isopropyl carbonate, captan, folpet, glyodin, anilazine, ditalimfos, 5-amino-1-[bis(dimethylamino)-phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozolin, iprodione, procymidone, triadimenol, triadimefon, bitertanol, prochloraz, fenarimol, bis-(pchlorophenyl)-3-pyridinemethanol, bis-(pchlorophenyl)-5-pyrimidinemethanol, triarimol, flutriafol, flusilazole, propiconazole, ectaconazole, myclobutanil, fenbuconazole, hexaconazole, cyproconazole, tebuconazole, epoxiconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl) alanine methyl ester, D,L-methyl-N-(2,6-dimethylphenyl)-N-chloroacetyl-D,L-2-amino-butyrolactone, D,L-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fen-propidine, 2,6-dimethyl-N-tridecylmorpholine, dodemorph, triforine, chlorothalonil, dichlone, chloroneb, tricamba, TCPN, dichloran, 2-chloro-1-nitropropane, polychloronitrobenzenes such as pentachloronitro-benzene (PCNB), tetrafluorodichloroacetone, griseofulvin, kasugamycin, polyoxin, validamycin, streptomycin, copper hydroxide, cuprous oxide, basic cupric chloride, basic copper carbonate, copper terephthalate, copper naphthenate, Bordeaux mixture, dodine, pdimethyl-aminobenzenesodium sulfonate, methyl isothiocyanate, 1-thiocyano-2,4-dinitrobenzene, 1-phenylthio-semicarbazide, calcium cyanamide, lime sulfur, thiophanate-methyl, flutolanil, edifenphos, isoprothiolane, probenazole, iprobenfos, tricyclazole, pyroquilon, dimethomorph, cymoxanil, thifluzamide, furalaxyl, ofurace, benalaxyl, oxadixyl, propamocarb, cyprofuram, fenpiclonil, fludioxonil, pyrimethanil, cyprodinil, triticonazole, fluquinconazole, metconazole, spiroxamine, carpropamid, azoxystrobin, kresoxim-methyl, metominostrobin, trifloxystrobin and zoxamide.

Fungicidal Testing Protocols and Test Data

Examples of diseases against which the compounds of the invention are useful include rice diseases such as rice blast, rice sheath blight and helmenthosporium leaf spot, cereal diseases such as wheat powdery mildew, wheat leaf rust, and *septoria*, tomato and potato early blight, peanut early leaf spot, grape and cucumber powdery mildew, apple scab, apple powder mildew, brown rot of fruits, cucumber anthracnose and bean powdery mildew.

Fungicide Screening for Control of Rice Blast and Cucumber Powdery Mildew

Plant Propagation:

Plants used in the fungicide testing program were grown in 2-¼-inch (5.7-cm). square pots containing RediEarth propagation substrate. The plants were raised under greenhouse conditions. The rice plants were 12-days-old and cucumbers were 13-days-old at the time of spraying with chemical treatments.

Sample Preparation:

The sample of the experimental chemical was weighed and dissolved in an acetone-methanol-water solution (A/M/W at 1:1:2 ratio by volume).

Spraying Procedure:

After sprayer calibration, the test solutions were poured into the fungicide sprayer. The fungicide sprayer contains three spray nozzles, located approximately 10 cm above and to the sides of the plants. The spray produced by the nozzles results in uniform coverage of both the upper and lower parts of the plant leaves. After spraying, the treated plants were placed in a drying chamber for 4 hours, prior to sorting.

Cucumber Powdery Mildew:

Cucumber Powdery Mildew (CPM), caused by the fungus *Sphaerotheca fuliginea*, was maintained on large cucumber plants. For inoculum preparation, five to eight leaves depending on size, completely covered with powdery mildew spores, were collected. The leaves were placed in a glass jar and covered with 500 ml of water, containing 5 drops of Tween-80. The material was filtered through two layers of cheesecloth to remove leaf fragments. The spore count was adjusted to $2\times10^5$ spores per ml.

Cucumber plants, cv. "Bush Champion," were used for this test. The plants were thinned to one per pot after the cotyledons were fully developed. Two days before the test, the small leaves and meristem region were removed, leaving only the cotyledons and one large true leaf.

The protectant tests required that the cucumber plants be inoculated 1 day after spraying with the chemical treatment. The plants were inoculated with a hand-held spray bottle with the suspension of fungal spores. The leaves were lightly misted on the upper surface from two different spray directions. Disease development occurred in the greenhouse.

After seven days, the plants were evaluated for percent of disease control. The results are reported as percent control; 100 is total disease control, 0 is no disease control.

Rice Blast:

Rice Blast (RB), caused by the fungus *Pyricularia oryzae*, was maintained on potato dextrose agar (PDA) plates under fluorescent lamps at room temperature. Six different isolates of the fungus were used to prepare the inoculum. Approximately 5 plates of each isolate were used to prepare 250 ml of inoculum. The plates were flooded with water and scraped gently with a rubber spatula. The spore suspension was filtered through one layer of cheese cloth to remove mycelial fragments and agar pieces. The spore count was adjusted to achieve a concentration of $5\times10^6$ spores per ml. Rice plants cv. "M-201," were used for this test. The protectant tests required that the rice plants be inoculated 1 day after spraying with the chemical treatment. The curative tests in the primary screen required that the plants be inoculated 1 day after spraying with the treatment. The plants were inoculated with fungal spores using a DeVilbiss atomizer, using a spray pressure of 30 psi (200 kPa). The inoculated plants were quickly placed in a mist chamber with 100% relative humidity (RH) at 20° for one day and two nights; approximately 40 hours. The plants were moved to the greenhouse for disease development.

Six days after inoculation, the treatment comparisons were made. The results are reported as percent control; 100 is total disease control, 0 is no disease control.

TABLE 4

Protectant Fungicide Data at 300 g/ha for Rice Blast (RB) and Cucumber Powdery Mildew (CPM) in the greenhouse, given in percent control. NT means not tested.

| # | RB | CPM |
| --- | --- | --- |
| 1 | 99 | 80 |
| 2 | 95 | 85 |
| 3 | 80 | 0 |
| 4 | 99 | 50 |
| 5 | 75 | 50 |
| 6 | 90 | 50 |
| 7 | 95 | 75 |
| 8 | 99 | 90 |
| 9 | 100 | 80 |
| 10 | 90 | 0 |
| 11 | 75 | 0 |
| 12 | 95 | 0 |
| 13 | 95 | 0 |
| 14 | 100 | 85 |
| 15 | 75 | 50 |
| 16 | 90 | 75 |
| 17 | 99 | 80 |
| 18 | 95 | 75 |
| 19 | 100 | 75 |
| 20 | 50 | 75 |
| 21 | 0 | 50 |
| 23 | 0 | 50 |
| 24 | 0 | 50 |
| 25 | 75 | 0 |
| 26 | 100 | 95 |
| 27 | 80 | 99 |
| 28 | 85 | 85 |
| 29 | 90 | 90 |
| 30 | 85 | 75 |
| 31 | 50 | 0 |
| 32 | 75 | 50 |
| 33 | 80 | 75 |
| 35 | 50 | 50 |
| 36 | 99 | 50 |
| 37 | 95 | 75 |
| 38 | 0 | 50 |
| 39 | 99 | 85 |
| 40 | 90 | 0 |
| 41 | 100 | 50 |
| 42 | 99 | 50 |
| 43 | 99 | 80 |
| 44 | 85 | 0 |
| 45 | 75 | 0 |
| 46 | 80 | 0 |
| 47 | 100 | 80 |
| 48 | 50 | 0 |
| 49 | 95 | 75 |
| 50 | 100 | 80 |
| 51 | 90 | 0 |
| 52 | 50 | 0 |
| 53 | 75 | 0 |
| 54 | 99 | 85 |
| 55 | 90 | 50 |
| 56 | 80 | 80 |
| 57 | 50 | 0 |
| 58 | 85 | 50 |
| 59 | 50 | 0 |
| 60 | 75 | 0 |
| 61 | 85 | 50 |
| 62 | 85 | 0 |
| 64 | 50 | 0 |
| 65 | 95 | 50 |
| 66 | 50 | 0 |
| 67 | 99 | 80 |
| 68 | 0 | 50 |
| 69 | 95 | 80 |
| 70 | 80 | 80 |
| 71 | 75 | 50 |
| 72 | 75 | 50 |
| 73 | 85 | 75 |
| 74 | 99 | 0 |
| 75 | 0 | 85 |
| 76 | 0 | 25 |
| 77 | 0 | 50 |
| 78 | 0 | 25 |
| 79 | 75 | 50 |

TABLE 4-continued

Protectant Fungicide Data at 300 g/ha for Rice Blast (RB) and Cucumber Powdery Mildew (CPM) in the greenhouse, given in percent control. NT means not tested.

| # | RB | CPM |
|---|----|-----|
| 80 | 0 | 50 |
| 82 | 0 | 25 |
| 83 | 80 | 0 |
| 84 | 80 | 85 |
| 85 | 100 | 50 |
| 86 | 99 | 80 |
| 87 | 90 | 0 |
| 88 | 100 | 50 |
| 89 | 75 | 0 |
| 92 | 0 | 50 |
| 93 | 0 | 75 |
| 94 | 0 | 75 |
| 95 | 25 | 75 |
| 96 | 50 | 75 |
| 97 | 0 | 85 |
| 98 | 85 | 75 |
| 99 | 100 | 80 |
| 100 | 99 | 80 |
| 101 | 100 | 80 |
| 102 | 85 | 50 |
| 103 | 90 | 0 |
| 104 | 99 | 80 |
| 105 | 85 | 75 |
| 106 | 100 | 95 |
| 107 | 99 | 95 |
| 108 | 90 | 85 |
| 109 | 100 | 95 |
| 110 | 99 | 90 |
| 111 | 85 | 90 |
| 112 | 85 | 80 |
| 113 | 99 | 75 |
| 114 | 75 | 0 |
| 115 | 100 | 50 |
| 116 | 85 | 0 |
| 117 | 90 | 0 |
| 118 | 90 | 0 |
| 119 | 99 | 0 |
| 120 | 80 | 0 |
| 121 | 80 | 0 |
| 122 | 75 | 75 |
| 123 | 95 | 50 |
| 124 | 75 | 0 |
| 125 | 50 | 50 |
| 126 | 50 | 0 |
| 127 | 95 | 50 |
| 128 | 90 | 0 |
| 129 | 50 | 75 |
| 130 | 50 | 0 |
| 131 | 80 | 75 |
| 132 | 85 | 50 |
| 133 | 80 | 0 |
| 134 | 80 | 50 |
| 135 | 90 | 50 |
| 136 | 100 | 80 |
| 137 | 85 | 0 |
| 138 | 99 | 0 |
| 139 | 99 | 50 |
| 140 | 0 | 50 |
| 141 | 85 | 50 |
| 142 | 80 | 0 |
| 143 | 98 | 50 |
| 144 | 85 | 0 |
| 145 | 90 | 0 |
| 146 | 95 | 85 |
| 147 | 98 | 0 |
| 148 | 80 | 80 |
| 149 | 95 | 75 |
| 150 | 100 | 50 |
| 151 | 90 | 0 |
| 152 | 85 | 0 |
| 153 | 100 | 0 |
| 154 | 0 | 75 |
| 155 | 90 | 85 |
| 156 | 85 | 0 |
| 157 | 98 | 0 |
| 158 | 85 | 0 |
| 159 | 85 | 0 |
| 160 | 75 | 0 |
| 161 | 80 | 0 |
| 162 | 95 | 50 |
| 163 | 90 | 0 |
| 164 | 100 | 95 |
| 165 | 80 | 0 |
| 166 | 75 | 0 |
| 167 | 85 | 0 |
| 168 | 95 | 50 |
| 169 | 50 | 0 |
| 170 | 90 | 75 |
| 171 | 80 | 50 |
| 172 | 98 | 0 |
| 173 | 50 | 0 |
| 174 | 75 | 0 |
| 175 | 95 | 0 |
| 176 | 50 | 50 |
| 177 | 95 | 50 |
| 178 | 75 | 0 |
| 179 | 75 | 0 |
| 180 | 95 | 90 |
| 181 | 50 | 0 |
| 182 | 85 | 0 |
| 183 | 95 | 0 |
| 184 | 85 | 75 |
| 185 | 80 | 75 |
| 186 | 85 | 0 |
| 187 | 80 | 0 |
| 188 | 80 | 0 |
| 189 | 80 | 75 |
| 190 | 80 | 0 |
| 191 | 95 | 50 |
| 192 | 99 | 75 |
| 193 | 80 | 0 |
| 194 | 80 | 0 |
| 195 | 99 | 50 |
| 196 | 99 | 0 |
| 197 | 99 | 75 |
| 198 | 80 | 0 |
| 199 | 90 | 0 |
| 200 | 85 | 0 |
| 201 | 85 | 0 |
| 202 | 90 | 0 |
| 203 | 85 | 0 |
| 204 | 75 | 85 |
| 206 | 85 | 80 |
| 207 | 100 | 85 |
| 208 | 95 | 50 |
| 209 | 75 | 0 |
| 210 | 100 | 25 |
| 211 | 100 | 85 |
| 212 | 98 | 85 |
| 213 | 85 | 50 |
| 214 | 50 | 85 |
| 215 | 85 | 0 |
| 216 | 98 | 80 |
| 217 | 85 | 0 |
| 218 | 98 | 80 |
| 219 | 50 | 75 |
| 220 | 100 | 80 |
| 221 | 85 | 80 |
| 222 | 0 | 50 |
| 223 | 95 | 80 |
| 224 | 75 | 50 |
| 225 | 80 | 0 |
| 226 | 50 | 0 |
| 227 | 90 | 75 |
| 229 | 0 | 50 |
| 230 | 75 | 0 |

TABLE 4-continued

Protectant Fungicide Data at 300 g/ha for Rice Blast (RB) and Cucumber Powdery Mildew (CPM) in the greenhouse, given in percent control. NT means not tested.

| # | RB | CPM |
|---|---|---|
| 231 | 85 | 0 |
| 232 | 100 | 99 |
| 233 | 100 | 80 |
| 234 | 100 | 80 |
| 235 | 90 | 80 |
| 236 | 99 | 90 |
| 237 | 0 | 95 |
| 238 | 50 | 90 |
| 240 | 95 | 75 |
| 241 | 50 | 0 |
| 243 | 75 | 0 |
| 244 | 100 | 50 |
| 245 | 99 | 0 |
| 246 | 100 | 0 |
| 247 | 100 | 80 |
| 248 | 100 | 80 |
| 249 | 85 | 0 |
| 250 | 90 | 50 |
| 251 | 75 | 0 |
| 252 | 85 | 0 |
| 253 | 100 | 50 |
| 254 | 95 | 0 |
| 255 | 50 | 0 |
| 256 | 95 | NT |
| 257 | 95 | 50 |
| 258 | 100 | 75 |
| 259 | 90 | 75 |
| 260 | 75 | 0 |
| 261 | 50 | 0 |
| 262 | 85 | 80 |
| 263 | 80 | 85 |
| 264 | 50 | 0 |
| 265 | 85 | 90 |
| 266 | 90 | 50 |
| 267 | 80 | 85 |
| 268 | 0 | 75 |
| 269 | 99 | 0 |
| 270 | 100 | 95 |
| 271 | 99 | 50 |
| 272 | 100 | 80 |
| 273[a] | 100 | 0 |
| 274 | 85 | 0 |
| 275 | 85 | 0 |
| 276 | 85 | 0 |
| 277 | 95 | 0 |
| 278 | 85 | 0 |
| 280 | 50 | 0 |
| 281 | 85 | 95 |
| 282 | 75 | 75 |
| 283 | 90 | 50 |
| 287 | 80 | 0 |
| 288 | 0 | 75 |
| 289 | 100 | 50 |
| 290 | 100 | 50 |
| 291 | 80 | 0 |
| 292 | 99 | 75 |
| 293 | 100 | 50 |
| 294 | 100 | 80 |
| 295 | 99 | 50 |
| 296 | 98 | 75 |

[a]Compound 273 was prepared and tested as a 1:1 mixture with its unoxidized (dihydro) form.

For insecticidal use, the compositions and compounds of this invention can be applied directly to the locus to be protected, as for example, the area around or upon economic plants infected with insects or to plants on which infestation is to be prevented. Examples of injurious insects belong to the orders *Lepidoptera, Coleoptera, Diptera, Thysanoptera, Hymenoptera, Heteroptera, Homoptera, Orthoptera,* and *Acarina*. The compounds and compositions may be used either as contact or systemic pesticides. The compounds of the invention are applied to the insect's habitat at a rate of 0.0005 to 10 kilograms per hectare, preferably 0.05 to 5 and most preferably from 0.1 to 1 kilogram per hectare.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as "systemic" application. Alternatively, the active compound may be applied to the soil and contacted therein with the insects and other pests to be controlled. This means of application is referred to as "soil" application. In another alternative, the active compound may be foliarly applied to the plants to be freed from insects and other pests which feed on the foliage.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001-99% by weight. For compositions suitable for storage or transportation, the amount of active ingredient is preferably between about 0.5-90% by weight, and more preferably between about 1-75% by weight of the mixture. Compositions suitable for direct application or field application generally contain the active compound in an amount substantially between about 0.0001-95%, preferably between about 0.0005-90% by weight, and more preferably between about 0.001-75% by weight of the mixture. The composition can also be stated as a ratio of the compound to the carrier. In the present invention the weight ratio of these materials (active compound/carrier) can vary from 99:1 to 1:4 and more preferably from 10:1 to 1:3.

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combatting or controlling pests which compromises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habitat thereof (i.e, the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

Insecticidal Testing Protocol and Test Data

Numerous compounds of this invention were tested for insecticidal activity. This testing was carried out using two different protocols.

Protocol 1:

Test Solution Preparation

A test solution containing 1250 parts per million (ppm) was prepared by dissolving the test compound in 15 milliliters of solvent (acetone: methanol, 1:1) and then adding 65 milliliters of a second solvent (acetone: water, 1:1) to give an acetone:water: methanol system of 50: 40:10.

Sprayer

The enclosed spraying chamber consisted of a single spray nozzle mounted on a boom moving at a fixed speed and distance over stationary targets. The vertical distance from the nozzle tip to the targets was adjusted to give rates varying from 150 g/ha to 600 g/ha 3. Test Species Tests were conducted with the following pests.

| | Foliar Species | |
|---|---|---|
| SYMBOL | COMMON NAME | LATIN NAME |
| AW | Southern Armyworm | *Spodoptera eridania* |
| BB | Mexican Bean Beetle | *Epilachna verivestis* |
| MTA | Two-Spotted Spider Mite | *Tetranychus urticae* |

Southern Armyworm

Individual fully expanded primary lima bean (*Phaseolus limensis*) leaves were placed bottom side up on moistened pieces of filter paper in Petri dishes. The leaves were sprayed with the test solutions and allowed to dry. The dishes were infested with 5 third instar larvae of the southern armyworm, covered with the lids, and held at 27° C. Armyworm control was rated by visual inspection after 48 hours. A rating of 100 indicated that all larvae were dead. A rating of 0 indicated no dead larvae and normal feeding. Intermediate control was indicated by intermediate ratings.

Mexican Bean Beetle

Individual fully expanded primary lima bean (*Phaseolus limensis*) leaves were placed bottom side up on moistened pieces of filter paper in Petri dishes. The leaves were sprayed with the test solutions and allowed to dry. The dishes were infested with 5 third instar larvae of the mexican bean beetle, covered with the lids, and held at 27° C. Bean beetle control was rated by visual inspection after 48 hours. A rating of 100 indicated that all larvae were dead. A rating of 0 indicated no dead larvae and normal feeding. Intermediate control was indicated by intermediate ratings.

C. Two Spotted Spider Mite

A pad of moistened cotton was placed in a Petri dish. A 1-inch square section cut from a fully expanded primary lima bean (*Phaseolus limensis*) leaf was positioned bottom side up on the moist cotton. The leaf square was infested with approximately 50 adult female mites. The dishes were sprayed with the test solutions and held at 27° C. for mortality determination 1-day post-treatment. The percentage of mites killed were rated from 100% (all dead) to 0% (all alive).

Protocol 2:

Candidate compounds are solubilized in a solvent mix (either acetone/methanol/water or DMSO/water). The compounds are screened against *Aedes aegypti* (yellowfever mosquito, YFM) or *Caenorhabditis elegans* nematode (CE).

For screening *A. aegypti*, wells are filled with 1 mL of diet (500 ppm of a 1:1 liver powder/yeast in D.I. water). The appropriate volume of test material is added to the wells to provide a final concentration of 3 ppm. Approximately 10-15 three (3) day old mosquito larvae are used for infesting the test wells. Mosquito larva trays are stored in an 27° C. room and mortality readings taken 3 days after infesting. A compound is declared active if all organisms within the test well are dead at reading time.

For screening *C. elegans*, wells are filled with 1 mL of *E. coli* diet (cell density=4% transmittance at 535 nM). The appropriate volume of test material is added to the wells to provide a final concentration of either 15 or 20 ppm. Approximately 10-15 four (4) day old nematodes are used for infesting the test wells. Test plates are stored at 21° C. and mortality readings taken 6 days after infesting. A compound is declared active if all organisms within the test well are dead at reading time.

TABLE 5

Insecticide data for compounds of the invention

| | | Protocol 1 | | | Protocol 2 | |
|---|---|---|---|---|---|---|
| | | | | | CE | YFM |
| Cmpd. Number | DOSE | AW | BB | MTA | Insect Active | Insect Active |
| 4 | 300 | 75 | 0 | 0 | NT | NT |
| 5 | 300 | NT | 75 | 0 | NT | NT |
| 5 | 600 | 50 | NT | NT | NT | NT |
| 6 | 300 | 0 | 100 | 0 | NT | NT |
| 7 | 300 | 0 | 100 | 100 | NT | NT |
| 8 | 300 | 0 | 0 | 100 | NT | NT |
| 9 | NT | NT | NT | NT | Y | Y |
| 16 | 150 | NT | NT | 69 | Y | Y |
| 18 | 150 | NT | NT | 100 | Y | N |
| 19 | 150 | 0 | 100 | 90 | NT | NT |
| 26 | 300 | 0 | 50 | 0 | NT | NT |
| 27 | 300 | 0 | 75 | 0 | NT | NT |
| 29 | 300 | 0 | 0 | 90 | NT | NT |
| 33 | 300 | 0 | 100 | 75 | NT | NT |
| 34 | 300 | 0 | 75 | 0 | NT | NT |
| 37 | 300 | 100 | 75 | 75 | NT | NT |
| 40 | 300 | 0 | 50 | 90 | NT | NT |
| 41 | 300 | 0 | 50 | 0 | NT | NT |
| 43 | 150 | 50 | 0 | 0 | NT | NT |
| 44 | 150 | 75 | 0 | 0 | NT | NT |
| 48 | 150 | 0 | 0 | 75 | NT | NT |
| 50 | 150 | 0 | 0 | 75 | N | N |
| 52 | 150 | 0 | 0 | 100 | NT | Y |
| 60 | NT | NT | NT | NT | Y | N |
| 61 | NT | NT | NT | NT | Y | N |
| 63 | 150 | NT | NT | 0 | Y | Y |
| 65 | NT | NT | NT | NT | Y | N |
| 67 | NT | NT | NT | NT | Y | N |
| 69 | 150 | NT | NT | 68 | Y | N |

TABLE 5-continued

Insecticide data for compounds of the invention

| Cmpd. Number | Protocol 1 | | | | Protocol 2 | |
|---|---|---|---|---|---|---|
| | DOSE | AW | BB | MTA | CE Insect Active | YFM Insect Active |
| 70 | 150 | NT | NT | 71 | N | N |
| 81 | NT | NT | NT | NT | N | Y |
| 86 | NT | NT | NT | NT | N | Y |
| 91 | NT | NT | NT | NT | N | Y |
| 99 | NT | NT | NT | NT | Y | N |
| 100 | 150 | NT | NT | 25 | Y | N |
| 101 | 150 | NT | NT | 0 | Y | N |
| 103 | 150 | NT | NT | 23 | Y | Y |
| 109 | 150 | NT | NT | 90 | Y | N |
| 110 | 150 | NT | NT | 100 | Y | Y |
| 112 | 150 | NT | NT | 0 | Y | N |
| 123 | 150 | NT | NT | 0 | Y | N |
| 127 | 150 | NT | NT | 95 | N | N |
| 128 | NT | NT | NT | NT | Y | N |
| 133 | 150 | NT | NT | 0 | N | Y |
| 134 | 300 | NT | NT | NT | N | Y |
| 135 | 150 | NT | NT | 43 | N | N |
| 137 | NT | NT | NT | NT | Y | Y |
| 162 | NT | NT | NT | NT | Y | N |
| 163 | 150 | NT | NT | 100 | N | N |
| 164 | NT | NT | NT | NT | Y | Y |
| 171 | NT | NT | NT | NT | N | Y |
| 175 | NT | NT | NT | NT | Y | N |
| 178 | NT | NT | NT | NT | Y | N |
| 179 | NT | NT | NT | NT | Y | N |
| 180 | NT | NT | NT | NT | Y | N |
| 183 | NT | NT | NT | NT | Y | N |
| 203 | NT | NT | NT | NT | N | Y |
| 205 | NT | NT | NT | NT | N | Y |
| 209 | NT | NT | NT | NT | N | Y |
| 210 | NT | NT | NT | NT | N | Y |
| 223 | NT | NT | NT | NT | Y | NT |
| 233 | 300 | 50 | 75 | 0 | NT | NT |
| 234 | 300 | 0 | 0 | 100 | NT | NT |
| 235 | 300 | 0 | 100 | 100 | NT | NT |
| 236 | 300 | 0 | 100 | 100 | NT | NT |
| 238 | 300 | 0 | 75 | 100 | NT | NT |
| 239 | 300 | 0 | 75 | 0 | NT | NT |
| 240 | 300 | 50 | 75 | 100 | NT | NT |
| 241 | 300 | 0 | 100 | 100 | NT | NT |
| 242 | 300 | 0 | 90 | 100 | NT | NT |
| 245 | 300 | 100 | 100 | 100 | NT | NT |
| 247 | 300 | 0 | 90 | 0 | NT | NT |
| 248 | 150 | 0 | 0 | 100 | NT | NT |
| 249 | 150 | 100 | 0 | 90 | NT | NT |
| 251 | 150 | 0 | 50 | 75 | NT | NT |
| 252 | 150 | 0 | 100 | 50 | NT | NT |
| 253 | 150 | 0 | 0 | 100 | NT | NT |
| 254 | 150 | 0 | 100 | 100 | Y | N |
| 255 | 150 | 0 | 90 | 100 | N | N |
| 256 | 150 | 0 | 0 | 90 | N | N |
| 258 | NT | NT | NT | NT | Y | N |
| 259 | 150 | NT | NT | 0 | Y | N |
| 260 | 150 | NT | NT | 0 | Y | N |
| 262 | 150 | NT | NT | 0 | Y | Y |
| 264 | NT | NT | NT | NT | Y | N |
| 265 | 150 | NT | NT | 0 | Y | Y |
| 266 | 150 | NT | NT | 0 | Y | Y |
| 270 | 150 | NT | NT | 0 | Y | N |
| 271 | 150 | NT | NT | 93 | Y | Y |
| 277 | NT | NT | NT | NT | Y | Y |
| 278 | NT | NT | NT | NT | Y | N |
| 284 | NT | NT | NT | NT | Y | Y |
| 285 | NT | NT | NT | NT | N | Y |
| 286 | NT | NT | NT | NT | N | Y |
| 288 | NT | NT | NT | NT | N | Y |

Y = yes (active);
N = no (inactive);
NT = not tested.

We claim:

1. The compound of the formula:

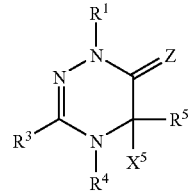

wherein
   $R^1$ is $(C_1-C_{10})$alkyl, halo$(C_1-C_4)$alkyl, $(C_2-C_6)$alkenyl, $(C_2-C_6)$alkynyl, cyclo$(C_3-C_6)$alkyl$(C_1-C_2)$alkyl, tri$(C_1-C_4)$-alkylsilyl $(C_1-C_2)$alkyl where the three alkyl groups may be the same or different,
   $R^3$ is phenyl, naphthyl, or phenyl or naphthyl substituted with from one to three substituents independently selected from the group consisting of halo, $(C_1-C_4)$alkyl, halo$(C_1-C_2)$alkyl and halo$(C_1-C_2)$alkoxy,
   $R^4$ is a hydrogen atom, $(C_1-C_4)$alkylsulfonyl, $(C_1-C_4)$alkoxy-carbonylthio, $(C_2-C_4)$alkenyloxycarbonyl, $(C_2-C_6)$alkynyl, $(C_2-C_4)$alkynyloxycarbonyl, $(C_1-C_4)$alkoxyoxalyl, or may form C=N when taken together with $X^5$,
   $R^5$ is a hydrogen atom, $(C_1-C_4)$alkoxy or $(C_1-C_4)$alkylthio,
   Z is an oxygen atom or a sulfur atom, and
   $X^5$ is a hydrogen atom or taken together with $R^4$ forms C=N, with the proviso that when $X^5$ and $R^4$ form C=N, $R^3$ is not phenyl.

2. The compound of claim 1 wherein
   $R^1$ is $(C_1-C_{10})$alkyl, halo$(C_1-C_{10})$alkyl, $(C_2-C_8)$alkenyl, halo$(C_2-C_8)$alkenyl, $(C_2-C_8)$alkynyl, cyclo$(C_3-C_6)$alkyl$(C_1-C_2)$alkyl, tri$(C_1-C_4)$alkylsilyl$(C_1-C_2)$alkyl where the three alkyl groups may be the same or different,
   $R^3$ is dihalosubstitutedphenyl, di$(C_1-C_4)$alkylsubstitutedphenyl, di(halo$(C_1-C_2)$alkyl)substitutedphenyl, monohalomono$(C_1-C_4)$alkylsubstitutedphenyl or monohalomono(halo$(C_1-C_4)$alkyl)substitutedphenyl,
   $R^4$ and $R^5$ are hydrogen.

3. A fungicidal composition comprising a fungicidally effective amount of a compound of the formula

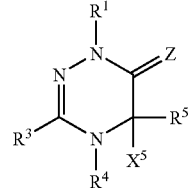

wherein
   $R^1$ is $(C_1-C_{10})$alkyl, halo$(C_1-C_4)$alkyl, $(C_2-C_6)$alkenyl, $(C_2-C_6)$alkynyl, cyclo$(C_3-C_6)$alkyl$(C_1-C_2)$alkyl, tri$(C_1-C_4)$-alkylsilyl $(C_1-C_2)$alkyl where the three alkyl groups may be the same or different,
   $R^3$ is phenyl, naphthyl, or phenyl or naphthyl substituted with from one to three substituents independently selected from the group consisting of halo, $(C_1-C_4)$alkyl, halo$(C_1-C_2)$alkyl and halo$(C_1-C_2)$alkoxy, $R^4$ is a hydrogen atom, $(C_1\text{-}C_4)$alkylsulfonyl, $(C_1\text{-}C_4)$ alkoxy-carbonylthio, $(C_2\text{-}C_4)$alkenyloxycarbonyl, $(C_2\text{-}C_6)$alkynyl, $(C_2\text{-}C_4)$alkynyloxycarbonyl, $(C_1\text{-}C_4)$ alkoxyoxalyl, or may form C=N when taken together with $X^5$, $R^5$ is a hydrogen atom, $(C_1\text{-}C_4)$alkoxy or $(C_1\text{-}C_4)$alkylthio, Z is an oxygen atom or a sulfur atom, and $X^5$ is a hydrogen atom or taken together with $R^4$ forms C=N, with the proviso that when $X^5$ and $R^4$ form C=N, $R^3$ is not phenyl.

4. The fungicidal composition of claim 3 wherein
$R^1$ is $(C_1\text{-}C_{10})$alkyl, halo$(C_1\text{-}C_{10})$alkyl, $(C_2\text{-}C_8)$alkenyl, halo$(C_2\text{-}C_8)$alkenyl, $(C_2\text{-}C_8)$alkynyl, cyclo$(C_3\text{-}C_6)$alkyl $(C_1\text{-}C_2)$alkyl, tri$(C_1\text{-}C_4)$alkylsilyl$(C_1\text{-}C_2)$alkyl where the three alkyl groups may be the same or different, $R^3$ is dihalosubstitutedphenyl, di$(C_1\text{-}C_4)$alkylsubstitutedphenyl, di(halo$(C_1\text{-}C_2)$alkyl)substitutedphenyl, monohalomono$(C_1\text{-}C_4)$alkylsubstitutedphenyl or monohalomono(halo$(C_1\text{-}C_4)$-alkyl)substitutedphenyl, $R^4$ and $R^5$ are hydrogen.

5. An insecticidal composition comprising a insecticidally effective amount of a compound of the formula

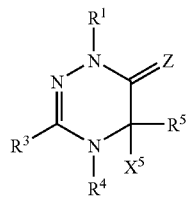

wherein
$R^1$ is $(C_1\text{-}C_{10})$alkyl, halo$(C_1\text{-}C_4)$alkyl, $(C_2\text{-}C_6)$alkenyl, $(C_2\text{-}C_6)$alkynyl, cyclo$(C_3\text{-}C_6)$alkyl$(C_1\text{-}C_2)$alkyl, tri$(C_1\text{-}C_4)$-alkylsilyl $(C_1\text{-}C_2)$alkyl where the three alkyl groups may be the same or different, $R^3$ is phenyl, naphthyl, or phenyl or naphthyl substituted with from one to three substituents independently selected from the group consisting of halo, $(C_1\text{-}C_4)$alkyl, halo$(C_1\text{-}C_2)$alkyl and halo$(C_1\text{-}C_2)$alkoxy, $R^4$ is a hydrogen atom, $(C_1\text{-}C_4)$alkylsulfonyl, $(C_1\text{-}C_4)$ alkoxy-carbonylthio, $(C_2\text{-}C_4)$alkenyloxycarbonyl, $(C_2\text{-}C_6)$alkynyl, $(C_2\text{-}C_4)$alkynyloxycarbonyl, $(C_1\text{-}C_4)$ alkoxyoxalyl, or may form C=N when taken together with $X^5$, $R^5$ is a hydrogen atom, $(C_1\text{-}C_4)$alkoxy or $(C_1\text{-}C_4)$alkylthio, Z is an oxygen atom or a sulfur atom, and $X^5$ is a hydrogen atom or taken together with $R^4$ forms C=N, with the proviso that when $X^5$ and $R^4$ form C=N, $R^3$ is not phenyl.

6. A method of controlling a fungus comprising applying a fungicidally effective amount of a composition of claim 3 or 4 to the fungus, to the locus of the fungus or to the growth medium of said fungus.

7. A method of controlling an insect comprising applying an insecticidally effective amount of a composition of claim 5 to the insect, to the locus of the insect or to the growth medium of said insect.

* * * * *